US007892755B2

(12) United States Patent
Ito et al.

(10) Patent No.: US 7,892,755 B2
(45) Date of Patent: Feb. 22, 2011

(54) SCREENING METHOD

(75) Inventors: Yasuaki Ito, Ibaraki (JP); Kazunori Nishi, Ibaraki (JP); Shoichi Ohkubo, Osaka (JP); Masataka Harada, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 123 days.

(21) Appl. No.: 11/661,555

(22) PCT Filed: Aug. 29, 2005

(86) PCT No.: PCT/JP2005/016169

§ 371 (c)(1),
(2), (4) Date: Feb. 27, 2007

(87) PCT Pub. No.: WO2006/025551

PCT Pub. Date: Mar. 9, 2006

(65) Prior Publication Data

US 2008/0103215 A1    May 1, 2008

(30) Foreign Application Priority Data

Aug. 30, 2004    (JP)    ............................. 2004-250786

(51) Int. Cl.
*G01N 33/566* (2006.01)
*A61K 38/00* (2006.01)
(52) U.S. Cl. .................. 435/7.1; 435/7.8; 435/334; 435/361; 530/350
(58) Field of Classification Search ................ None
See application file for complete search history.

(56) References Cited

U.S. PATENT DOCUMENTS

| 5,843,987 | A | 12/1998 | Rajagopalan et al. | |
| 7,119,190 | B2 * | 10/2006 | Liaw et al. | 536/23.5 |
| 2002/0168720 | A1 * | 11/2002 | Hinuma et al. | 435/69.1 |
| 2007/0048740 | A1 | 3/2007 | Isogai et al. | |
| 2007/0166772 | A1 * | 7/2007 | Roegel et al. | 435/7.92 |

FOREIGN PATENT DOCUMENTS

| EP | 1312374 A1 | 5/2003 |
| EP | 1447413 | 8/2004 |
| WO | WO-99/33978 | 8/1999 |
| WO | WO 99/64452 | 12/1999 |
| WO | WO-01/46414 A1 | 6/2001 |
| WO | WO-02/68600 A2 | 6/2002 |
| WO | WO-2004/040000 A2 | 5/2004 |
| WO | WO-2004/047863 A2 | 10/2004 |
| WO | WO-2005/059546 A2 | 6/2005 |

OTHER PUBLICATIONS

Spanaswick et al. (1995) Excitation of sympathetic preganglionic neurons via metabotropic excitatory amino acid receptors. Neuroscience, vol. 68, No. 4, paged 1247-1261.*
Armstrng et al. (1998) Structure of a glutamate-receptor ligand-binding core in complex with kainate, Nature, vol. 395, No. 6705, pp. 913-917.*
Lampinen et al. (1998) AMPA receptors and bacterial periplasmic amino acid-binding proteins share the ionic mechanism of ligand recognition, EMBO J., vol. 17, No. 16 pp. 4704-4711.*
SEQ Alignment (2009) attachment 1, p. 1.*
Simon et al. (1991) Diversity of G proteins in signal transduction, Science, vol. 252, pp. 802-808.*
Hulme et al. (1995) The role of charge interactions in muscarinic agonist binding, and receptor-response coupling, Life sci., vol. 56, No. 11/12, pp. 891-898.*
Taniguchi et al. (2003) 5-Nitro-2-(3-phenylpropylamino)benzoic acid is a GPR35 agonist, Pharmacology, vol. 82, No. 4, pp. 245-249.*
Ohshiro et al. (2008) GPR35 is a functional receptor in rat dorsal root ganglion neurons, Biochem. Biophys. Res. Commun., vol. 365, No. 2, pp. 344-348.*
Dictionary (2009, updated) "represent", Encarta.msn.com/dictionary_/represented.html, pp. 1-3.*
Cabrera-vera et al. (2003) Insights into G protein structure, function, and regulation, Endocr. Rev., vol. 24, No. 6, pp. 765-781.*
Supplementary Partial European Search Report dated Jan. 11, 2008, for corresponding EPO application 05776830.
O'Dowd B.F. et al., Discovery of three novel 0-protein-coupled receptor genes., Genomics, 1998, 47(2), p. 310-313.
Okumura S. et. al., Cloning of a G-protein-coupled receptor that shows an activity to transform NIH3T3 cells and is expressed ingastric cancer cells., Cancer Sci., Feb. 2004, 95(2), p. 131-135.
Davies S.N., Quinoxalinediones as Excitatory Amino Acid Antagonists in the Vertebrate Central Nervous System, International Review of Neurobiology, vol. 32, 1990, p. 281-303.
Hayatsu H. et. al., Dietary inhibitors of mutagenesis and carcinogenesis, Mutation Research, vol. 202, 1988, p. 429-446.

* cited by examiner

*Primary Examiner*—Anand U Desai
*Assistant Examiner*—Samuel Liu
(74) *Attorney, Agent, or Firm*—Edwards Angell Palmer & Dodge LLP; David G. Conlin; Mark D. Russett

(57) ABSTRACT

The present invention provides a method of screening a compound or its salt that alters binding properties of a protein comprising the same or substantially the same amino acid sequence as the amino acid sequence represented by SEQ ID NO: 1, or a salt thereof, and a ligand capable of specifically binding to the protein or its salt, which comprises using (a) the protein, its partial peptide, or a salt thereof and (b) the ligand; a screening kit therefor, and so on. The screening method and kit of the present invention are useful for screening an agent for the prevention/treatment of, e.g., digestive tract disorders, cancer, immune disorders, type II diabetes mellitus or obesity, etc.

11 Claims, 2 Drawing Sheets

SCREENING METHOD

CROSS-REFERENCE TO RELATED APPLICATIONS

This application is the 35 U.S.C. §371 national stage of PCT application PCT/JP2005/016169, filed Aug. 29, 2005, which claims priority to Japanese patent application No. 2004-250786, filed Aug. 30, 2004. The contents of these applications are incorporated herein by reference in their entirety.

TECHNICAL FIELD

The present invention relates to screening methods and screening kits for medicaments which comprises using ligands capable of specifically binding to GPR35 receptors and GPR35 receptors, compounds obtainable by the screening methods or kits, etc. More particularly, the present invention relates to screening methods and screening kits for preventive/therapeutic agents for digestive disorders, and so on.

BACKGROUND ART

G protein-coupled receptors (GPCR) are seven-transmembrane receptors and are responsible for actions to transduce the signal of hormones, neurotransmitters, cytokines and other molecules, across the cell membrane.

Human GPR35 (Non-Patent Publication 1: Genomics, 47, 310-313, 1988) is one of GPCR, for which no ligand has not been reported. It is reported that the cDNA fragments of GPR35 extracted from human gastric cancer are speculated to have transformation activities in NIH3T3 cells (Non-Patent Publication 2: Cancer Science, 95, 131-135, 2004).

6,7-Dinitroquinoxaline-2,3-dione is known as a N-methyl-D-aspartic acid (NMDA) antagonist acting on glutamate receptors (Non-Patent Publication 3: International Review of Neurobiology, 32, 281-303, 1990).

Ellagic acid is a naturally occurring polyphenol contained in strawberries or the like and known to have physiological actions including an anticarcinogenic activity (Non-Patent Publication 4: Mutation Research, 202, 429-446, 1988), an antioxidant activity (Non-Patent Publication 5: Biochemical Pharmacology, 42, 1441-1445, 1991), etc.

DISCLOSURE OF INVENTION

There is a need for safe and excellent drugs for the prevention/treatment of digestive diseases, cancer, immune disorders, diabetes mellitus, etc.

In order to solve the foregoing problems, the present inventors made extensive studies and found that quinoxaline-2,3-dione compounds such as 6,7-dinitroquinoxaline-2,3-dione, etc. and ellagic acid are ligands for GPR35. The inventors inferred that it would be possible to search for drugs effective for digestive disorders, cancer, immune disorders, etc. Based on these findings, the inventors have made further studies and as a result have come to accomplish the present invention.

That is, the present invention relates to the following features:

[1] a method of screening a compound or a salt thereof that alters the binding property of a protein comprising the same or substantially the same amino acid sequence as the amino acid sequence represented by SEQ ID NO: 1, or a salt thereof, to a ligand capable of specifically binding to said protein or a salt thereof, which comprises using (a) said protein, its partial peptide, or a salt thereof, and (b) said ligand;

[2] the screening method according to [1], wherein the ligand is a quinoxaline-2,3-dione compound;

[3] the screening method according to [1], wherein the quinoxaline-2,3-dione compound is 6,7-dinitroquinoxaline-2,3-dione, 6-nitro-7-sulfamoylbenzo[f]quinoxaline-2,3-dione, 6-cyano-7-nitroquinoxaline-2,3-dione or 5,7-dinitroquinoxaline-2,3-dione;

[4] the screening method according to [1], wherein the ligand is ellagic acid;

[5] the screening method according to [1], wherein substantially the same amino acid sequence as the amino acid sequence represented by SEQ ID NO: 1 is an amino acid sequence represented by SEQ ID NO: 7, SEQ ID NO: 19, SEQ ID NO: 21, SEQ ID NO: 23 or SEQ ID NO: 27;

[6] the screening method according to [1], wherein (a) when a ligand capable of specifically binding to a protein comprising the same or substantially the same amino acid sequence as the amino acid sequence represented by SEQ ID NO: 1, its partial peptide, or a salt thereof is brought in contact with said protein, its partial peptide, or a salt thereof; and (b) when said ligand and a test compound are brought in contact with said protein, its partial peptide, or a salt thereof; the binding amounts of said ligand to said protein, its partial peptide, or a salt thereof, are determined and compared;

[7] the screening method according to [1], wherein (a) when a ligand capable of specifically binding to a protein comprising the same or substantially the same amino acid sequence as the amino acid sequence represented by SEQ ID NO: 1, its partial peptide, or a salt thereof, is brought in contact with a cell containing said protein, its partial peptide, or a salt thereof, or a membrane fraction of the cell; and (b) when said ligand and a test compound are brought in contact with a cell containing said protein, its partial peptide, or a salt thereof, or a membrane fraction of the cell; the binding amounts of said ligand to the cell or the membrane fraction of the cell are determined and compared;

[8] the screening method according to [7], wherein the protein comprising the same or substantially the same amino acid sequence as the amino acid sequence represented by SEQ ID NO: 1, its partial peptide, or a salt thereof is a protein, its partial peptide, or a salt thereof, which is expressed on a cell membrane by culturing a transformant bearing a DNA encoding said protein, its partial peptide, or a salt thereof;

[9] the screening method according to [6] to [8], wherein the ligand is a labeled ligand;

[10] the screening method according to [1], wherein (a) when a ligand capable of specifically binding to a protein comprising the same or substantially the same amino acid sequence as the amino acid sequence represented by SEQ ID NO: 1, its partial peptide, or a salt thereof, is brought in contact with said protein, its partial peptide, or a salt thereof, and (b) when a test compound is brought in contact with said protein, its partial peptide, or a salt thereof, in the presence or absence of said ligand; the cell stimulating activities mediated by said protein, its partial peptide, or a salt thereof are determined and compared;

[11] the screening method according to [1], wherein (a) when a ligand capable of specifically binding to a protein comprising the same or substantially the same amino acid sequence as the amino acid sequence represented by SEQ ID NO: 1, its partial peptide, or a salt thereof, is brought in contact with a cell containing said protein, its partial peptide, or a salt thereof, or a membrane fraction of the cell;

and (b) when a test compound is brought in contact with a cell containing said protein, its partial peptide, or a salt thereof, or a membrane fraction of the cell, in the presence or absence of said ligand; the cell stimulating activities mediated by said protein, its partial peptide, or a salt thereof, are determined and compared;

[12] the screening method according to [11], wherein the protein comprising the same or substantially the same amino acid sequence as the amino acid sequence represented by SEQ ID NO: 1, its partial peptide, or a salt thereof, is a protein, its partial peptide, or a salt thereof, which is expressed on a cell membrane by culturing a transformant bearing a DNA encoding said protein, its partial peptide, or a salt thereof;

[13] the screening method according to [10] to [12], wherein the cell stimulating activity is a decrease or increase in intracellular cAMP level;

[14] a kit for screening a compound or its salt that alters the binding property of a protein comprising the same or substantially the same amino acid sequence as the amino acid sequence represented by SEQ ID NO: 1, or a salt thereof, to a ligand capable of specifically binding to said protein or a salt thereof, which comprises (a) said protein or a salt thereof, and (b) said ligand;

[14a] a compound or its salt, which is obtainable by using the screening method according to [1] or the screening kit according to [14];

[14b] the compound or its salt according to [14a], wherein the compound is a compound or its salt that inhibits the binding of a protein comprising the same or substantially the same amino acid sequence as the amino acid sequence represented by SEQ ID NO: 1, its partial peptide, or a salt thereof, to a ligand;

[14c] the compound or its salt according to [14b], which is an agonist;

[14d] the compound or its salt according to [14b], which is an antagonist;

[14e] a medicament comprising a compound or its salt that inhibits the binding of a protein comprising the same or substantially the same amino acid sequence as the amino acid sequence represented by SEQ ID NO: 1, its partial peptide, or a salt thereof, to a ligand;

[14f] an agent for the prevention/treatment of digestive tract (gastrointestinal) disorders or type II diabetes, which comprises the compound or its salt according to [14c];

[14g] an agent for the prevention/treatment of digestive cancer, immune disorders or obesity, which comprises the compound or its salt according to [14d];

[15] an agent for the prevention/treatment of digestive tract (gastrointestinal) disorders or type II diabetes, which comprises a compound or its salt that promotes the activity of a protein comprising the same or substantially the same amino acid sequence as the amino acid sequence represented by SEQ ID NO: 1, its partial peptide, or a salt thereof,

[16] an agent for the prevention/treatment of digestive cancer, immune disorders or obesity, which comprises a compound or its salt that inhibits the activity of a protein comprising the same or substantially the same amino acid sequence as the amino acid sequence represented by SEQ ID NO: 1, its partial peptide, or a salt thereof,

[17] a ligand capable of specifically binding to a protein comprising the same or substantially the same amino acid sequence as the amino acid sequence represented by SEQ ID NO: 1, or a salt thereof;

[18] a method of preventing/treating digestive tract (gastrointestinal) disorders or type II diabetes, which comprises promoting the activity of a protein comprising the same or substantially the same amino acid sequence as the amino acid sequence represented by SEQ ID NO: 1, its partial peptide, or a salt thereof;

[19] a method of preventing/treating digestive cancer, immune disorders or obesity, which comprises inhibiting the activity of a protein comprising the same or substantially the same amino acid sequence as the amino acid sequence represented by SEQ ID NO: 1, its partial peptide, or a salt thereof;

[20] a method of preventing/treating digestive tract (gastrointestinal) disorders or type II diabetes, which comprises administering to a mammal an effective dose of a compound or its salt that promotes the activity of a protein comprising the same or substantially the same amino acid sequence as the amino acid sequence represented by SEQ ID NO: 1, its partial peptide, or a salt thereof;

[21] a method of preventing/treating digestive cancer, immune disorders or obesity, which comprises administering to a mammal an effective dose of a compound or its salt that inhibits the activity of a protein comprising the same or substantially the same amino acid sequence as the amino acid sequence represented by SEQ ID NO: 1, its partial peptide, or a salt thereof;

[22] use of a compound or its salt that promotes the activity of a protein comprising the same or substantially the same amino acid sequence as the amino acid sequence represented by SEQ ID NO: 1, its partial peptide, or a salt thereof, to manufacture an agent for the prevention/treatment of digestive tract (gastrointestinal) disorders or type II diabetes;

[23] use of a compound or its salt that inhibits the activity of a protein comprising the same or substantially the same amino acid sequence as the amino acid sequence represented by SEQ ID NO: 1, its partial peptide, or a salt thereof, to manufacture an agent for the prevention/treatment of digestive cancer, immune disorders or obesity; and so on.

Hereinafter, the "protein comprising the same or substantially the same amino acid sequence as the amino acid sequence represented by SEQ ID NO: 1, its partial peptide, or a salt thereof" is sometimes briefly referred to as the "receptor of the present invention" or the "protein of the present invention." Also, the "ligand capable of specifically binding to the receptor of the present invention" is sometimes briefly referred to as the "ligand of the present invention."

Furthermore, the present invention provides the following features:

(i) a method of screening a compound that alters binding properties of the ligand of the present invention to the receptor of the present invention, which comprises assaying the GTPγS binding-promoting activities on a cell membrane fraction containing the receptor of the present invention, in the presence of labeled GTPγS, when the ligand of the present invention is brought in contact with the cell membrane fraction containing the receptor of the present invention, and when a test compound is brought in contact with the cell membrane fraction containing the receptor of the present invention in the presence or absence of the ligand of the present invention; and comparing the activities;

(ii) a method of screening a compound that alters binding properties of the ligand of the present invention to the receptor of the present invention, which comprises assaying intracellular cAMP production suppressing activities of a cell wherein the receptor of the present invention is expressed, in the presence of a substance for increasing the intracellular cAMP level, when the ligand of the present invention is brought in contact with a cell wherein the receptor of the present invention is expressed and when a test compound is brought in contact with said cell in the presence or absence of the ligand of the present invention; and comparing the activities;

(iii) a method of screening a compound that alters binding properties of the ligand of the present invention to the receptor of the present invention, which comprises assaying enzyme activities of a reporter gene protein in the presence of a substance for increasing the intracellular cAMP level, when the ligand of the present invention is brought in contact with a cAMP response element reporter gene (CRE-reporter gen) vector-transfected cell wherein the receptor of the present invention is expressed; and when a test compound is brought in contact with a CRE-reporter gene vector-transfected cell wherein the receptor of the present invention is expressed, in the presence or absence of the ligand of the present invention; and comparing the activities;

(iv) a method of screening a compound that alters binding properties of the ligand of the present invention to the receptor of the present invention, which comprises assaying arachidonic acid metabolite-releasing activities, when the ligand of the present invention is brought in contact with a cell containing labeled arachidonic acid wherein the receptor of the present invention is expressed and when a test compound is brought in contact with a cell containing labeled arachidonic acid wherein the receptor of the present invention is expressed, in the presence or absence of the ligand of the present invention; and comparing the activities;

(v) a method of screening a compound that alters the binding properties of the ligand of the present invention to the receptor of the present invention, which comprises assaying intracellular calcium level increasing activities, when the ligand of the present invention is brought in contact with a cell wherein the receptor of the present invention is expressed and when a test compound is brought in contact with a cell wherein the receptor of the present invention is expressed, in the presence or absence of the ligand of the present invention; and comparing the activities;

(vi) a method of screening a compound that alters the binding properties of the ligand of the present invention to the receptor of the present invention, which comprises assaying inositol triphosphate producing activities in the presence of labeled inositol, when the ligand of the present invention is brought in contact with a cell wherein the receptor of the present invention is expressed and when a test compound is brought in contact with a cell wherein the receptor of the present invention is expressed, in the presence or absence of the ligand of the present invention; and comparing the activities;

(vii) a method of screening a compound that alters the binding properties of the ligand of the present invention to the receptor of the present invention, which comprises assaying enzyme activities of a reporter gene protein, when the ligand of the present invention is brought in contact with a TPA response element reporter gene (TRE-reporter gene) vector-transfected cell wherein the receptor of the present invention is expressed and when a test compound is brought in contact with a TRE-reporter gene vector-transfected cell wherein the receptor of the present invention is expressed, in the presence or absence of the ligand of the present invention; and comparing the activities;

(viii) a method of screening a compound that alters the binding properties of the ligand of the present invention to the receptor of the present invention, which comprises assaying cell growth, when the ligand of the present invention is brought in contact with a cell wherein the receptor of the present invention is expressed and when a test compound is brought in contact with a cell wherein the receptor of the present invention is expressed, in the presence or absence of the ligand of the present invention; and comparing the cell growth;

(ix) a method of screening a compound that alters the binding properties of the ligand of the present invention to the receptor of the present invention, which comprises assaying efflux activities of labeled rubidium in the presence of labeled rubidium, when the ligand of the present invention is brought in contact with a cell wherein the receptor of the present invention is expressed and when a test compound is brought in contact with a cell wherein the receptor of the present invention is expressed, in the presence or absence of the ligand of the present invention; and comparing the activities;

(x) a method of screening a compound that alters the binding properties of the ligand of the present invention to the receptor of the present invention, which comprises assaying extracellular pH changes, when the ligand of the present invention is brought in contact with a cell wherein the receptor of the present invention is expressed and when a test compound is brought in contact with a cell wherein the receptor of the present invention is expressed, in the presence or absence of the ligand of the present invention; and comparing the changes;

(xi) a method of screening a compound that alters the binding properties of the ligand of the present invention to the receptor of the present invention, which comprises culturing in a histidine-deficient medium a histidine synthetic gene-transfected yeast wherein the receptor of the present invention is expressed; assaying growth of said yeast when the ligand of the present invention is brought in contact with the yeast and when a test compound is brought in contact with the yeast in the presence or absence of the ligand of the present invention; and comparing the growth;

(xii) a method of screening a compound that alters the binding properties of the ligand of the present invention to the receptor of the present invention, which comprises assaying changes in cell membrane potentials when the ligand of the present invention is brought in contact with *Xenopus laevis* oocytes wherein RNA of a gene for the receptor of the present invention is transfected and when a test compound is brought in contact with *Xenopus laevis* oocytes wherein RNA of a gene for the receptor of the present invention is transfected in the presence or absence of the ligand of the present invention, and comparing the changes; and so on.

BEST MODE FOR CARRYING OUT THE INVENTION

Figure 1:
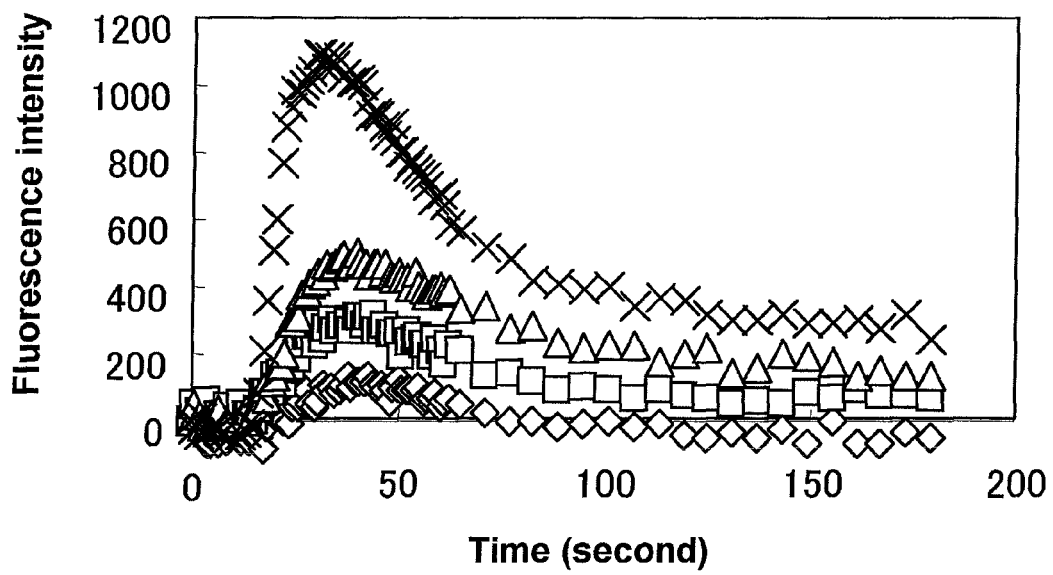
FIG. 1 shows the results of assaying changes in intracellular $Ca^{2+}$ levels when DNQX was added to CHO-K1 cells expressing GPR35 and Gα15. In the figure, the ordinate denotes fluorescence intensity showing the intracellular $Ca^{2+}$ level, the abscissa denotes time lapse (second) after the start of measurements and symbols ◇(open diamond), □(open square), △(open triangle) and X denote 0.3 μM DNQX, 1.0 μM DNQX, 3.0 μM DNQX and 10 μM DNQX, respectively.

The protein having the same or substantially the same amino acid sequence as the amino acid sequence represented by SEQ ID NO: 1 may be any protein derived from any cells (e.g., retinal cells, hepatocytes, splenocyte, nerve cells, glial cells, β cells of pancreas, bone marrow cells, mesangial cells, Langerhans' cells, epidermic cells, epithelial cells, endothelial cells, fibroblasts, fibrocytes, myocytes, fat cells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocytes or interstitial cells; or the corresponding precursor cells, stem cells, cancer cells, etc.) or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gall-bladder, bone marrow, adrenal gland, skin, muscle, lung, digestive tract (gastrointestinal) tracts (e.g., large intestine and small intestine), blood vessel, heart, thymus, spleen, submandibular gland, peripheral blood, prostate, testis, ovary, placenta, uterus, bone, joint, skeletal muscle, etc., or from blood cells or cultured cells thereof (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.) from human and other warm-blooded animals (e.g., guinea pigs, rats, mice, fowl, rabbits, swine, sheep, bovine, monkeys, etc.). The protein may also be a synthetic protein.

The amino acid sequence which is substantially the same amino acid sequence as the amino acid sequence represented by SEQ ID NO: 1 includes an amino acid sequence having at least about 70% homology, preferably at least about 80% homology, more preferably at least about 90% homology, to the amino acid sequence represented by SEQ ID NO: 1; and the like.

Homology of the amino acid sequences can be measured under the following conditions (an expectation value=10; gaps are allowed; matrix=BLOSUM62; filtering=OFF) using a homology scoring algorithm NCBI BLAST (National Center for Biotechnology Information Basic Local Alignment Search Tool).

Examples of the protein which has substantially the same amino acid sequence as the amino acid sequence represented by SEQ ID NO: 1 include a protein comprising substantially the same amino acid sequence as the amino acid sequence represented by SEQ ID NO: 1 and having an activity substantially equivalent to that of the amino acid sequence represented by SEQ ID NO: 1; and the like.

Examples of substantially the same amino acid sequence as the amino acid sequence represented by SEQ ID NO: 1 includes the amino acid sequence represented by SEQ ID NO: 7, the amino acid sequence represented by SEQ ID NO: 19, the amino acid sequence represented by SEQ ID NO: 21, the amino acid sequence represented by SEQ ID NO: 23, the amino acid sequence represented by SEQ ID NO: 27, and the like.

As the substantially equivalent activity, there is, for example, a ligand binding activity, a signal transduction activity, or the like. The substantially equivalent is used to mean that these activities are equivalent in terms of quality. Thus, the activities such as the ligand binding activity, signal transduction action and the like are preferably equivalent (e.g., about 0.01 to 100 times, preferably about 0.5 to 20 times, more preferably 0.5 to 2 times), but differences in quantitative factors such as a level of these activities, a molecular weight of the protein, etc. may be present and allowable.

The activities such as the ligand binding activity, signal transduction activity, etc. may be determined according to publicly known methods, for example, the methods for determining ligands or screening methods which will be later described.

The receptor of the present invention used also includes proteins comprising: (i) amino acid sequences wherein at least 1 or 2 (for example, approximately 1 to 100, preferably approximately 1 to 50, more preferably approximately 1 to 30, still more preferably approximately 1 to 10, and most preferably several (1 to 5)) amino acids in the amino acid sequence represented by SEQ ID NO: 1, SEQ ID NO: 7, SEQ ID NO: 19, SEQ ID NO: 21, SEQ ID NO: 23 or SEQ ID NO: 27 are deleted; (ii) amino acid sequences wherein at least 1 or 2 (for example, approximately 1 to 100, preferably approximately 1 to 50, more preferably approximately 1 to 30, still more preferably approximately 1 to 10, and most preferably several (1 to 5)) amino acids are added to the amino acid sequence represented by SEQ ID NO: 1, SEQ ID NO: 7, SEQ ID NO: 19, SEQ ID NO: 21, SEQ ID NO: 23 or SEQ ID NO: 27; (iii) amino acid sequences wherein at least 1 or 2 (for example, approximately 1 to 100, preferably approximately 1 to 50, more preferably approximately 1 to 30, still more preferably approximately 1 to 10, and most preferably several (1 to 5)) amino acids in the amino acid sequence represented by SEQ ID NO: 1, SEQ ID NO: 7, SEQ ID NO: 19, SEQ ID NO: 21, SEQ ID NO: 23 or SEQ ID NO: 27 are substituted by other amino acids; (iv) amino acid sequences wherein at least 1 or 2 (for example, approximately 1 to 100, preferably approximately 1 to 50, more preferably approximately 1 to 30, still more preferably approximately 1 to 10, and most preferably several (1 to 5)) amino acids in the amino acid sequence represented by SEQ ID NO: 1, SEQ ID NO: 7, SEQ ID NO: 19, SEQ ID NO: 21, SEQ ID NO: 23 or SEQ ID NO: 27 are inserted; or (v) amino acid sequences which are combination of these sequences; and the like.

Specific examples of the receptor of the present invention include a protein comprising the amino acid sequence represented by SEQ ID NO: 1, a protein comprising the amino acid sequence represented by SEQ ID NO: 7, a protein comprising the amino acid sequence represented by SEQ ID NO: 19, a protein comprising the amino acid sequence represented by SEQ ID NO: 21, a protein comprising the amino acid sequence represented by SEQ ID NO: 23, a protein comprising the amino acid sequence represented by SEQ ID NO: 27, and the like.

The partial peptide of the receptor of the present invention (hereinafter sometimes referred to as the partial peptide of the present invention) may be any partial peptide, so long as it can be employed for the screening methods for medicaments, etc. later described, and includes, for example, those having a site exposed outside cell membranes and retaining a substantially equivalent ligand binding activity, etc., among the protein molecules of the present invention.

An example of the partial peptide of the protein comprising the amino acid sequence represented by SEQ ID NO: 1, SEQ ID NO: 7, SEQ ID NO: 19, SEQ ID NO: 21, SEQ ID NO: 23 or SEQ ID NO: 27 is a peptide containing a domain which is analyzed to be an extracellular domain (hydrophilic site) in the hydrophobic plotting analysis. Also, a peptide containing a hydrophobic domain as a part of the peptide can be used as well. Moreover, a peptide, which independently contains each domain, can also be used but may also be a peptide of the part wherein multiple domains are contained at the same time.

The number of amino acids in the partial peptide of the present invention is at least 20 or more, preferably 50 or more and more preferably 100 or more in the amino acid sequence, which constitutes the protein of the present invention, and peptides having the amino acid sequence of such numbers of amino acids, etc. are preferred.

Herein, the term "substantially the same activity" has the same definition as described above. The "substantially the same activity" can be assayed in the manner described above.

The partial peptides of the present invention may be those (i) wherein at least 1 or 2 (preferably approximately 1 to 10, and more preferably several (1 to 5)) amino acids are deleted in the amino acid sequences described above, (ii) wherein at least 1 or 2 (preferably approximately 1 to 20, more preferably approximately 1 to 10 and most preferably several (1 to 5)) amino acids are added to the amino acid sequences described above, or (iii) wherein at least 1 or 2 (preferably approximately 1 to 10, more preferably several and most preferably approximately 1 to 5) amino acids in the amino acid sequences described above are substituted with other amino acids.

Specific examples of the partial peptide include a partial peptide comprising the 24th to 295th amino acid sequence in the amino acid sequence represented by SEQ ID NO: 1, a partial peptide comprising the 24th to 295th amino acid sequence in the amino acid sequence represented by SEQ ID NO: 7, the 55th to 326th amino acid sequence in the amino acid sequence represented by SEQ ID NO: 19, the 65th to 336th amino acid sequence in the amino acid sequence represented by SEQ ID NO: 21, a partial peptide comprising the 109th to 380th amino acid sequence in the amino acid sequence represented by SEQ ID NO: 23, a partial peptide comprising the 23rd to 294th amino acid sequence in the amino acid sequence represented by SEQ ID NO: 27, etc.

The receptor of the present invention and the partial peptide of the present invention are represented in a conventional manner of describing peptides, wherein the N terminus (amino end) is at the left hand and the C terminus (carboxyl end) is at the right hand. The C terminus may be carboxy (—COOH), carboxylate (—COO⁻), amide (—CONH$_2$) or ester (—COOR).

Herein, examples of the ester group represented by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; and the like. In addition, pivaloyloxymethyl or the like, which is used widely as an ester for oral administration, may also be used.

Where the receptor of the present invention and the partial peptide of the present invention contain a carboxyl group (or a carboxylate) at a position other than the C-terminus, it may be amidated or esterified and such an amide or ester is also included within the receptor of the present invention and the partial peptide of the present invention. The ester group in this case may be the same ester group as that described with respect to the above C-terminal group; etc.

Furthermore, examples of the receptor of the present invention and the partial peptide of the present invention include variants of the above proteins, wherein the amino group at the N-terminal methionine residue of the protein supra is protected with a protecting group (for example, a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as so-called glycoproteins having sugar chains bound thereto.

As the salts of the receptor of the present invention and the partial peptide of the present invention, salts with physiologically acceptable acids (e.g., inorganic acids, organic acids) or with bases (e.g., alkaline metal salts) are employed, and physiologically acceptable acid addition salts are particularly preferred. Examples of such salts are salts with inorganic acids (e.g., hydrochloric acid, phosphoric acid, hydrobromic acid or sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid), and the like.

Examples of the ligand capable of binding specifically to the receptor of the present invention (the ligand of the present invention) can be any ligand so long as the ligand binds specifically to the receptor of the present invention. Examples of the ligand are those having a dissociation constant in binding to the receptor of the present invention of 10 μM or less, preferably not greater than 2 μM, more preferably not greater than 1 μM, much more preferably not greater than 200 nM, and most preferably not greater than 100 nM, and the like.

The ligand of the present invention used includes, for example, a quinoxaline-2,3-dione compound, ellagic acid, etc.

The quinoxaline-2,3-dione compound can be any compound, as long as it has the quinoxaline-2,3-dione skeleton, and examples include 6,7-dinitroquinoxaline-2,3-dione, 6-nitro-7-sulfamoylbenzo[f]quinoxaline-2,3-dione, 6-cyano-7-nitroquinoxaline-2,3-dione, 5,7-dinitroquinoxaline-2,3-dione, etc., preferably 6,7-dinitroquinoxaline-2,3-dione, etc.

Labeled quinoxaline-2,3-dione compounds and labeled ellagic acid are also included within the ligand of the present invention.

Examples of labeling substances are radioisotopes (e.g., [$^3$H], [$^{125}$I], [$^{14}$C], [$^{32}$P], [$^{33}$P], [$^{35}$S], etc.), fluorescent substances (e.g., fluorescein, etc.), luminescent substances (e.g., luminol, etc.), enzymes (e.g., peroxidase, etc.), lanthanide elements, etc. Among them, radioisotopes are preferred.

The labeled ligand is preferably 6,7-dinitroquinoxaline-2, 3-dione, 6-nitro-7-sulfamoylbenzo[f]quinoxaline-2,3-dione, 6-cyano-7-nitroquinoxaline-2,3-dione, 5,7-dinitroquinoxaline-2,3-dione, etc., which are labeled with [$^3$H] or [$^{125}$I], respectively. Preferably, it is 6,7-Dinitroquinoxaline-2,3-dione labeled with [$^3$H] or [$^{125}$I].

The receptor of the present invention and the partial peptide of the present invention can be manufactured from the aforesaid human or warm-blooded animal cells or tissues by publicly known methods for purification of polypeptides, or can be manufactured by culturing transformants transformed by DNAs encoding the polypeptides. In addition, they can also be manufactured by modifications of peptide synthesis. For example, the receptor and partial peptide can also be manufactured by the methods described in, e.g., Genomics, 56, 12-21, 1999, Biochim. Biophys. Acta, 1446, 57-70, 1999, etc., or by modifications of these methods.

Where the receptor and the partial peptide are manufactured from human or mammalian tissues or cells, human or mammalian tissues or cells are homogenized, then extracted with an acid, etc., and the extract is isolated and purified by a combination of chromatography techniques such as reverse phase chromatography, ion exchange chromatography, and the like.

To synthesize the receptor or partial peptide of the present invention, or salts thereof, commercially available resins that are used for polypeptide synthesis can be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin and 4-(2',4'-dimethoxyphenyl-Fmoc-aminoethyl)phenoxy resin. Using these resins, amino acids in which α-amino groups and functional groups on the side chains are appropriately protected are condensed on the resin in the order of the sequence of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptide, receptor, partial peptide or amides thereof.

For condensation of the protected amino acids described above, a variety of activation reagents available for the polypeptide synthesis may be used, and carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents used to activate the protected amino acids or condense with the resin may be chosen from solvents that are known to be usable for polypeptide condensation reactions. For example, there may be employed acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxan, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole.

Examples of the protecting groups used to protect the starting amino groups include Z, Boc, t-pentyloxycarbonyl, isobornyloxycarbonyl, 4-methoxybenzyloxycarbonyl, ClZ, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group such as acetyl group, etc., an aroyl group such as benzoyl group, etc., a group derived from carbonic acid such as benzyloxycarbonyl group, ethoxycarbonyl group, etc.; and the like. Examples of a group suitable for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, tertiary butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)], etc. As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids, etc.; a treatment with a base such as diisopropylethylamine, triethylamine, piperidine or piperazine, etc.; reduction with sodium in liquid ammonia; or the like. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc., as well as by a treatment with an alkali such as a dilute sodium hydroxide solution and dilute ammonia, etc.

Protection of functional groups that should not be involved in the reaction of the starting materials, protecting groups, elimination of the protecting groups, activation of functional groups involved in the reaction, etc. may be appropriately selected from publicly known groups and publicly known means.

In another method for obtaining the receptor or partial peptide of the present invention, for example, the α-carboxyl group of the carboxy terminal amino acid is first protected by amidation; the peptide (polypeptide) chain is then extended from the amino group side to a desired length. Thereafter, a polypeptide in which only the protecting group of the N-terminal α-amino group has been eliminated from the peptide in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired receptor or its partial peptide.

To prepare the esterified form of the receptor or partial peptide of the present invention, or salts thereof, for example, the α-carboxyl group of the carboxy terminal amino acid is condensed with a desired alcohol to prepare the amino acid ester, followed by procedure similar to the preparation of the amides of the receptor or its partial peptide, to give the desired esters of the receptor or its partial peptide.

The receptor or partial peptide of the present invention can be manufactured by publicly known methods for peptide synthesis, or the partial peptide of the receptor of the present invention can be manufactured by cleaving the receptor with an appropriate peptidase. For the methods for peptide synthesis, for example, either solid phase synthesis or liquid phase synthesis may be used. That is, the partial peptide or amino acids that can construct the receptor or partial peptide of the present invention are condensed with the remaining part. Where the product contains protecting groups, these protecting groups are removed to give the desired peptide. Publicly known methods for condensation and elimination of the protecting groups are described in (i)-(v) below.

(i) M. Bodanszky & M. A. Ondetti: Peptide Synthesis, Interscience Publishers, New York (1966)

(ii) Schroeder & Luebke: The Peptide, Academic Press, New York (1965)

(iii) Nobuo Izumiya, et al.: *Peptide Gosei-no-Kiso to Jikken* (Basics and experiments of peptide synthesis), published by Maruzen Co. (1975)

(iv) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

(v) Haruaki Yajima ed.: *Zoku Iyakuhin no Kaihatsu* (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography, recrystallization, etc. to give the receptor or partial peptide of the present invention. When the receptor or partial peptide obtained by the above methods is in a free form, it can be converted into an appropriate salt by a publicly known method; conversely when the receptor or partial peptide is obtained in a salt form, it can be converted into the free form or in the form of a different salt by publicly known methods or modifications thereof.

The polynucleotide encoding the receptor or partial peptide of the present invention may be any polynucleotide, so long as it contains the base sequence encoding the receptor or partial peptide of the present invention described above, and preferably the polynucleotide is a DNA. Such a DNA may be any one of genomic DNA, genomic DNA library, cDNA derived from the cells or tissues described above, cDNA library derived from the cells/tissues described above and a synthetic DNA.

The vector to be used for the library may be any of bacteriophage, plasmid, cosmid, phagemid, and the like. In addition, the DNA can be amplified by reverse Transcriptase Polymerase Chain Reaction (hereinafter abbreviated as RT-PCR) with total RNA or mRNA fraction prepared from the cells or tissues described above.

The DNA encoding the receptor of the present invention may be any DNA, so long as it is, e.g., a DNA comprising the base sequence represented by SEQ ID NO: 2, SEQ ID NO: 8, SEQ ID NO: 20, SEQ ID NO: 22, SEQ ID NO: 24 or SEQ ID NO: 28; a DNA having a DNA hybridizable to a DNA comprising the base sequence represented by SEQ ID NO: 2, SEQ ID NO: 8, SEQ ID NO: 20, SEQ ID NO: 22, SEQ ID NO: 24 or SEQ ID NO: 28 under high stringent conditions and encoding a receptor which has an activity substantially equivalent to the activity of the protein comprising the amino acid sequence represented by SEQ ID NO: 1, SEQ ID NO:7, SEQ ID NO: 19, SEQ ID NO: 21, SEQ ID NO: 23 or SEQ ID NO: 27; and the like.

As the DNA hybridizable to a DNA comprising the base sequence represented by SEQ ID NO: 2, SEQ ID NO: 8, SEQ ID NO: 20, SEQ ID NO: 22, SEQ ID NO: 24 or SEQ ID NO: 28 under high stringent conditions, there may be employed a DNA containing the base sequence having at least about 70% homology, preferably at least about 80% homology, more preferably at least about 90% homology and most preferably at least about 95% homology, to the base sequence represented by SEQ ID NO: 2, SEQ ID NO: 8, SEQ ID NO: 20, SEQ ID NO: 22, SEQ ID NO: 24 or SEQ ID NO: 28, and the like.

The hybridization can be carried out by publicly known methods or by their modifications, for example, according to the method described in Molecular Cloning, 2nd. (J. Sambrook et al., Cold Spring Harbor Lab. Press, 1989), etc. When a commercially available library is used, hybridization may be carried out according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, the DNA encoding the receptor comprising the amino acid sequence represented by SEQ ID NO: 1 includes a DNA comprising the base sequence represented by SEQ ID NO:2; the DNA encoding the receptor comprising the amino acid sequence represented by SEQ ID NO:7 includes a DNA comprising the base sequence represented by SEQ ID NO:8; the DNA encoding the receptor comprising the amino acid sequence represented by SEQ ID NO: 19 includes a DNA comprising the base sequence represented by SEQ ID NO: 20; the DNA encoding the receptor comprising the amino acid sequence represented by SEQ ID NO: 21 includes a DNA comprising the base sequence represented by SEQ ID NO: 22; the DNA encoding the receptor comprising the amino acid sequence represented by SEQ ID NO: 23 includes a DNA comprising the base sequence represented by SEQ ID NO: 24, and, the DNA encoding the receptor containing the amino acid sequence represented by SEQ ID NO: 27 includes a DNA containing the base sequence represented by SEQ ID NO: 28.

As the DNA encoding the partial peptide of the present invention may be any DNA so long as it contains the base sequence encoding the partial peptide of the receptor of the present invention. The DNA may also be any one of genomic DNA, genomic DNA library, cDNA derived from the cells or tissues described above, cDNA library derived from the cells or tissues described above and synthetic DNA. Specifically as the DNA encoding the partial peptide of the present invention, there are employed, for example, a DNA having a part of the base sequence of a DNA having the base sequence represented by SEQ ID NO: 2, SEQ ID NO: 8, SEQ ID NO: 20, SEQ ID NO: 22, SEQ ID NO: 24 or SEQ ID NO: 28, a DNA having a base sequence hybridizable to the base sequence represented by SEQ ID NO: 2, SEQ ID NO: 8, SEQ ID NO: 20, SEQ ID NO: 22, SEQ ID NO: 24 or SEQ ID NO: 28 under high stringent conditions and containing a part of DNA encoding the receptor having the activities substantially equivalent to those of the protein containing the amino acid sequence represented by SEQ ID NO: 1, SEQ ID NO: 7, SEQ ID NO: 19, SEQ ID NO: 21, SEQ ID NO: 23 or SEQ ID NO: 27, and the like.

The DNA hybridizable to the base sequence represented by SEQ ID NO: 2, SEQ ID NO: 8, SEQ ID NO: 20, SEQ ID NO: 22, SEQ ID NO: 24 or SEQ ID NO: 28 is the same as described above.

Methods for the hybridization and the high stringent conditions that can be used are also the same as those described above.

The polynucleotide (e.g., DNA) encoding the receptor or partial peptide of the present invention may be labeled by methods public known. The labeling substances include radioisotopes, fluorescent substances (e.g., fluorescein, etc.), luminescent substances, enzymes, biotin, lanthanides, and the like.

For cloning of the DNA that completely encodes the receptor or partial peptide of the present invention, the DNA may be either amplified by PCR using synthetic DNA primers containing a part of the base sequence of the receptor or partial peptide of the present invention, or the DNA inserted into an appropriate vector can be selected by hybridization with a labeled DNA fragment or synthetic DNA that encodes a part or the entire region of the receptor or partial peptide of the present invention. The hybridization can be carried out, for example, according to the method described in Molecular Cloning, 2nd. (J. Sambrook et al., Cold Spring Harbor Lab. Press, 1989). Where commercially available library is used, the hybridization may also be performed in accordance with the protocol described in the attached instructions.

Conversion of the DNA base sequence can be effected by PCR or publicly known methods such as the ODA-LA PCR method, the Gapped duplex method, the Kunkel method, etc. or modifications thereof, by using publicly known kits available as Mutan™-super Express Km (Takara Shuzo Co., Ltd.) or Mutan™-K (Takara Shuzo Co., Ltd.), etc.

The cloned DNA encoding the receptor can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the receptor or partial peptide of the present invention can be manufactured, for example, by (a) excising the desired DNA fragment from the DNA encoding the receptor or partial peptide of the present invention, (b) and then ligating the DNA fragment with an appropriate expression vector downstream a promoter in the vector.

Examples of the vector include plasmids derived form $E.$ $coli$ (e.g., pBR322, pBR325, pUC12, pUC13), plasmids derived from $Bacillus$ $subtilis$ (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CM, pRc/RSV, pcDNAI/Neo, etc.

The promoter used in the present invention may be any promoter if it matches well with a host to be used for gene expression. In the case of using animal cells as the host, examples of the promoter include SRα promoter, SV40 promoter, HIV-LTR promoter, CMV promoter, HSV-TK promoter, etc.

Among them, CMV (cytomegarovirus) promoter, SRα promoter or the like is preferably used. Where the host is bacteria of the genus $Escherichia$, preferred examples of the promoter include trp promoter, lac promoter, recA promoter, λ$P_L$ promoter, lpp promoter, T7 promoter, etc. In the case of using bacteria of the genus $Bacillus$ as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin promoter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as $Amp^r$), neomycin resistant gene (hereinafter sometimes abbreviated as $Neo^r$, G418 resistance), etc. In particular, when dhfr gene is used as the selection marker together with CHO (dhfr⁻) cell, the objective gene may be selected also on thymidine free media.

If necessary, a signal sequence that matches with a host is added to the N-terminal side of the receptor of the present invention. Examples of the signal sequence that can be used are PhoA signal sequence, OmpA signal sequence, etc. in the case of using bacteria of the genus $Escherichia$ as the host; α-amylase signal sequence, subtilisin signal sequence, etc. in the case of using bacteria of the genus $Bacillus$ as the host; MFα signal sequence, SUC2 signal sequence, etc. in the case of using yeast as the host; and insulin signal sequence, α-interferon signal sequence, antibody molecule signal sequence, etc., in the case of using animal cells as the host, respectively.

Using the vector containing the DNA encoding the receptor or partial peptide of the present invention thus constructed, transformants can be manufactured.

Examples of the host, which may be employed, are bacteria belonging to the genus $Escherichia$, bacteria belonging to the genus $Bacillus$, yeast, insect cells, insects, animal cells, and the like.

Specific examples of the bacteria belonging to the genus *Escherichia* include *Escherichia coli* K12 DH1 [Proc. Natl. Acad. Sci. U.S.A., 60, 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207-21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of *Trichoplusia ni*, High Five™ cell derived from egg of *Trichoplusia ni*, cells derived from *Mamestra brassicae*, cells derived from *Estigmena acrea*, etc.; and for the virus BmNPV, *Bombyx mori* N cell (BmN cell), etc. is used. Examples of the Sf cell which can be used are Sf9 cell (ATCC CRL1711) and Sf21 cell (both cells are described in Vaughn, J. L. et al., In vivo, 13, 213-217 (1977), etc.

As the insect, for example, a larva of *Bombyx mori*, etc. can be used (Maeda et al., Nature, 315, 592 (1985)).

Examples of animal cells include monkey cell COS-7, Vero, Chinese hamster cell CHO (hereinafter abbreviated as CHO cell), dhfr gene deficient Chinese hamster cell CHO (hereinafter abbreviated as CHO (dhfr⁻) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182-187 (1991), Proc. Natl. Acad. Sci. U.S.A., 75, 1929 (1978), etc.

Insect cells or insects can be transformed, for example, according to the method described in Bio/Technology, 6, 47-55 (1988), etc.

Animal cells can be transformed, for example, according to the method described in *Saibo Kogaku* (Cell Engineering), extra issue 8, *Shin Saibo Kogaku Jikken Protocol* (New Cell Engineering Experimental Protocol), 263-267 (1995), published by Shujunsha, or Virology, 52, 456 (1973).

Thus, the transformant transformed with the expression vector containing the DNA encoding the receptor or partial peptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc. Examples of the nitrogen sources include inorganic or organic materials such as ammonium salts, nitrate salts, corn steep liquor, peptone, casein, meat extract, soybean cake, potato extract, etc. Examples of the inorganic materials are calcium chloride, sodium dihydrogenphosphate, magnesium chloride, etc. In addition, yeast extracts, vitamins, growth promoting factors, etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431-433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at approximately 15 to 43° C. for approximately 3 hours to 24 hours. If necessary, the culture may further be aerated or agitated.

Where the bacteria belonging to the genus *Bacillus* are used as the host, the transformant is cultivated generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 to 5 days and, if necessary, the culture may be aerated or agitated.

Where animal cells are employed as the host, the transformant is cultivated in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30 to 40° C. for about 15 to 60 hours and, if necessary, the culture may be aerated or agitated.

As described above, the receptor or partial peptide of the present invention can be produced in the cell, cell membrane or outside of the transformant, etc.

The receptor or partial peptide of the present invention can be separated and purified from the culture described above by the following procedures.

When the receptor or partial peptide of the present invention is extracted from the culture or cells, after cultivation, the transformant or cell is collected by a publicly known method and suspended in an appropriate buffer. The transformant or cell is then disrupted by publicly known methods such as ultrasonication, a treatment with lysozyme and/or freeze-thaw cycling, followed by centrifugation or filtration, or the like. Thus, the crude extract of the polypeptide can be obtained. The buffer used for the procedures may contain a protein modifier such as urea or guanidine hydrochloride, or a surfactant such as Triton X-100™, etc. When the polypeptide is secreted in the culture broth, after completion of the cultivation the supernatant can be separated from the transformant or cell by a publicly known method to collect the supernatant.

The receptor or partial peptide contained in the supernatant or extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis, etc.; and the like.

When the receptor or partial peptide thus obtained is in a free form, it can be converted into the salt by publicly known methods or modifications thereof. On the other hand, when the receptor or partial peptide is obtained in the form of a salt, it can be converted into the free form or in the form of a different salt by publicly known methods or modifications thereof.

The receptor or partial peptide produced by the recombinant can be treated, prior to or after the purification, with an appropriate protein modifying enzyme so that the receptor or partial peptide can be appropriately modified to partially remove a polypeptide. Examples of the protein-modifying enzyme include trypsin, chymotrypsin, arginyl endopeptidase, protein kinase, glycosidase, and the like.

The ligand capable of specifically binding to the receptor of the present invention can be used as it is when commercially available, or can be extracted or manufactured by publicly known methods or modifications thereof.

The antibodies to the protein comprising the same or substantially the same amino acid sequence as the amino acid sequence represented by SEQ ID NO: 1, its partial peptide or salts thereof (hereinafter sometimes collectively referred to as the antibody of the present invention) may be any of polyclonal and monoclonal antibodies, as long as they are antibodies capable of recognizing antibodies to the receptor of the present invention. The antibodies to the receptor of the present invention include antibodies that inactivate the signal transduction of the receptor, antibodies that activate the signal transduction of the receptor, and the like.

The antibodies to the receptor of the present invention can be manufactured according to publicly known methods for producing antibodies or antisera, using the receptor of the present invention as antigens.

[Preparation of Monoclonal Antibody]

(a) Preparation of Monoclonal Antibody-Producing Cell

The receptor of the present invention is administered to a warm-blooded animal, either solely or together with carriers or diluents to the site that can produce the antibody by the administration to warm-blooded animal. In order to potentiate the antibody productivity upon the administration, complete Freund's adjuvant or incomplete Freund's adjuvant may be administered. The administration is effected usually once every 2 to 6 weeks and approximately 2 to 10 times in total. The mammals to be used include monkey, rabbit, dog, guinea pig, mouse, rat, sheep, goat and fowl, with mouse and rat being preferably used.

In the preparation of the monoclonal antibody-producing cells, an animal wherein the antibody titer is noted is selected from warm-blooded animals immunized with antigens, e.g., mice, then spleen or lymph node is collected after two to five days from the final immunization and the antibody-producing cells contained therein are fused with myeloma cells to give monoclonal antibody-producing hybridomas. The antibody titer in antisera may be determined, for example, by reacting the labeled polypeptide, which will be described later, with the antiserum followed by measuring the binding activity of the labeling agent bound to the antibody. The fusion may be carried out, for example, according to the method for Koehler and Milstein (Nature, 256, 495, 1975). Examples of the fusion accelerator are polyethylene glycol (PEG), Sendai virus, etc. and PEG is preferably used.

Examples of myeloma cells include myeloma cells from warm-blooded animals such as NS-1, P3U1, SP2/0, AP-1, etc. with P3U1 being preferably used. The ratio of the number of the antibody-producing cells (spleen cells) to the number of myeloma cells to be used is preferably about 1:1 to about 20:1 and PEG (preferably PEG 1000 to PEG 6000) is added in a concentration of about 10 to 80%. The cell fusion can be efficiently carried out by incubating both cells at about 20 to 40° C., preferably about 30 to 37° C. for about 1 to 10 minutes.

Various methods can be used for screening of a monoclonal antibody-producing hybridoma. Examples of such a method include a method which comprises adding the supernatant of hybridoma to a solid phase (e.g., microplate) adsorbed with the polypeptide (protein) as antigen directly or together with a carrier, adding an anti-immunoglobulin antibody (where mouse cells are used for the cell fusion, anti-mouse immunoglobulin antibody is used) labeled with a radioactive substance, an enzyme, etc., or Protein A, and detecting the monoclonal antibody bound to the solid phase, a method which comprises adding the supernatant of hybridoma to a solid phase adsorbed with an anti-immunoglobulin antibody or Protein A, adding the polypeptide labeled with a radioactive substance or an enzyme and detecting the monoclonal antibody bound to the solid phase; and the like.

The monoclonal antibody can be selected according to publicly known methods or their modifications. In general, the selection can be effected in a medium for animal cells supplemented with HAT (hypoxanthine, aminopterin and thymidine). Any selection and growth medium can be employed as far as the hybridoma can grow therein. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.), etc. can be used for the selection and growth medium. The cultivation is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the determination of antibody titer in antisera described above.

(b) Purification of Monoclonal Antibody

Separation and purification of a monoclonal antibody can be carried out according the same manner as applied to conventional separation and purification for polyclonal antibodies, such as separation and purification of immunoglobulins [e.g., salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G, etc. and dissociating the binding to obtain the antibody].

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or with a complex formed from immunogen and a carrier protein in a manner similar to the method for manufacturing monoclonal antibodies described above. The product containing the antibody to the receptor of the present invention is collected from the immunized animal followed by separation and purification of the antibody.

In the complex of immunogen and carrier protein for immunizing warm-blooded animals, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin, keyhole limpet hemocyanin, etc. is coupled to hapten in a carrier-to-hapten weight ratio of approximately 0.1 to 20, preferably approximately 1 to 5.

A variety of condensation agents can be used for the coupling of carrier to hapten. Glutaraldehyde, carbodiimide, maleimide activated ester and activated ester reagents containing thiol group or dithiopyridyl group, etc. are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually carried out approximately once every 2 to 6 weeks and approximately 3 to 10 times in total.

The polyclonal antibody can be collected from the blood, ascites, etc., preferably from blood of the warm-blooded mammals immunized by the method described above.

The polyclonal antibody titer in antiserum can be determined by the same procedure as in the measurement of antibody titer in antisera described above. The polyclonal antibody can be separated and purified according to the same procedure for separation and purification of immunoglobulins as used for the monoclonal antibody described above.

The polynucleotide (e.g., DNA) containing a complementary or substantially complementary base sequence to the polynucleotide (e.g., DNA) or a part thereof encoding the protein comprising the same or substantially the same amino acid sequences as the amino acid sequence represented by SEQ ID NO: 1, its partial peptide or its salt can be any polynucleotide (antisense polynucleotide), so long as it contains a base sequence complementary or substantially complementary to the polynucleotide, or a part of the base sequence and capable of suppressing the expression of the polynucleotide.

Specific examples of the polynucleotide include antisense DNAs (hereinafter these DNAs are sometimes simply referred to as the antisense DNA of the present invention) having base sequences complementary or substantially complementary to polynucleotides (e.g., DNAs) (hereinafter these DNAs are sometimes briefly referred to as the DNA of the present invention) encoding the receptor of the present invention or a part of the base sequence, and can be any antisense DNA, so long as they contain the complementary or substantially complementary base sequence to the DNA of the present invention, or a part of the base sequence and capable of suppressing the expression of the DNA.

The base sequence substantially complementary to the DNA of the present invention includes, for example, a base sequence having at least about 70% homology, preferably at least about 80% homology, more preferably at least about 90% homology and most preferably at least about 95% homology, to the entire base sequence or partial base sequence of the base sequence complementary to the DNA of the present invention (i.e., a complementary strand to the DNA of the present invention). In the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the receptor of the present invention (e.g., the base sequence around the initiation codon, etc.). These antisense DNAs can be synthesized using publicly known DNA synthesizers, etc.

Specific examples include an antisense polynucleotide having the entire or part of a base sequence complementary or substantially complementary to a base sequence of DNA having the base sequence represented by SEQ ID NO: 2, SEQ ID NO: 8, SEQ ID NO: 20, SEQ ID NO: 22, SEQ ID NO: 24 or SEQ ID NO: 28, an antisense DNA comprising the entire or part of a base sequence complementary or substantially complementary to a base sequence of DNA having the base sequence represented by SEQ ID NO: 2, SEQ ID NO: 8, SEQ ID NO: 20, SEQ ID NO: 22, SEQ ID NO: 24 or SEQ ID NO: 28, and the like, preferably an antisense polynucleotide comprising the entire or part of a base sequence complementary to a base sequence of DNA having the base sequence represented by SEQ ID NO: 2, SEQ ID NO: 8, SEQ ID NO: 20, SEQ ID NO: 22, SEQ ID NO: 24 or SEQ ID NO: 28, an antisense DNA comprising the entire or part of a base sequence complementary to a base sequence of DNA having the base sequence represented by SEQ ID NO: 2, SEQ ID NO: 8, SEQ ID NO: 20, SEQ ID NO: 22, SEQ ID NO: 24 or SEQ ID NO: 28, and the like.

The antisense polynucleotide is generally constructed by bases of about 10 to about 40, preferably about 15 to about 30.

To prevent digestion with a hydrolase such as nuclease, etc., the phosphoric acid residue (phosphate) of each nucleotide that constructs the antisense DNA may be substituted with chemically modified phosphoric acid residues, e.g., phosphorothioate, methyl phosphonate, phosphorodithionate, etc. These antisense polynucleotides may be synthesized using publicly known DNA synthesizers, etc.

According to the present invention, the antisense polynucleotides (nucleic acids) that can inhibit the replication or expression of a gene for the receptor of the present invention can be designed and synthesized based on the cloned or determined base sequence information of the DNA encoding the receptor. Such polynucleotides (nucleic acids) can hybridize to the RNA of a gene for the receptor of the present invention and inhibit the RNA synthesis or the function of RNA, or can regulate/control the expression of a gene for the receptor of the present invention via the interaction with RNAs associated with the receptor of the present invention. Polynucleotides complementary to the specified sequences of RNA associated with the receptor of the present invention and polynucleotides that can specifically hybridize to RNA associated with the receptor of the present invention are useful for regulating and controlling the expression of a gene for the receptor of the present invention in vivo and in vitro. These polynucleotides are useful for the treatment or diagnosis of diseases, etc. The term "correspond" is used to refer to homologous or complementary to a specific sequence of nucleotides, base sequences or nucleic acids including the gene. As between nucleotides, base sequences or nucleic acids and peptides (proteins), the term "corresponding" usually refers to amino acids of a peptide (protein) that is instructed to be derived from the sequence of nucleotides (nucleic acids) or its complements. The 5' end hairpin loop, 5' end 6-base-pair repeats, 5' end untranslated region, protein translation initiation codon, protein coding region, ORF translation initiation codon, 3' untranslated region, 3' end palindrome region, and 3' end hairpin loop of the protein gene may be selected as preferred target regions, though any region may be a target within the protein genes.

The relationship between the targeted nucleic acids and the polynucleotides complementary to at least a portion of the target, specifically the relationship between the target and the polynucleotides hybridizable to the target, is denoted to be "antisense". The antisense polynucleotides may be polydeoxynucleotides containing 2-deoxy-D-ribose, polydeoxynucleotides containing D-ribose, any other type of polynucleotides which are N-glycosides of a purine or pyrimidine base, or other polymers containing non-nucleotide backbones (e.g., protein nucleic acids and synthetic sequence-specific nucleic acid polymers commercially available) or other polymers containing nonstandard linkages (provided that the polymers contain nucleotides with such a configuration that allows base pairing or base stacking, as is found in DNA and RNA). The antisense polynucleotides may be double-stranded DNA, single-stranded DNA, double-stranded RNA, single-stranded RNA or a DNA:RNA hybrid, and further includes unmodified polynucleotides (or unmodified oligonucleotides), those with publicly known types of modifications, for example, those with labels known in the art, those with caps, methylated polynucleotides, those with substitution of one or more of naturally occurring nucleotides with their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (including nucleases, nuclease inhibitors, toxins, antibodies, signal peptides, poly-L-lysine, etc.) and saccharides (e.g., monosaccharides, etc.), those with intercalators (e.g., acridine, psoralen, etc.), those containing chelators (e.g., metals, radioactive metals, boron, oxidative metals, etc.) and those containing alkylating agents, those with modified linkages (e.g., α anomeric nucleic acids, etc.). Herein the terms "nucleoside", "nucleotide" and "nucleic acid" are used to refer to moieties that contain not only the purine and pyrimidine bases, but also other heterocyclic bases, which have been modified. Such modifications include methylated purines and pyrimidines, acylated purines and pyrimidines and other heterocyclic rings. Modified nucleosides or nucleotides also include modifications on the sugar moiety, for example, wherein one or more hydroxyl groups may optionally be replaced with a halogen, aliphatic groups, or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfurized and thiophosphate derivatives of nucleic acids and those resistant to degradation of polynucleoside or oligonucleoside amides. The antisense nucleotides of the present invention can be modified preferably based on the following design, that is, by increasing the intracellular stability of the antisense nucleotide, increasing the cellular permeability of the antisense nucleotide, increasing the affinity to the target sense strand to a higher level, or minimizing the toxicity of the antisense nucleotide, if any.

Many such modifications are known in the art, as disclosed in J. Kawakami et al., Pharm. Tech. Japan, Vol. 8, pp. 247, 1992; Vol. 8, pp. 395, 1992; S. T. Crooke et al. ed., Antisense Research and Applications, CRC Press, 1993; etc.

The antisense polynucleotide acid of the present invention may contain altered or modified sugars, bases or linkages. The antisense polynucleotide may also be provided in a specialized form such as liposomes, microspheres or may be applied to gene therapy or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached at the 3' or 5' ends of the nucleic acid and may be also attached through a base, sugar, or intramolecular nucleoside linkage. Other moieties may be capping groups specifically placed at the 3' or 5' ends of the nucleic acid to prevent degradation by nuclease such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleotide can be examined using the transformant of the present invention, the gene expression system of the present invention in vivo and in vitro, or the translation system of the receptor of the present invention in vivo and in vitro. The nucleic acid can be applied to cells by a variety of publicly known methods.

Hereinafter, (i) the receptor of the present invention, (ii) the polynucleotide encoding the receptor of the present invention (the polynucleotide of the present invention), (iii) the antibody to the receptor of the present invention (the antibody of the present invention) (iv) the antisense polynucleotide (e.g., DNA) of the receptor of the present invention (e.g., the antisense DNA of the present invention), (v) the ligand capable of specifically binding to the receptor of the present invention (the ligand of the present invention), etc. are described in terms of their applications.

[1] Screening of Drug Candidate Compound for Disease

The ligand of the present invention has a digestive tract (gastrointestinal) function modulating activity, an intestinal cell growth modulating activity, etc.

By using the receptor of the present invention or the ligand-receptor assay system using the expression system of the receptor of the present invention in its recombinant form, compounds (e.g., peptides, proteins, antibodies, non-peptide compounds, synthetic compounds, fermentation products, cell extracts, plant extract, animal tissue extracts, blood plasma, etc.) or salts thereof that alter the binding properties of the receptor of the present invention to the ligand of the present invention can be efficiently screened.

The compounds or salts thereof include (i) compounds having the cell stimulating activities (for example, the activities that promote arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of microtubule-associated protein kinase (MAP kinase), receptor internalization activity, etc.) mediated by the receptor of the present invention (agonists), (ii) compounds that do not have the cell-stimulating activities (antagonists), (iii) compounds that promote the binding affinity of the receptor of the present invention to the ligand of the present invention, (iv) compounds that inhibit the binding affinity of the receptor of the present invention to the ligand of the present invention, and the like.

Specifically, comparison is made between (i) when the ligand of the present invention is brought in contact with the receptor of the present invention and (ii) when the ligand of the present invention and a test compound are brought in contact with the receptor of the present invention. The comparison is made, for example, by assaying the binding levels of the ligand of the present invention and the receptor of the present invention, the cell stimulating activities, or the like.

Specific examples of the screening method of the present invention include:

(a) a method of screening a compound or its salt that alters the binding properties of the ligand of the present invention and the receptor of the present invention, which comprises measuring binding amounts of the ligand of the present invention and the receptor of the present invention when the ligand of the present invention is brought in contact with the receptor of the present invention and when the ligand of the present invention and a test compound are brought in contact with the receptor of the present invention; and comparing the binding amounts;

(b) a method of screening a compound or its salt that alters the binding amounts of the ligand of the present invention and the receptor of the present invention, which comprises measuring binding amounts of the ligand of the present invention and a cell containing the receptor of the present invention or a membrane fraction of the cell, when the ligand of the present invention is brought in contact with the cell containing the receptor of the present invention or the membrane fraction of the cell and when the ligand of the present invention and a test compound are brought in contact with the cell or a membrane fraction of the cell, and comparing the binding amounts; and, (c) the screening method according to (b) described above, wherein the receptor of the present invention is the receptor of the present invention expressed on a cell membrane by culturing a transformant having a DNA encoding the receptor of the present invention;

(d) the receptor-binding assay system such as the screening method described in (a) to (c) above, wherein the ligand of the present invention is a labeled ligand;

(e) a method of screening a compound or its salt that alters the binding properties of the ligand of the present invention and the receptor of the present invention, which comprises assaying cell stimulating activities mediated by the receptor of the present invention, when the ligand of the present invention is brought in contact with the receptor of the present invention and when the ligand of the present invention and a test compound are brought in contact with the receptor of the present invention; and comparing the activities;

(f) a method of screening a compound or its salt that alters the binding properties of the ligand of the present invention and the receptor of the present invention, which comprises assaying the cell stimulating activities mediated by the receptor of the present invention, when the ligand of the present invention is brought in contact with a cell containing the receptor of the present invention or a membrane fraction of the cell, and when the ligand of the present invention and a test compound are brought in contact with the cell containing the receptor of the present invention or a membrane fraction of the cell; and comparing the activities; and, (g) the screening method according to (f) described above, wherein the receptor of the present invention is the receptor of the present invention expressed on a cell membrane by culturing a transformant containing a DNA encoding the receptor of the present invention; and the like.

The screening method of the present invention will be specifically described below.

As the receptor of the present invention, membrane fractions from human or warm-blooded animal organs are preferably employed. However, it is very difficult to obtain human-derived organs among others, and the receptor of the present invention, etc. expressed abundantly using recombinants are suitable for use in the screening.

To produce the receptor of the present invention, the aforesaid methods of the receptor of the present invention, etc. are applied.

When cells containing the receptor of the present invention, membrane fractions of these cells, or the like are employed in the screening method of the present invention, these cells or membrane fractions may be prepared following the procedures later described.

Where cells containing the receptor of the present invention are employed, the cells may be fixed using glutaraldehyde, formalin, etc. The fixation can be made by publicly known methods.

The cells containing the receptor of the present invention refer to host cells where the receptor of the present invention is expressed, and such host cells include *Escherichia coli*, *Bacillus subtilis*, yeast, insect cells, animal cells, etc. described above. The host cells can be prepared in a manner similar to the method described above.

The cell membrane fraction is used to mean a fraction abundant in cell membrane obtained by cell disruption and subsequent fractionation by publicly known methods. The cell disruption methods include cell squashing using a Potter-Elvehjem homogenizer, disruption using a Waring blender or Polytron (manufactured by Kinematica Inc.), disruption by ultrasonication, disruption by cell spraying through thin nozzles under an increased pressure using a French press, and the like. Cell membrane fractionation is effected mainly by fractionation using a centrifugal force, such as fractional centrifugation, density gradient centrifugation, etc. For example, cell disruption fluid is centrifuged at a low speed (500 rpm to 3,000 rpm) for a short period of time (normally about 1 to about 10 minutes), the resulting supernatant is then centrifuged at a higher speed (15,000 rpm to 30,000 rpm) normally for 30 minutes to 2 hours. The precipitate thus obtained is used as the membrane fraction. The membrane fraction is rich in the receptor of the present invention expressed and membrane components such as cell-derived phospholipids, membrane proteins, etc.

The amount of the receptor of the present invention in the cells or cell membrane fractions containing the receptor of the present invention is preferably $10^3$ to $10^8$ molecules, more preferably $10^5$ to $10^7$ molecules, per cell. As the amount of expression increases, the ligand binding activity per unit of the membrane fraction (specific activity) increases so that not only the highly sensitive screening system can be constructed but also large quantities of samples can be assayed on the same lot.

To perform the screening methods such as the receptor-binding assay system, the cell stimulating assay system and the like, for example, a fraction of the receptor of the present invention and a labeled form of the ligand of the present invention (e.g., a labeled form of the ligand of the present invention), etc. are employed. For the fraction of the receptor of the present invention, a fraction from naturally occurring type of the receptor of the present invention or a fraction from recombinant type of the receptor of the present invention having an activity equivalent thereto, or the like, are desirable. Herein, the equivalent activity is used to mean an equivalent ligand binding activity, etc.

As the labeled ligands, there may be used ligands labeled with, e.g., radioisotope (e.g., $[^3H]$, $[^{125}I]$, $[^{14}C]$, $[^{32}P]$, $[^{33}P]$, $[^{35}S]$, etc.), fluorescent substances (e.g., fluorescein, etc.), luminescent substances (e.g., luminol, etc.), enzymes (e.g., peroxidase, etc.), lanthanide elements, or the like.

Specifically, screening of the compound that alters the binding properties of the ligand of the present invention to the receptor of the present invention can be performed by the following procedures. First, a receptor preparation is prepared by suspending cells containing the receptor of the present invention or their membrane fractions in a buffer appropriate for screening. Any buffer can be used so long as it does not interfere with ligand-receptor binding, such buffer including a phosphate buffer, a Tris-HCl buffer, etc. having pH of 4 to 10 (desirably pH of 6 to 8). For the purpose of minimizing non-specific binding, a surfactant such as CHAPS, Tween-80™ (manufactured by Kao-Atlas Inc.), digitonin, deoxycholate, etc. may be added to the buffer. Further for the purpose of suppressing degradation of the receptor of the present invention by a protease, a protease inhibitor such as PMSF, leupeptin, E-64 (manufactured by Peptide Institute, Inc.), pepstatin, etc. may also be added. A given quantity (5,000 cpm to 500,000 cpm) of a labeled form of the ligand of the present invention is added to 0.01 ml to 10 ml of the receptor solution, and at the same time, $10^{-10}$ to $10^{-7}$ μM of a test compound is allowed to be co-present. To determine the amount of non-specific binding (NSB), a reaction tube containing a large excess of the ligand of the present invention in an unlabeled form is also provided. The reaction is carried out at 0° C. to 50° C., preferably about 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity in the glass fiber filter paper is then measured by means of a liquid scintillation counter or a γ-counter. When the nonspecific binding (NSB) is subtracted from the count ($B_0$) when any antagonizing compound is absent and the thus obtained count ($B_0$—NSB) is made 100%, a test compound having the specific binding (B—NSB) of, e.g., 50% or less, can be selected as a candidate substance capable of antagonistic inhibition.

In addition, the compounds which bind to the receptor of the present invention can also be screened by utilizing the surface plasmon sensor technique.

Specifically, the receptor of the present invention is immobilized on the sensor chip surface of Biacore 3000 (Biacore, Inc.), and then the solution of a test compound in phosphate-buffered saline (PBS), etc. is applied onto the chip surface. By monitoring the changes on the surface plasmon, the test compound bound to the receptor of the present invention is screened. For example, the test compound, which gives the measurement data of 5 resonance units or more in the changes at the surface plasmon, is selected as a substance having the binding properties to the receptor of the present invention.

To perform the screening methods of the cell stimulating assay system described above, the cell-stimulating activities mediated by the receptor of the present invention (e.g., the activity that promotes or suppresses arachidonic acid release, acetylcholine release, intracellular $Ca^{2+}$ release, intracellular cAMP production, intracellular cAMP production suppression, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase or activation of microtubule-associated protein kinase (MAP kinase), or receptor internalization activity, etc.) may be assayed by publicly known methods, or using assay kits commercially available. Specifically, the cells containing the receptor of the present invention are first cultured on a multi-well plate, etc. Prior to screening, the medium is replaced with a fresh medium or with an appropriate non-cytotoxic buffer, and a test compound or the like is added thereto, followed by culturing for a given period of time. Subsequently, the cells are extracted or the supernatant is recovered and the resulting product is quantified by the respective methods. Where it is difficult to detect the production of an indicator substance for the cell stimulating activities (e.g., arachidonic acid, etc.) due to a degrading enzyme contained in the cells, an inhibitor against such a degrading enzyme may be added prior to the assay. For detecting activities such as the cAMP production suppressing activity, the baseline production in the cells is increased by forskolin or the like and the suppressing effect on the increased baseline production can be detected.

To perform the screening by assaying the cell stimulating activities, appropriate cells in which the receptor of the present invention is expressed are required. As the cells where the receptor of the present invention is expressed, the aforesaid cell line in which the receptor of the present invention is expressed, etc. are desirable.

Examples of the test compound include peptides, proteins, antibodies, non-peptide compounds, synthetic compounds, fermentation products, cell extracts, plant extracts, animal tissue extracts, and the like. These compounds may be novel or known compounds. The test compounds may form salts and as salts of the test compounds, there are, for example, metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Among these salts, preferred are pharmaceutically acceptable salts. Where the compounds have, for example, acidic functional groups in the compound, the salts include inorganic salts such as alkali metal salts (e.g., sodium salts, potassium salts, etc.), alkaline earth metal salts (e.g., calcium salts, magnesium salts, barium salts, etc.), etc.; ammonium salts, etc.; and where the compounds have basic functional groups in the compound, the salts include salts with inorganic acids such as hydrobromic acid, nitric acid, sulfuric acid, phosphoric acid, etc., or salts with organic acids such as acetic acid, phthalic acid, fumaric acid, oxalic acid, tartaric acid, maleic acid, citric acid, succinic acid, methanesulfonic acid, p-toluenesulfonic acid, etc.

In more detail, the screening methods of the cell stimulating assay system described above are described in (1) to (12) below.

(1) When the receptor-expressed cells are stimulated by a receptor agonist, G protein in the cells is activated and GTP is bound thereto. This phenomenon is observed as well in a membrane fraction of the receptor-expression cells. Usually, GTP is hydrolyzed and changes to GDP. When GTPγS is previously added to the reaction solution, GTPγS is bound to G protein as in GTP, but is not hydrolyzed so that the state of GTPγS bound to the G protein-containing cell membrane is maintained. When labeled GTPγS is used, the labeled GTPγS remained on the cell membrane is measured, whereby the stimulating activity of the receptor agonist in the receptor-expressed cells can be assayed.

Utilizing this reaction, the compound that alters the binding properties of the ligand of the present invention to the receptor of the present invention can be screened by assaying the stimulating activities of the ligand of the present invention on the cells where the receptor of the present invention is expressed.

This method is carried out using the membrane fraction containing the receptor of the present invention. In this assay method, the substance showing the activity of promoting the binding of GTPγS to the membrane fraction containing the receptor of the present invention is an agonist.

Specifically, the compound that alters the binding properties of the ligand of the present invention to the receptor of the present invention can be screened by assaying the GTPγS binding promoting activities on the membrane fraction containing the receptor of the present invention in the presence of labeled GTPγS, when the ligand of the present invention is brought in contact with the membrane fraction containing the receptor of the present invention and when the ligand of the present invention and a test compound are brought in contact with the membrane fraction containing the receptor of the present invention; and comparing the activities.

According to this method, the test compound showing the activity of suppressing the GTPγS binding promoting activity by the ligand of the present invention against the membrane fraction containing the receptor of the present invention can be selected as a candidate substance capable of antagonistic inhibition.

On the other hand, an agonist can be screened as well by contacting a test compound alone with the membrane fraction containing the receptor of the present invention and assaying the GTPγS binding promoting activity on the membrane fraction containing the receptor of the present invention.

A specific example of the screening method is described below.

The membrane fraction containing the receptor of the present invention, which is prepared by a modification of publicly known methods, is diluted with a buffer for membrane dilution (50 mM Tris, 5 mM $MgCl_2$, 150 mM NaCl, 1 μM GDP, 0.1% BSA, pH 7.4). A degree of dilution varies depending upon the amount of a receptor expressed. The dilution is dispensed by 0.2 ml each in Falcon 2053, to which the ligand of the present invention or the ligand of the present invention and a test compound is/are added, and [$^{35}$S]GTPγS is further added to the mixture in a final concentration of 200 pM. After maintaining at 25° C. for an hour, 1.5 ml of ice-cooled wash buffer (50 mM Tris, 5 mM $MgCl_2$, 150 mM NaCl, 0.1% BSA, 0.05% CHAPS, pH 7.4) is added to the mixture followed by filtration through a glass fiber filter paper GF/F. After keeping at 65° C. for 30 minutes, the mixture is dried and the radioactivity of [$^{35}$S] GTPγS bound to the membrane fraction remained on the filter paper is measured with a liquid scintillation counter. When the radioactivity in the experimental zone added with the ligand of the present invention alone is defined as 100% and the radioactivity in the experimental zone not added with the ligand of the present invention is defined as 0%, an effect of the test compound on the GTPγS binding promoting activity by the ligand of the present invention is worked out. The test compound showing the GTPγS binding promoting activity of, for example, 50% or less can be selected as a candidate compound capable of antagonistic inhibition.

(2) In the cells where the receptor of the present invention is expressed, the intracellular cAMP production is suppressed by stimulation of the ligand of the present invention. Utilizing this reaction, the compound that alters the binding properties of the ligand of the present invention to the receptor of the present invention can be screened by assaying the stimulating activities of the ligand of the present invention on the cells where the receptor of the present invention is expressed.

Specifically, the compound that alters the binding properties of the ligand of the present invention to the receptor of the present invention can be screened by assaying intracellular cAMP production suppressing activities on the cells in the presence of a substance capable of increasing the intracellular cAMP level, when the ligand of the present invention is brought in contact with the cells where the receptor of the present invention is expressed and when the ligand of the present invention and a test compound are brought in contact with the cells where the receptor of the present invention is expressed; and comparing the activities.

As the substance capable of increasing the intracellular cAMP level, there are employed, e.g., forskolin, calcitonin, etc.

The level of cAMP produced in the cells where the receptor of the present invention is expressed can be assayed by the RIA system using an anti-cAMP antibody, whose antibody is obtained from immunized mouse, rat, rabbit, goat, bovine, etc., and [$^{125}$I]-labeled cAMP (both commercially available) or by the enzyme immunoassay (EIA) system using an anti-cAMP antibody and labeled cAMP in combination. It is also possible to quantify by the SPA (Scintillation Proximity Assay) method, using beads, which contain scintillants bearing anti-cAMP antibodies immobilized using protein A or antibodies to IgG, etc. of the animal used to produce the anti-cAMP antibodies, [$^{125}$I]-labeled cAMP (the kit manufactured by Amersham Pharmacia Biotech, Inc. is used) and the quantification by a competitive cAMP assay kit (Perkin Elmer) applying AlphaScreen (Perkin Elmer) or a chemical amplification type luminescence proximity homogeneous assay system.

According to this method, the test compound showing the activity of inhibiting the cAMP production suppressing activity by the ligand of the present invention against the cells where the receptor of the present invention is expressed can be selected as a candidate substance capable of antagonistic inhibition.

On the other hand, when a test compound alone is brought in contact with the cells where the receptor of the present invention is expressed, a compound showing an agonist activity can be screened by assaying the cAMP production suppressing activities.

A specific example of the screening method is described below.

The cells where the receptor of the present invention is expressed (e.g., animal cells such as CHO cells, etc.) are plated on a 24-well plate in $5 \times 10^4$ cells/well followed by cultivation for 48 hours. The cells are washed with Hanks' buffer (pH 7.4) supplemented with 0.2 mM 3-isobutyl-methylxanthine, 0.05% BSA and 20 mM HEPES (hereinafter simply referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 0.25 ml of a 2 µM forskolin-containing reaction buffer, in which 1 µM of the ligand of the present invention or 1 µM of the ligand of the present invention and a test compound is/are incorporated, is added to the cells, followed by reacting at 37° C. for 24 minutes. The reaction is terminated by adding 100 µl of 20% perchloric acid. The reaction mixture is then put on ice for an hour to extract intracellular cAMP. The amount of cAMP in the extract is measured using a cAMP EIA kit (Amersham Pharmacia Biotech). Taking the amount of cAMP produced by forskolin stimulation as 100% and the amount of cAMP inhibited by addition of 1 µM of the ligand of the present invention as 0%, an effect of the test compound on the cAMP production suppressing activity by the ligand of the present invention is calculated. The test compound that inhibits the activity of the ligand of the present invention to increase the cAMP producing activity, e.g., to 50% or more, can be selected as a candidate substance capable of antagonistic inhibition.

Further in the case of using the cells where the receptor of the present invention is expressed and which show the intracellular cAMP level increasing property through stimulation by the ligand of the present invention, the compound that alters the binding properties of the ligand of the present invention to the receptor of the present invention can be screened by assaying the intracellular cAMP production promoting activities on the cells, when the ligand of the present invention is brought in contact with the cells where the receptor of the present invention is expressed and when the ligand of the present invention and a test compound are brought in contact with the cells where the receptor of the present invention is expressed; and comparing the activities.

According to this method, the test compound showing the activity of inhibiting the cAMP production promoting activity by the ligand of the present invention against the cells where the receptor of the present invention is expressed can be selected as a candidate substance capable of antagonistic inhibition.

On the other hand, by monitoring the cAMP production promoting activity when a test compound alone is brought in contact with the cells where the receptor of the present invention is expressed, the compound showing the agonist activity can be screened.

To assay the cAMP production promoting activity, the level of cAMP produced by adding the ligand of the present invention or the ligand of the present invention and a test compound to the cells (e.g., animal cells such as CHO cells, etc.) in which the receptor of the present invention is expressed, without adding forskolin in the screening method described above, is quantified by the procedure described above.

(3) The compound that alters the binding properties of the ligand of the present invention to the receptor of the present invention can be screened by assaying the stimulating activities of the ligand of the present invention on the cell, in which the receptor of the present invention is expressed, using a CRE-reporter gene vector.

A DNA containing CRE (cAMP response element) is inserted into a vector upstream a reporter gene to acquire CRE-reporter gene vector. In the CRE-reporter gene vector-transfected cells, in which the receptor of the present invention is expressed, stimulation accompanied by increased cAMP induces expression of the reporter gene mediated by CRE and subsequent production of the gene product (protein) of the reporter gene. That is, changes in the amount of cAMP in the CRE-reporter gene vector-transfected cells can be detected by assaying the enzyme activity of the reporter gene protein.

Specifically, the compound that alters the binding properties of the ligand of the present invention to the receptor of the present invention can be screened by assaying the enzyme activities of the reporter gene protein on the cells in the presence of a substance capable of increasing the intracellular cAMP level, when the ligand of the present invention is brought in contact with the CRE-reporter gene vector-transfected cells where the receptor of the present invention is expressed and when the ligand of the present invention and a test compound are brought in contact with the CRE-reporter gene vector-transfected cells where the receptor of the present invention is expressed; and comparing the activities.

As the substance capable of increasing the intracellular cAMP level, there are employed, e.g., forskolin, calcitonin, etc.

As the vector, there may be employed, e.g., PicaGene Basic Vector, PicaGene Enhancer Vector (Toyo Ink Mfg. Co., Ltd.), and the like. A CRE-containing DNA is inserted into the vector described above at the multicloning site upstream the reporter gene, e.g., luciferase gene, which is made a CRE-reporter gene vector.

According to this method, a test compound which restores the enzyme activity suppression of the reporter gene protein by the ligand of the present invention can be selected as a candidate substance capable of antagonistic inhibition.

On the other hand, the agonist can be screened as well by contacting a test compound alone with the cell in which the receptor of the present invention is expressed and assaying the suppression of luminescence level increased by forskolin stimulation, as in the ligand of the present invention.

Taking as an example in which luciferase is used as a reporter gene, a specific example of this screening method is described below.

The CRE-reporter gene (luciferase)-transfected cells where the receptor of the present invention is expressed are plated on a 24-well plate in $5 \times 10^3$ cells/well followed by cultivation for 48 hours. The cells are washed with Hanks' buffer (pH 7.4) supplemented with 0.2 mM 3-isobutylmethylxanthine, 0.05% BSA and 20 mM HEPES (hereinafter merely referred to as a reaction buffer). Thereafter, 0.5 ml of the reaction buffer is added to the cells and the mixture is kept warm in the medium for 30 minutes. The reaction buffer is removed and 0.25 ml of a fresh reaction buffer is added to the cells. Then, 1 µM of the ligand of the present invention or 1 µM of the ligand of the present invention and a test compound is/are added to 0.25 ml of the reaction buffer containing 2 µM forskolin, which is added to the cells. The reaction is then carried out at 37° C. for 24 minutes. The cells are dissolved in a cell lysis agent for PicaGene (Toyo Ink Mfg. Co., Ltd.) and a luminescent substrate (Toyo Ink Mfg. Co., Ltd.) is added to the lysate. Luminescence by luciferase is measured with a luminometer, a liquid scintillation counter or a top counter. The levels of luminescence by luciferase are measured when only the ligand of the present invention is added and when 1 µM of the ligand of the present invention and a test compound are added, followed by comparing the levels of luminescence.

The ligand of the present invention suppresses the increase in luminescent level by luciferase, which increase is based on forskolin stimulation. The compound that restores the suppression can be selected as a candidate substance capable of antagonistic inhibition.

As the reporter gene, there may be employed genes, e.g., alkaline phosphatase, chloramphenicol acetyltransferase, β-galactosidase, etc. The enzyme activities of these reporter gene proteins are assayed in accordance with methods publicly know, or using commercially available assay kits. The alkaline phosphatase activity can be assayed by using, e.g., Lumi-Phos 530 manufactured by Wako Pure Chemical Industries, Ltd.; the chloramphenicol acetyltransferase activity by using, e.g., FAST CAT chloramphenicol Acetyltransferase Assay Kit manufactured by Wako Pure Chemical Industries, Ltd.; and the β-galactosidase activity by using, e.g., Aurora Gal-XE manufactured by Wako Pure Chemical Industries, Ltd.

(4) The cells where the receptor of the present invention is expressed extracellularly release arachidonic acid metabolites by stimulation of the ligand of the present invention. Utilizing this reaction, the stimulating activities of the ligand of the present invention on the cell in which the receptor of the present invention is expressed are assayed, whereby the compound that alters the binding properties of the ligand of the present invention to the receptor of the present invention can be screened.

Labeled arachidonic acid is previously taken up into the cell in which the receptor of the present invention is expressed. Thus, the arachidonic acid metabolite releasing activity can be assayed by measuring the labeled arachidonic acid metabolite released at the outside of the cell.

Specifically, the compound that alters the binding properties of the ligand of the present invention to the receptor of the present invention can be screened by assaying arachidonic acid metabolite-releasing activities, when the ligand of the present invention is brought in contact with the labeled arachidonic acid-containing cells where the receptor of the present invention is expressed and when the ligand of the present invention and a test compound are brought in contact with the labeled arachidonic acid-containing cells where the receptor of the present invention is expressed; and comparing the activities.

According to this method, the test compound that inhibits the arachidonic acid metabolite-releasing activity by the ligand of the present invention can be selected as a candidate substance capable of antagonistic inhibition.

Also, a test compound alone is brought into contact with the cell in which the receptor of the present invention is expressed and the arachidonic acid metabolite-releasing activity in the cell in which the receptor of the present invention is expressed is examined by publicly known methods. Thus, the compound showing the agonist activity can be screened as well.

A specific example of this screening method is described below.

The cells where the receptor of the present invention is expressed are plated on a 24-well plate in $5 \times 10^4$ cells/well. After cultivation for 24 hours, [$^3$H] arachidonic acid is added to the cells in 0.25 µCi/well. Sixteen hours later, the cells are washed with Hanks' buffer (pH 7.4) supplemented with 0.05% BSA and 20 mM HEPES (hereinafter simply referred to as a reaction buffer). To each well is added 500 µl of the reaction buffer containing the ligand of the present invention in the final concentration of 10 µM, or the ligand of the present invention in the final concentration of 10 µM and a test compound. After incubation at 37° C. for 60 minutes, 400 µl of the reaction solution is charged in a scintillator and the amount of [$^3$H] arachidonic acid metabolites released in the reaction solution is measured using a scintillation counter.

When the amount of released [$^3$H] arachidonic acid metabolites when 500 µl of the reaction buffer alone is added (neither the ligand of the present invention nor the test compound is added) is taken as 0% and the amount of released [$^3$H] arachidonic acid metabolites when the reaction buffer containing 10 µM of the ligand of the present invention is added (no test compound is added) is taken as 100%, the amount of released [$^3$H] arachidonic acid metabolites released where the test compound is added is calculated.

The compound showing the arachidonic acid metabolite-releasing activity of, e.g., 50% or less, can be selected as a candidate substance capable of antagonistic inhibition.

(5) In the cells where the receptor of the present invention is expressed, the intracellular Ca level increases by stimulation of the ligand of the present invention. Utilizing this reaction, the stimulating activities of the ligand of the present invention on the cells where the receptor of the present invention is expressed are assayed, whereby the compound that alters the binding properties of the ligand of the present invention to the receptor of the present invention can be screened.

Specifically, the compound that alters the binding properties of the ligand of the present invention to the receptor of the present invention is screened by assaying the intracellular calcium level increasing activities when the ligand of the present invention is brought in contact with the cells where the receptor of the present invention is expressed and when the ligand of the present invention and a test compound are brought in contact with the cells where the receptor of the present invention is expressed; and comparing the activities. The assay is carried out in accordance with methods publicly known.

According to this method, the test compound that suppresses the intracellular calcium level increasing activity by the ligand of the present invention can be selected as a candidate substance capable of antagonistic inhibition.

On the other hand, the agonist can be screened as well by assaying an increase of fluorescence intensity by the addition of a test compound alone.

A specific example of the screening method is described below.

The cells where the receptor of the present invention is expressed are plated on a sterilized cover glass for microscopy. Two days after, the culture medium is replaced by HBSS, in which 4 mM Fura-2 AM (Dojin Kagaku Kenkyusho) is suspended, and allowed to stand at room temperature for 2 hours and 30 minutes. After washing with HBSS, the cover glass is set on a cuvette, and an increased ratio of fluorescence intensity at 505 nm is measured with a fluorescence spectrophotometer at excited wavelengths of 340 nm and 380 nm, when the ligand of the present invention or the ligand of the present invention and a test compound is/are added, and comparison is made.

Also, FLIPR (manufactured by Molecular Device, Inc.) may be used. Fluo-3 AM (manufactured by Dojin Kagaku Kenkyusho) is added to a suspension of the cells where the receptor of the present invention is expressed, thereby to take Fluo-3 AM into the cells. After the supernatant is washed several times through centrifugation and the cells are plated on a 96-well plate. After setting in the FLIPR device, the ligand of the present invention or the ligand of the present invention and a test compound is/are added thereto. Using a fluorescence spectrophotometer, an increase in the ratio of fluorescence intensity is measured and comparison is made, as in the case using Fura-2.

Furthermore, the compound that alters the binding properties of the ligand of the present invention to the receptor of the present invention can also be screened by co-expressing a gene (e.g., aequorin, etc.) for the protein that emits light in response to increased Ca ions in the cells where the receptor of the present invention is expressed, and utilizing the luminescence emitted by conformational switch of the gene protein (e.g., aequorin, etc.) to the Ca-bound protein.

The cells where the receptor of the present invention and the gene for the protein capable of emitting light by increased intracellular Ca ions are co-expressed are plated on a 96-well plate. The ligand of the present invention or the ligand of the present invention and a test compound is/are added thereto, an increase in the ratio of fluorescence intensities is assayed using a fluorescence spectrophotometer, and comparison is made, as described above.

The test compound that suppresses the increase in fluorescence intensity by the ligand of the present invention can be selected as a candidate substance capable of antagonistic inhibition.

(6) When the receptor agonist is added to receptor-expressing cells, the level of intracellular inositol triphosphate increases. By utilizing the intracellular inositol triphosphate producing activity in the cells where the receptor of the present invention is expressed, the compound that alters the binding properties of the ligand of the present invention to the receptor of the present invention can be screened.

Specifically, the compound that alters the binding properties of the ligand of the present invention to the receptor of the present invention is screened by assaying the inositol triphosphate producing activities in the presence of labeled inositol, when the ligand of the present invention is brought in contact with the cells where the receptor of the present invention is expressed and when the ligand of the present invention and a test compound are brought in contact with the cells where the receptor of the present invention is expressed; and comparing the activities. The assay is carried out in accordance with methods publicly known.

According to this method, the test compound that suppresses the inositol triphosphate producing activities can be selected as a candidate substance capable of antagonistic inhibition.

On the other hand, an agonist can also be screened by contacting a test compound alone with the cells where the receptor of the present invention is expressed and assaying an increase in the inositol triphosphate production.

A specific example of the screening method is described below.

The cells wherein the receptor of the present invention is expressed are plated on a 24-well plate and cultured for a day. Then, the cells are cultured for a day in medium supplemented with myo-[2-$^3$H] inositol (2.5 μCi/well). The cells are thoroughly washed with radioactive inositol-free medium. After the ligand of the present invention or the ligand of the present invention and a test compound is/are added to the cells, 10% perchloric acid is added to terminate the reaction. The reaction mixture is neutralized with 1.5 M KOH and 60 mM HEPES solution and then passed through a column packed with 0.5 ml of AG1×8 resin (Bio-Rad). After washing with 5 mM sodium tetraborate ($Na_2B_4O_7$) and 60 mM ammonium formate, the radioactivity eluted with 1M ammonium formate and 0.1M formic acid is assayed with a liquid scintillation counter. When the radioactivity without adding the ligand of the present invention is made 0% and the radioactivity when the ligand of the present invention is added is made 100%, an effect of the test compound on the binding of the ligand of the present invention to the receptor of the present invention is calculated.

A test compound which reduces the inositol triphosphate production activity to, e.g., 50% or less, can be selected as a candidate substance capable of antagonistic inhibition.

(7) The compound that alters the binding properties of the ligand of the present invention to the receptor of the present invention can be screened by assaying the stimulating activities of the ligand of the present invention on the cells where the receptor of the present invention is expressed, using a TRE-reporter gene vector.

A DNA containing TRE (TPA response element) is inserted into a vector upstream the reporter gene to acquire a TRE-reporter gene vector. In the TRE-reporter gene vector-transfected cells where the receptor of the present invention is expressed, stimulation accompanied by an increase of the intracellular Ca levels induces expression of TRE-mediated reporter gene and production of the reporter gene product (protein) subsequent thereto. That is, changes in the calcium levels in the TRE-reporter gene vector-transfected cells can be detected by assaying the enzyme activity of the reporter gene protein.

Specifically, the compound that alters the binding properties of the ligand of the present invention to the receptor of the present invention is screened by assaying the enzyme activities of the reporter gene protein, when the ligand of the present invention is brought in contact with the TRE-reporter gene vector-transfected cells where the receptor of the present invention is expressed and when the ligand of the present invention and a test compound are brought in contact with the TRE-reporter gene vector-transfected cells where the receptor of the present invention is expressed; and comparing the activities.

As the vector, there may be employed, e.g., PicaGene Basic Vector, PicaGene Enhancer Vector (Toyo Ink Mfg. Co., Ltd.), and the like. A DNA containing TRE is inserted into the vector described above at the multicloning site upstream the reporter gene, e.g., luciferase gene, which is made a TRE-reporter gene vector.

According to this method, the test compound that suppresses the enzyme activity of the reporter gene protein by the ligand of the present invention can be selected as a candidate substance capable of antagonistic inhibition.

On the other hand, an agonist may also be screened by contacting a test compound alone with the TRE-reporter gene vector-transfected cells where the receptor of the present invention is expressed and measuring the increased level of luminescence, as in the ligand of the present invention.

Taking as an example the embodiment wherein luciferase is used as the reporter gene, a specific example of this screening method is described below.

The TRE-reporter gene (luciferase)-transfected cells where the receptor of the present invention is expressed are inoculated on a 24-well plate in $5 \times 10^3$ cells/well followed by incubation for 48 hours. After the cells are washed with Hanks' buffer (pH 7.4) supplemented with 0.05% BSA and 20 mM HEPES, 10 nM of the ligand of the present invention or 10 nM of the ligand of the present invention and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is assayed by a luminometer, a liquid scintillation counter or a top counter. The levels of luminescence by luciferase are measured when the ligand of the present invention is added and when 10 nM of the ligand of the present invention and a test compound are added, followed by comparison.

The level of luminescence by luciferase increases with elevation of intracellular calcium by the ligand of the present invention. The compound that suppresses the increase can be selected as a candidate substance capable of antagonistic inhibition.

As the reporter gene, there may be employed genes, e.g., alkaline phosphatase, chloramphenicol acetyltransferase, β-galactosidase, etc. The enzyme activities of these reporter gene proteins are assayed in accordance with methods publicly known, or by using assay kits commercially available. The alkaline phosphatase activity can be assayed by using, e.g., Lumi-Phos 530 manufactured by Wako Pure Chemical Industries, Ltd.; the chloramphenicol acetyltransferase activity using, e.g., FAST CAT chloramphenicol Acetyltransferase Assay Kit manufactured by Wako Pure Chemical Industries, Ltd.; and the β-galactosidase activity using, e.g., Aurora Gal-XE manufactured by Wako Pure Chemical Industries, Ltd.

(8) In the cell in which the receptor of the present invention is expressed, MAP kinase is activated by stimulation of the ligand of the present invention, and the cell grows. Utilizing the reaction, the compound that alters the binding properties of the ligand of the present invention to the receptor of the present invention can be screened by assaying the stimulation activities of the ligand of the present invention on the cell in which the receptor of the present invention is expressed.

Specifically, the compound that alters the binding properties of the ligand of the present invention to the receptor of the present invention is screened by assaying the cell growth, when the ligand of the present invention is brought in contact with the cells where the receptor of the present invention is expressed and when the ligand of the present invention and a test compound are brought in contact with the cells where the receptor of the present invention is expressed; and comparing the cell growth.

The growth of the cells where the receptor of the present invention is expressed may be determined by assaying, e.g., the MAP kinase activity, the thymidine uptake activity, the ATP level, the cell count, etc.

In a specific example, the MAP kinase activity is assayed as follows. The ligand of the present invention or the ligand of the present invention and a test compound is/are added to the cell in which the receptor of the present invention is expressed; immunoprecipitation is carried out using an anti-MAP kinase antibody to obtain a MAP kinase fraction from a cell lysate; then using, e.g., MAP Kinase Assay Kit manufactured by Wako Pure Chemical Industries, Ltd. and γ-[$^{32}$P]-ATP, the MAP kinase activity is assayed, and comparison is made.

In assaying the thymidine uptake activities, cells where the receptor of the present invention is expressed are plated on a 24-well plate and incubated. After the ligand of the present invention or the ligand of the present invention and a test compound is/are added to the cells, radioactively labeled thymidine (e.g., [methyl-$^3$H]-thymidine, etc.) is added thereto. Subsequently, the cells are lysed and by counting the radioactivity of the labeled thymidine taken up into the cells with a liquid scintillation counter, the thymidine uptake activities are assayed and compared.

In assaying the ATP levels, cells wherein the receptor of the present invention is expressed are plated on a 96-well plate and incubated. The ligand of the present invention or the ligand of the present invention and a test compound is/are added thereto, and intracellular ATP levels are assayed using, e.g., CellTiter-Glo (Promega) and compared.

In assaying cell counts, the cells where the receptor of the present invention is expressed are plated on a 24-well plate, followed by incubation. The ligand of the present invention or the ligand of the present invention and a test compound is/are added to the cells, and MTT (3-(4,5-dimethyl-2-thiazolyl)-2,5-diphenyl-2H-tetrazolium bromide) is further added thereto. MTT taken up into the cells changes to MTT formazan, which absorption is measured at 570 nm after the cells are lysed with isopropanol rendered acidic with hydrochloric acid. Then, comparison is made.

According to this method, the test compound that suppresses the growth of cells where the receptor of the present invention is expressed can be selected as a candidate substance capable of antagonistic inhibition.

On the other hand, the agonist may also be screened by contacting a test compound alone with the cells where the receptor of the present invention is expressed and assaying the cell growth activities as in the ligand of the present invention.

A specific example of the screening method utilizing the thymidine uptake activity is described below.

The cells where the receptor of the present invention is expressed are plated on a 24-well plate in 5000 cells/well followed by incubation for one day. Next, the cells are incubated in a serum-free medium for 2 days to bring the cells under starvation. The ligand of the present invention or the ligand of the present invention and a test compound is/are added to the cells. After incubation for 24 hours, [methyl-$^3$H] thymidine is added in 0.015 MBq/well, followed by incubation for 6 hours. After the cells are washed with PBS, methanol is added to the cells. The mixture is allowed to stand for 10 minutes. Next, 5% trichloroacetic acid is added and the mixture is allowed to stand for 15 minutes. The fixed cells are washed 4 times with distilled water. After the cells are lysed with 0.3 N sodium hydroxide solution, the radioactivities in the lysate are assayed with a liquid scintillation counter.

The compound that suppresses the increased radioactivity by addition of the ligand of the present invention can be selected as a candidate substance capable of antagonistic inhibition.

(9) In the cells in which the receptor of the present invention is expressed, the potassium channel is activated by stimulation of the ligand of the present invention so that K ions present within the cells are effluxed outside the cells. Utilizing this reaction, the compound that alters the binding properties of the ligand of the present invention to the receptor of the present invention can be screened by assaying the stimulating activities of the ligand of the present invention on the cells where the receptor of the present invention is expressed.

Rb ions (rubidium ions) in the related elements to K ions flow out of the cells through the potassium channel without being distinguished from K ions. Thus, radioactive isotope Rb ([$^{86}$Rb]) is previously incorporated in the cells where the receptor of the present invention is expressed, and the efflux of $^{86}$Rb that flows out in response to stimulation by the ligand of the present invention (efflux activity) is determined thereby to assay the stimulating activity of the ligand of the present invention on the cells where the receptor of the present invention is expressed.

Specifically, the compound that alters the binding properties of the ligand of the present invention to the receptor of the present invention is screened by assaying $^{86}$Rb efflux activities in the presence of $^{86}$Rb, when the ligand of the present invention is brought in contact with the cells where the receptor of the present invention is expressed and when the ligand of the present invention and a test compound are brought in contact with the cells where the receptor of the present invention is expressed; and comparing the activities.

According to this method, the test compound that suppresses the increase of the $^{86}$Rb efflux activities associated with stimulation by the ligand of the present invention can be selected as a candidate substance capable of antagonistic inhibition.

On the other hand, the agonist can be screened as well by contacting a test compound alone with the cell in which the receptor of the present invention is expressed and assaying the increased efflux activity of $^{86}$Rb, as in the ligand of the present invention.

A specific example of the screening method is described below.

The cells where the receptor of the present invention is expressed are plated on a 24-well plate and cultured for 2 days. Thereafter, the cells are kept warm for 2 hours in a medium containing 1 mCi/ml of $^{86}$RbCl. The medium is thoroughly washed to completely remove $^{86}$RbCl in the outer liquid. The ligand of the present invention or the ligand of the present invention and a test compound is/are added to the cells. After the outer liquid is recovered 30 minutes later, the radioactivities are assayed with a γ counter, and comparison is made.

The test compound which suppresses the increase in the efflux activity of $^{86}$Rb by stimulation of the ligand of the present invention can be selected as a candidate substance capable of antagonistic inhibition.

(10) In the cells where the receptor of the present invention is expressed, the extracellular pH changes in response to the ligand of the present invention. Utilizing this reaction, the compound that alters the binding properties of the ligand of the present invention to the receptor of the present invention can be screened by assaying the stimulating activity of the ligand of the present invention on the cells where the receptor of the present invention is expressed.

Specifically, the compound that alters the binding properties of the ligand of the present invention to the receptor of the present invention is screened by assaying changes in extracellular pH, when the ligand of the present invention is brought in contact with the cells where the receptor of the present invention is expressed and when the ligand of the present invention and a test compound are brought in contact with the cells where the receptor of the present invention is expressed; and comparing the changes.

The extracellular pH changes are assayed by using, e.g., Cytosensor Device (Molecular Device, Inc.).

According to this method, the test compound that suppresses the extracellular pH changes by the ligand of the present invention can be selected as a candidate substance capable of antagonistic inhibition.

On the other hand, the agonist can also be screened by contacting a test compound alone with the cells where the receptor of the present invention is expressed and assaying the extracellular pH changes, as in the ligand of the present invention.

A specific example of the screening method is described below.

The cells where the receptor of the present invention is expressed are cultured overnight in a capsule for Cytosensor Device, which is set in a chamber of the device to reflux 0.1% BSA-containing RPMI 1640 medium (manufactured by Molecular Device, Inc.) for about 2 hours until the extracellular pH becomes stable. After the pH becomes stable, the medium containing the ligand of the present invention or the ligand of the present invention and a test compound is refluxed onto the cells. The pH changes in the medium caused by reflux are assayed and compared.

The compound that suppresses the extracellular pH changes by the ligand of the present invention can be selected as a candidate substance capable of antagonistic inhibition.

(11) In *Saccharomyces Cerevisiae*, sex pheromone receptor STe2 of haploid α-mating type (MATα) is coupled to G protein Gpa1 to activate MAP kinase in response to sex pheromone α-mating factor, whereby Far1 (cell-cycle arrest) and transcription activator Ste12 are activated. Ste12 induces expression of a wide variety of protein (e.g., FUS1 which participates in conjugation). On the other hand, regulator Sst2 functions to inhibit the foregoing process. In this system, an attempt has been made to construct the assay system for the reaction of a receptor agonist with a receptor, which involves preparing a receptor gene-transfected yeast, activating the intracellular signal transduction system in yeast by stimulation with the receptor agonist and using the resulting growth, etc. as an indicator (Trends in Biotechnology, 15, 487-494, 1997). Utilizing this receptor gene-transfected yeast system, the compound that alters the binding properties of the ligand of the present invention to the receptor of the present invention can be screened.

A specific example is described below.

The Ste2 and Gpa1-coding genes in MATα yeast are removed and instead, the gene for the receptor of the present invention and the Gpa1-Gai2 fused protein-coding gene are introduced. The Far1-coding gene is previously removed to cause no cell-cycle arrest and the Sst2-coding gene is removed to increase the sensitivity in response to the ligand of the present invention. Furthermore, FUS1-HIS3 gene, which is FUS1 ligated with histidine biosynthesis gene HIS3, is introduced. This genetic recombinant engineering can be carried out, e.g., by replacing the receptor of the present invention for somatostatin receptor type 2 (SSTR2) gene, in the method described in Molecular and Cellular Biology, 15, 6188-6195, 1995.

The thus constructed transformant yeast is responsive to the ligand of the present invention with a high sensitivity so that MAP kinase is activated to cause synthesis of histidine biosynthesis enzyme. Thus, the transformant becomes capable of growing in a histidine-deficient medium.

Accordingly, the compound that alters the binding properties of the ligand of the present invention to the receptor of the present invention can be screened by incubating the yeast described above in which the receptor of the present invention is expressed (MATα yeast wherein the Ste2 gene and the Gpa1 gene are removed, the gene for the receptor of the present invention and the Gpa1-Gai2 fused protein-encoding gene are introduced, the Far gene and the Sst2 gene are removed, and the FUS1-HIS3 gene is introduced) in a histidine-deficient medium, contacting the ligand of the present invention or the ligand of the present invention and a test compound with the yeast, assaying growth of the yeast, and comparing the growth.

According to this method, the test compound that suppresses growth of the yeast can be selected as a candidate substance capable of antagonistic inhibition.

On the other hand, the agonist can be screened as well by contacting a test compound alone with the yeast in which the receptor of the present invention is expressed and assaying growth of the yeast, as in the ligand of the present invention.

A specific example of the screening method is described below.

The yeast described above in which the receptor of the present invention is expressed thus produced is incubated overnight in a complete synthesis liquid medium and then added to a histidine-free, dissolved agar medium in a concentration of $2 \times 10^4$ cells/ml. Then, the yeast is plated on a square Petri dish of 9×9 cm. After the agar is solidified, a sterilized filter paper impregnated with the ligand of the present invention or the ligand of the present invention and a test compound is put on the agar surface, which is incubated at 30° C. for 3 days. To determine the effect of the test compound, growth of yeast around the filter paper is compared to the case wherein the sterilized filter paper impregnated only with the ligand of the present invention. Alternatively, the assay can be made by previously adding the ligand of the present invention to a histidine-free agar medium, impregnating the sterilized, filter paper with a test compound alone to incubate the yeast and monitoring that growth of the yeast over the entire surface of the Petri dish is affected at the periphery of the filter paper.

The compound that suppresses growth of the yeast can be selected as a candidate substance capable of antagonistic inhibition.

(12) When gene RNA of the receptor of the present invention is injected into *Xenopus laevis* oocytes and stimulated by the ligand of the present invention, the intracellular Ca ion level increases to cause a calcium-activated chloride current, which can be taken as fluctuation in membrane potential (the same applies also to the case where fluctuation occurs in K ion level gradient). Making use of the above reaction caused by the ligand of the present invention in *Xenopus laevis* oocytes where the receptor of the present invention is transfected, the compound that alters the binding properties of the ligand of the present invention to the receptor of the present invention can be screened by assaying the stimulating activities of the ligand of the present invention on the cells where the receptor of the present invention is expressed.

Specifically, the compound that alters the binding properties of the ligand of the present invention to the receptor of the present invention can be screened by assaying changes in cell membrane potential, when the ligand of the present invention is brought in contact with *Xenopus laevis* oocytes where RNA gene for the receptor of the present invention is introduced and when the ligand of the present invention and a test compound are brought in contact with *Xenopus laevis* oocytes where RNA gene for the receptor of the present invention is introduced; and comparing the changes.

According to this method, the test compound that suppresses the changes in cell membrane potential can be selected as a candidate substance capable of antagonistic inhibition.

On the other hand, the agonist can be screened as well by contacting a test compound alone with *Xenopus laevis* oocytes where RNA gene for the receptor of the present invention is introduced and assaying the changes in cell membrane potential, as in the ligand of the present invention.

A specific example of the screening method is described below.

A female *Xenopus laevis* anesthetized by immersing in ice water is anatomized to withdraw oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES; pH 7.4) at 19° C. for 1 to 6 hours at 150 rpm, until the oocytes are loosen. Washing is performed 3 times by replacing the outer liquid with the MBS solution followed by microinjection of the gene for the receptor of the present invention or poly A-added cRNA (50 ng/50 nl) with a micromanipulator.

The mRNA gene for the receptor of the present invention may be prepared from tissues or cells, or may be transcribed from plasmids in vitro. The mRNA gene for the receptor of the present invention is incubated in the MBS solution at 20° C. for 3 days. The oocytes are placed in a hole of a voltage clamp device, which is continuously perfused with Ringer's solution, and impaled into the cells with glass microelectrodes for voltage clamp and glass microelectrodes for potential recording, in which (−) electrode is placed outside the oocytes. When the holding potential stabilizes, Ringer's solution containing the ligand of the present invention or the ligand of the present invention and a test compound is perfused to record a change in potential. An effect of the compound can be determined by comparing a change in cell membrane potential of the *Xenopus laevis* oocytes wherein RNA gene for the receptor of the present invention is transfected, with the case wherein Ringer's solution containing the ligand of the present invention alone is perfused.

The compound that suppresses the changes in cell membrane potential can be selected as a candidate substance capable of antagonistic inhibition.

In the system described above, the changes in potential can be monitored more easily when the variations in potential increase. Therefore, polyA-added RNA of various G protein genes may be introduced. Also, the level of luminescence, not the changes in membrane potential, can be measured by co-injecting polyA-added RNA of a gene for the protein (e.g., aequorin, etc.) that emits light in the presence of calcium.

The kit for screening the compound or its salt that alters the binding properties of the ligand of the present invention to the receptor of the present invention comprises the receptor of the present invention or the cell or cell membrane fraction containing the receptor of the present invention, and the ligand of the present invention.

Examples of the screening kits of the present invention are as follow.

1. Reagents for Screening (i) Assay Buffer and Wash Buffer

Hanks' Balanced Salt Solution (manufactured by Invitrogen, Inc.) supplemented with 0.05% bovine serum albumin (manufactured by Sigma, Inc.).

The solution is sterilized by filtration through a 0.45 μm filter, and stored at 4° C. or may be prepared at use.

(ii) Receptor Preparation of the Present Invention

CHO cells where the receptor of the present invention is expressed are subcultured on a 12-well plate at a density of $5×10^5$ cells/well and cultured at 37° C. under 5% $CO_2$ and 95% air for 2 days.

(iii) Labeled Ligand

An aqueous solution of the ligand of the present invention labeled with commercially available [$^3$H], [$^{125}$I], [$^{14}$C], [$^{32}$P], [$^{33}$P], [$^{35}$S], etc. is stored at 4° C. or −20° C., and diluted to 1 μM with the assay buffer upon use.

(iv) Standard Ligand Solution

The ligand of the present invention is dissolved in PBS supplemented with 0.1% bovine serum albumin (manufactured by Sigma, Inc.) in a volume of 1 mM, and the solution is stored at −20° C.

2. Assay Method (i) The cells where the receptor of the present invention is expressed are cultured on a 12-well culture plate. After washing twice with 1 ml of the assay buffer, 490 μl of the assay buffer is added to each well.

(ii) After 5 μl of a solution of test compound in $10^{-3}$ to $10^{-10}$ M is added, 5 μl of a labeled form of the ligand of the present invention is added thereto. The reaction is carried out at room temperature for an hour. To examine the non-specific binding, 5 μl of the ligand of the present invention of $10^{-3}$ M is previously added in place of the test compound.

(iii) The reaction solution is removed and the wells are washed 3 times with 1 ml of the wash buffer. A labeled form of the ligand of the present invention bound to the cells is dissolved in 0.2N NaOH-1% SDS, and mixed with 4 ml of liquid scintillator A (manufactured by Wako Pure Chemical Industries, Ltd.).

(iv) Radioactivities are assayed using a liquid scintillation counter (manufactured by Beckman, Inc.), and the percent maximum binding (PMB) is calculated in accordance with the following equation.

$$PMB=[(B-NSB)/(B_0-NSB)]\times 100$$

PMB: Percent maximum binding
B: Value obtained in the presence of a test compound
NSB: Non-specific binding
$B_0$: Maximum binding The compound or its salt, which is obtained using the screening methods or the screening kits of the present invention, is the compound that alters the binding of the ligand of the present invention to the receptor of the present invention, or the compound that promotes or inhibits the activity of the receptor of the present invention and specifically, is (i) the compound or its salt that has the cell stimulating activities mediated by the receptor of the present invention (an agonist to the receptor of the present invention); (ii) the compound that does not have the stimulating activities (an antagonist to the receptor of the present invention); (iii) the compound that promotes the binding affinity of the receptor of the present invention and the ligand of the present invention; (iv) the compound that inhibits the binding affinity of the receptor of the present invention and the ligand of the present invention; or the like. Examples of these compounds include those selected from peptides, proteins, antibodies, non-peptide compounds, synthetic compounds, fermentation products, cell extracts, plant extracts, animal tissue extracts, blood plasma, etc. These compounds may be novel or publicly known compounds.

The compound may form salts, and the salts of these compounds used are the same as those given for the test compound described above.

To determine if the compounds are agonists or antagonists to the receptor of the present invention described above, the following (i) or (ii) is available.

(i) The binding assay described in the screening methods (a)-(c) above is performed to obtain the compound that alters the binding properties of the ligand of the present invention to the receptor of the present invention (especially inhibits the binding) followed by assay for the compound to determine if the compound has the cell stimulating activities mediated by the receptor of the present invention described above. The compound or its salts having the cell stimulating activities are agonists to the receptor of the present invention (agonists), whereas the compound or its salts having no such activity are antagonists to the receptor of the present invention (antagonists).

(ii) (a) A test compound is brought in contact with cells containing the receptor of the present invention to assay the cell stimulating activities mediated by the receptor of the present invention. The compound or its salts having the cell stimulating activities are agonists to the receptor of the present invention.

(b) The cell stimulating activities mediated by the receptor of the present invention are assayed in the case that the ligand of the present invention is brought in contact with the cells containing the receptor of the present invention and in the case that the ligand of the present invention and a test compound are brought in contact with the cells containing the receptor of the present invention, and comparison is made on the cell stimulating activities. The compound or its salts capable of reducing the cell stimulating activities by the compound that activates the receptor of the present invention are antagonists to the receptor of the present invention.

As described above, the ligand of the present invention has the digestive tract (gastrointestinal) function modulating activity, the intestinal cell proliferation modulating activity, etc. Thus, the agonist to the receptor of the present invention exhibits activities similar to the physiological activities (e.g., the digestive tract (gastrointestinal) function modulating activity, the intestinal cell proliferation modulating activity, etc.) possessed by the ligand of the present invention, and is useful as a safe and low toxic medicament, for example, as an agent for the prevention/treatment of, e.g., digestive tract (gastrointestinal) disorders, cancer, immune disorders, diabetes mellitus, etc., preferably as an agent for the prevention/treatment of digestive tract disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus, and the like.

The antagonist to the receptor of the present invention can suppress the physiological activities (e.g., the digestive tract (gastrointestinal) function modulating activity, the intestinal cell proliferation modulating activity, etc.) possessed by the ligand of the present invention and is useful as a safe and low toxic medicament, for example, as an agent for the treatment/prevention of, for example, digestive tract (gastrointestinal) disorders, cancer, immune disorders, diabetes mellitus, etc., preferably as an agent for the prevention/treatment of digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, and so on.

The compound that promotes the binding affinity of the receptor of the present invention to the ligand of the present invention is useful as a safe and low toxic medicament, e.g., as an agent for the prevention/treatment of, for example, digestive tract (gastrointestinal) disorders, cancer, immune disorders, diabetes mellitus, etc., preferably as an agent for the prevention/treatment of digestive tract disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus, and the like.

The compound that inhibits the binding affinity of the receptor of the present invention to the ligand of the present invention is useful as a safe and low toxic medicament, for instance, as an agent for the prevention/treatment of, e.g., digestive tract (gastrointestinal) disorders, cancer, immune disorders, diabetes mellitus, etc., preferably as an agent for the prevention/treatment of digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, and so on.

Moreover, the present invention also provides the method of screening the compound or its salt that promotes or inhibits expression of the gene for the receptor of the present invention, which comprises using the polynucleotide of the present invention encoding the receptor of the present invention, and so on.

Specifically, the compound or its salts that promote or inhibit expression of the gene for the receptor of the present invention is screened by comparing the case (i) where a cell capable of producing the receptor of the present invention is cultured, and the case (ii) where a mixture of the cell capable of producing the receptor of the present invention and a test compound is cultured.

In the screening method described above, the gene expression level of the receptor of the present invention (specifically, the level of the receptor of the present invention or the level of mRNA encoding the receptor of the present invention, etc.) is assayed in the cases (i) and (ii), and comparison is made.

Examples of the test compound include peptides, proteins, antibodies, non-peptide compounds, synthetic compounds, fermentation products, cell extracts, plant extracts, animal tissue extracts, blood plasma, etc. These compounds may be novel or known compounds.

The test compound may form salts and as salts of the test compounds, there are employed the same salts of the test compounds as used for the screening method in the cell stimulation assay system, etc.

To perform the screening method described above, the cells capable of producing the polypeptide of the present invention or the receptor of the present invention are suspended in a buffer suitable for the screening to prepare the suspension. Any buffer can be used so long as it does not interfere the activities of the receptor of the present invention, including a phosphate buffer or a borate buffer, having pH of about 4 to about 10 (preferably pH of about 6 to about 8), etc.

As the cells capable of producing the receptor of the present invention, there are used, for example, a host (transformant) transformed with a vector containing the DNA encoding the receptor of the present invention. Preferably, animal cells such as CHO cells, etc. are used as the host. For the screening, the transformant, in which the receptor of the present invention has been secreted extracellularly by culturing through the procedures described above, is preferably employed.

The protein level in the receptor of the present invention can be determined by publicly known methods, e.g., by assaying the above-described polypeptide or receptor present in the cell extract, etc., using the antibody of the present invention, in accordance with methods like western blot analysis, ELISA, etc., or modifications thereof.

The gene expression level of the receptor of the present invention can be determined by publicly known methods, e.g., in accordance with methods including northern blotting, reverse transcription-polymerase chain reaction (RT-PCR), real time PCR monitoring system (manufactured by ABI Inc., TaqMan polymerase chain reaction), etc., or modifications thereof.

For example, when a test compound promotes expression of the gene for the receptor of the present invention in the case (ii) described above by at least about 20%, preferably at least 30% and more preferably at least about 50%, as compared to the case (i) above, the test compound can be selected as the compound or its salt that promotes expression of the gene for the receptor of the present invention.

For example, when a test compound inhibits expression of the gene for the receptor of the present invention in the case (ii) described above by at least about 20%, preferably at least 30% and more preferably at least about 50%, as compared to the case (i) above, the test compound can be selected to be the compound or its salt that inhibits expression of the gene for the receptor of the present invention.

The compound or its salt that promotes expression (increases the expression level) of the gene for the receptor of the present invention is used as a medicament, for instance, as an agent for the prevention/treatment of, e.g., digestive tract (gastrointestinal) disorders, cancer, immune disorders, diabetes mellitus, etc., preferably as an agent for the prevention/treatment of digestive tract disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus, and the like, as in the ligand of the present invention.

The compound or its salt that inhibits expression of the gene for the receptor of the present invention can suppress the physiological activities of the ligand of the present invention for the receptor of the present invention and is thus useful as an agent for the prevention/treatment of, for example, digestive tract (gastrointestinal) disorders, cancer, immune disorders, diabetes mellitus, etc., preferably as an agent for the prevention/treatment of digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, and so on.

The compound or its salt, which is obtained using the screening methods or screening kits of the present invention, is the compound selected from, for example, peptides, proteins, antibodies, non-peptide compounds, synthetic compounds, fermentation products, cell extracts, plant extracts, animal tissue extracts, blood plasma, etc. The compound that alters the binding properties of the receptor of the present invention to the ligand of the present invention, the compound that promotes or inhibits the activities or functions of the receptor of the present invention, the compound that promotes or inhibits the expression (increases or decreases the expression level) of the gene for the receptor of the present invention, etc.

The salts of these compounds used are the same given as the salts of the test compound described above.

When the compound or its salt, which is obtained by the screening methods or kits of the present invention, is used as the aforesaid medicament (the agent for the prevention/treatment, etc.), such can be carried out in a conventional manner.

The compound or its salt can be administered orally, for example, in the form of tablets which may be sugar coated, if necessary, capsules, elixirs, microcapsules etc., or parenterally in the form of injections such as sterile solutions or suspensions in water or in pharmaceutically acceptable solutions other than water. For example, the compound or its salt can be mixed with carriers, flavoring agents, excipients, vehicles, preservatives, stabilizers, binders, etc. in a unit dosage form generally accepted. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, a flavoring agent such as peppermint, akamono oil and cherry, etc. When the unit dosage is in the form of a capsule, liquid carriers such as oils and fats may further be used together with the additives described above. A sterile composition for injection may be formulated in a conventional manner used to make pharmaceutical preparations, e.g., by dissolving or suspending the active ingredients in a vehicle such as water for injection with a naturally occurring vegetable oil such as sesame oil and coconut oil, etc. to prepare the pharmaceutical preparations.

Examples of an aqueous medium for injection include physiological saline and an isotonic solution containing glucose and other auxiliary agents (e.g., D-sorbitol, D-mannitol, sodium chloride, etc.), or the like and may be used in combination with an appropriate dissolution aid such as an alcohol (e.g., ethanol, etc.), a polyalcohol (e.g., propylene glycol and polyethylene glycol, etc.), a nonionic surfactant (e.g., polysorbate 80™, HCO-50, etc.), or the like. Examples of the oily medium include sesame oil, soybean oil, etc., which may also be used in combination with a dissolution aid such as benzyl benzoate, benzyl alcohol, etc. The compound or its salt may further be formulated together with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

Since the pharmaceutical preparation thus obtained is safe and low toxic, it can be administered to human or other warm-blooded mammal (e.g., mouse, rat, rabbit, sheep, swine, bovine, horse, fowl, cat, dog, monkey, chimpanzee, etc.).

The dose of the agonist to the receptor of the present invention varies depending on subject to be administered, target disease, conditions, route for administration, etc.; in oral administration of the agonist to the treatment of, e.g., type II diabetes mellitus, the compound is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the agonist varies depending on subject to be administered, target disease, conditions, route for administration, etc. When the agonist is administered in the form of an injectable preparation for the treatment of, e.g., type II diabetes mellitus, it is advantageous to intravenously administer the compound to an adult (as 60 kg body weight) at a daily dose of about 0.01 to about 30 mg, preferably about 0.1 to about 20 mg, and more preferably about 0.1 to about 10 mg. For other animal species, the corresponding dose as converted per 60 kg body weight can be administered.

On the other hand, the dose of the antagonist to the receptor of the present invention varies depending on subject to be administered, target disease, conditions, route for administration, etc.; in oral administration of the antagonist to the treatment of, e.g., colon cancer, the compound is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the antagonist varies depending on subject to be administered, target disease, conditions, route for administration, etc. When the antagonist is administered in the form of an injectable preparation for the treatment of, e.g., colon cancer, it is advantageous to intravenously administer the compound to an adult (as 60 kg body weight) at a daily dose of about 0.01 to about 30 mg, preferably about 0.1 to about 20 mg, and more preferably about 0.1 to about 10 mg. For other animal species, the corresponding dose as converted per 60 kg body weight can be administered.

Furthermore, the dose of the compound or its salt that promotes or inhibits the binding affinity of the receptor of the present invention to the ligand of the present invention varies depending on subject to be administered, target disease, conditions, route for administration, etc.; in oral administration of the compound for the treatment of, e.g., colon cancer, the compound is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the compound varies depending on subject to be administered, target disease, conditions, route for administration, etc. but when the compound is administered in the form of an injectable preparation for the treatment of, e.g., colon cancer, it is advantageous to intravenously administer the compound to an adult (as 60 kg body weight) at a daily dose of about 0.01 to about 30 mg, preferably about 0.1 to about 20 mg, and more preferably about 0.1 to about 10 mg. For other animal species, the corresponding dose as converted per 60 kg body weight can be administered.

[2] Agent for Prevention/Treatment of Various Diseases Associated with Receptor of the Present Invention.

The receptor of the present invention has the binding activities to the ligand of the present invention, which possesses the activities described above. Accordingly, where the receptor of the present invention or the polynucleotide (e.g., DNA) of the present invention involves abnormalities or deficiencies, it is highly likely for one to suffer from, for example, digestive tract (gastrointestinal) disorders, cancer, immune disorders, diabetes mellitus, etc., preferably digestive tract disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus, and the like. Thus, the receptor of the present invention or the polynucleotide (e.g., DNA) of the present invention can be used as a low toxic and safe medicament including as an agent for the prevention/treatment of, for example, digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus, and the like.

When a patient has a reduced level of, or deficient of the receptor of the present invention or the polynucleotide of the present invention in a patient's body, the receptor of the present invention can provide its role sufficiently or properly for the patient, (i) by administering the polynucleotide of the present invention to the patient to express the receptor of the present invention in the body, (ii) by inserting the polynucleotide of the present invention into a cell to express the receptor of the present invention and then transplanting the cell to the patient, or (iii) by administering the receptor of the present invention to the patient, etc.

When the polynucleotide of the present invention is used as the agent for the prevention/treatment described above, the polynucleotide may be administered alone to human or other warm-blooded animal; or the polynucleotide is inserted into an appropriate vector such as retrovirus vector, adenovirus vector, adenovirus-associated virus vector, etc. and then administered to human or other warm-blooded animal in a conventional manner. The polynucleotide of the present invention may also be administered in its intact form; or the polynucleotide may be prepared into a pharmaceutical composition together with physiologically acceptable carriers such as adjuvants, etc. to assist its uptake and the pharmaceutical preparation may be administered by gene gun or through a catheter such as a catheter with a hydrogel.

When the receptor of the present invention is used as the agent for the prevention/treatment described above, it is advantageous to use the receptor in a purity of at least 90%, preferably at least 95%, more preferably at least 98% and most preferably at least 99%.

The receptor of the present invention can be used orally, for example, in the form of tablets which, if necessary, may be sugar coated, capsules, elixirs, microcapsules etc., or parenterally in the form of injectable preparations such as a sterile solution or a suspension, etc. in water or in other pharmaceutically acceptable liquid. These preparations can be manufactured, for example, by mixing the receptor of the present invention with a physiologically acceptable known carrier, a flavoring agent, an excipient, a vehicle, an antiseptic agent, a stabilizer, a binder, etc. in a unit dosage form required in a generally accepted fashion that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol, etc.), a polyalcohol (e.g., propylene glycol, polyethylene glycol, etc.), a nonionic surfactant (e.g., polysorbate 80™, HCO-50, etc.), or the like. Examples of the oily medium include sesame oil, soybean oil, etc., which may also be used in combination with a dissolution aid such as benzyl benzoate, benzyl alcohol, etc. The oily medium may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus prepared liquid for injection is normally filled in an appropriate ampoule.

The vector in which the polynucleotide (e.g., DNA) of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded mammal (e.g., rat, mouse, guinea pig, rabbit, fowl, sheep, swine, bovine, horse, cat, dog, monkey, etc.).

The dose of the receptor of the present invention varies depending on subject to be administered, target disease, conditions, route for administration, etc.; in oral administration of the receptor for the treatment of, e.g., type II diabetes mellitus, the receptor is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the receptor varies depending on subject to be administered, target disease, conditions, route for administration, etc. but when the receptor is administered in the form of an injectable preparation for the treatment of, e.g., type II diabetes mellitus, it is advantageous to intravenously administer the receptor to an adult (as 60 kg body weight) normally at a daily dose of about 0.01 to about 30 mg, preferably about 0.1 to about 20 mg, and more preferably about 0.1 to about 10 mg. For other animal species, the corresponding dose as converted per 60 kg body weight can be administered.

[3] Quantification of Receptor of the Present Invention

The antibody of the present invention is capable of specifically recognizing the receptor of the present invention. Therefore, the antibody can be used to quantify the receptor of the present invention in a test fluid, especially for quantification by the sandwich immunoassay, etc.

That is, the present invention provides, for example, the following methods of quantification:

(i) a method of quantifying the receptor of the present invention in a test fluid, which comprises competitively reacting the antibody of the present invention with the test fluid and a labeled form of the receptor of the present invention, and measuring the ratio of the labeled receptor of the present invention bound to the antibody; and, (ii) a method of quantifying the receptor of the present invention in a test fluid, which comprises reacting the test fluid with the antibody of the present invention immobilized on a carrier and a labeled form of another antibody of the present invention simultaneously or sequentially, and assaying the activity of the label on the immobilized carrier.

In the quantification method (ii) described above, it is preferred that one antibody recognizes the N-terminal domain of the receptor of the present invention, and another antibody reacts with the C-terminal domain of the receptor of the present invention.

Using a monoclonal antibody to the receptor of the present invention, the receptor of the present invention can be assayed and the detection by tissue staining. etc. is also available. For these purposes, the antibody molecule itself may be used, or $F(ab')_2$, Fab' or Fab fractions of the antibody molecule may be used as well.

The method of quantifying the receptor of the present invention using the antibody of the present invention is not particularly limited, and any method may be used, so long as the amount of antibody, antigen, or antibody-antigen complex in response to the amount of antigen (e.g., the polypeptide level) in a test fluid can be detected by chemical or physical means and can be calculated from a standard curve prepared from standard solutions containing known amounts of the antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same are radioisotopes, enzymes, fluorescent substances, luminescent substances, etc. Examples of the radioisotopes employed are $[^{125}I]$, $[^{131}I]$, $[^{3}H]$, $[^{14}C]$, etc. As the enzymes described above, stable enzymes with a high specific activity are preferred; for example, β-galactosidase, β-glucosidase, alkaline phosphatase, peroxidase, malate dehydrogenase and the like are used. Examples of the fluorescent substance used are fluorescamine, fluorescein isothiocyanate and the like. As the luminescent substances, there are employed, for example, luminol, luminol derivatives, luciferin, lucigenin and the like. Furthermore, the biotin-avidin system may also be used for binding an antibody or antigen to the label.

In the immobilization of antigens or antibodies, physical adsorption may be used. Alternatively, chemical binding that is conventionally used for immobilization of polypeptides, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, the immobilized monoclonal antibody of the present invention is reacted with a test fluid (primary reaction), then with a labeled form of another monoclonal antibody of the present invention (secondary reaction), and the activity of the labeling agent on the immobilizing carrier is assayed, whereby the amount of the receptor in the test fluid can be quantified. The order of the primary and secondary reactions may be reversed, and the reactions may be performed simultaneously or with some time intervals. The methods of labeling and immobilization can be performed by modifications of those methods described above. In the immunoassay by the sandwich method, the antibody used for immobilized or labeled antibody is not necessarily from one species, but a mixture of two or more species of antibodies may be used to increase the measurement sensitivity.

In the methods of the present invention for assaying the receptor of the present invention by the sandwich method, antibodies that bind to different sites of the receptor of the present invention are preferably used as the monoclonal antibodies of the present invention for the primary and secondary reactions. That is, in the antibodies used for the primary and secondary reactions, for example, when the antibody used in the secondary reaction recognizes the C-terminal domain of the receptor of the present invention, it is preferable to use the antibody capable of recognizing the region other than the C-terminal domain for the primary reaction, e.g., the antibody capable of recognizing the N-terminal domain.

The monoclonal antibody of the present invention can be used for the assay systems other than the sandwich method, for example, the competitive method, immunometric method, nephrometry, etc.

In the competitive method, an antigen in a test fluid and a labeled antigen are competitively reacted with an antibody, and the unreacted labeled antigen (F) and the labeled antigen bound to the antibody (B) are separated (B/F separation). The amount of the labeling agent in B or F is measured, and the amount of the antigen in the test fluid is quantified. This reaction method includes a liquid phase method using a soluble antibody as an antibody, polyethylene glycol for B/F separation and a secondary antibody, etc. to the soluble antibody, and an immobilized method either using an immobilized antibody as the primary antibody, or using a soluble antibody as the primary antibody and an immobilized antibody as the secondary antibody.

In the immunometric method, an antigen in a test fluid and an immobilized antigen are competitively reacted with a definite amount of labeled antibody, the immobilized phase is separated from the liquid phase, or an antigen in a test fluid is reacted with an excess amount of labeled antibody, the immobilized antigen is then added to bind the unreacted labeled antibody to the immobilized phase, and the immobilized phase is separated from the liquid phase. Then, the amount of the labeling agent in either phase is measured to quantify the antigen in the test fluid.

In the nephrometry, insoluble precipitates produced after the antigen-antibody reaction in gel or solution are quantified. Even when the amount of an antigen in a test fluid is small and only a small amount of precipitates is obtained, laser nephrometry using scattering of laser, or the like can be advantageously employed.

For applying these immunological assay methods to the quantification methods of the present invention, any particular conditions, procedures, etc. are not required. The assay systems for the receptor of the present invention may be constructed by adding ordinary technical consideration in the art to conventional conditions and procedures in the respective methods. For the details of these general technical means, reference can be made to the following reviews, texts, etc.

For example, reference can be made on Hiroshi Irie, ed. "Radioimmunoassay" (Kodansha, published in 1974), Hiroshi Irie, ed. "Sequel to the Radioimmunoassay" (Kodansha, published in 1979), Eiji Ishikawa, et al. ed. "Enzyme immunoassay" (Igakushoin, published in 1978), Eiji Ishikawa, et al. ed. "Immunoenzyme assay" (2nd ed.) (Igakushoin, published in 1982), Eiji Ishikawa, et al. ed. "Immunoenzyme assay" (3rd ed.) (Igakushoin, published in 1987), Methods in ENZYMOLOGY, Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected Immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (all published by Academic Press Publishing), etc.

As described above, the receptor of the present invention can be quantified with high sensitivity, by using the antibody of the present invention.

Furthermore, by quantifying the level of the receptor of the present invention using the antibody of the present invention, when an increased level of the receptor of the present invention is detected, it can be diagnosed that one suffers from diseases, for example, digestive tract (gastrointestinal) disorders, cancer, immune disorders, diabetes mellitus, etc., preferably digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity or the like, or it is highly likely that one would suffer from these diseases in the future. Also, when a decreased level of the receptor of the present invention is detected, it can be diagnosed that one suffers from diseases, for example, digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus or the like, or it is highly likely that one would suffer from these diseases in the future.

Besides, the antibody of the present invention can be used for detecting the receptor of the present invention present in test samples such as body fluids, tissues, etc. The antibody can also be used for preparation of antibody columns used to purify the receptor of the present invention, for detection of the receptor of the present invention in each fraction upon purification, for analysis of the behavior of the receptor of the present invention in cells under inspection; etc.

[4] Gene Diagnostic Agent

By using the polynucleotide (DNA) of the present invention, e.g., as a probe, an abnormality (gene abnormality) of the DNA or mRNA encoding the receptor of the present invention in human or other warm-blooded animal (e.g., rat, mouse, guinea pig, rabbit, fowl, sheep, swine, bovine, horse, cat, dog, monkey, etc.) can be detected. Therefore, the DNA of the present invention is useful as a gene diagnostic agent for damages to the DNA or mRNA, its mutation or decreased expression, or increased expression or overexpression of the DNA or mRNA.

The gene diagnosis described above using the DNA of the present invention can be performed by, for example, publicly known Northern hybridization or PCR-single-strand conformation polymorphism (PCR-SSCP) assay (Genomics, 5, 874-879 (1989); Proceedings of the National Academy of Sciences of the United States of America, 86, 2766-2770 (1989)), DNA microarray, etc.

For example, when overexpression of the receptor of the present invention is detected, it can be diagnosed that one suffers from diseases, for example, digestive tract (gastrointestinal) disorders, cancer, immune disorders, diabetes mellitus, etc., preferably digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, etc., or it is highly likely that one would suffer from these diseases in the future. Also, when reduced expression of the receptor of the present invention is detected, it can be diagnosed that one suffers from diseases, for example, digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus, etc., or it is highly likely that one would suffer from these diseases in the future.

[5] Medicament Comprising Antisense Polynucleotide (e.g., DNA)

The antisense polynucleotide (e.g., antisense DNA) that can bind complementarily to the polynucleotide (e.g., DNA) of the present invention to suppress expression of the polynucleotide (e.g., DNA) can be used as a low toxic and safe medicament including an agent for the prevention/treatment of diseases, for example, digestive tract (gastrointestinal) disorders, cancer, immune disorders, diabetes mellitus, etc., preferably as an agent for the prevention/treatment of digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, and so on.

For example, in the case of using the antisense DNA described above, the antisense DNA is administered solely, or the antisense DNA is inserted into an appropriate vector such as retrovirus vector, adenovirus vector, adenovirus-associated virus vector, etc., which is then administered in a conventional manner. The antisense DNA may be administered as it stands, or may be prepared into a dosage form together with a physiologically acceptable carrier such as an adjuvant to increase its uptake and administered by gene gun or through a catheter such as a catheter with a hydrogel.

In addition, the antisense DNA can also be employed as an oligonucleotide probe for diagnosis to examine the presence of the DNA of the present invention in tissues or cells and the state of its expression.

As in the antisense polynucleotide described above, the double-stranded RNA (siRNA (small (short) interfering RNA), shRNA (small (short) hairpin RNA), etc.) containing a part of the RNA encoding the receptor of the present invention, the ribozyme containing a part of the RNA encoding the receptor of the present invention, etc. can suppress the expression of the polynucleotide and can suppress the in vivo functions of the receptor of the present invention or the polynucleotide of the present invention and they can be used as low toxic and safe medicaments such as agents for the prevention/treatment of, for example, digestive tract (gastrointestinal) disorders, cancer, immune disorders, diabetes mellitus, etc., preferably as agents for the prevention/treatment of digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, and so on.

The double-stranded RNA can be manufactured by designing the same based on the sequence of the polynucleotide of the present invention, by modifications of publicly known methods (e.g., Nature, 411, 494, 2001).

The ribozyme can be manufactured by designing the same based on the sequence of the polynucleotide of the present invention, by modifications of publicly known methods (e.g., TRENDS in Molecular Medicine, 7, 221, 2001). For example, the ribozyme can be manufactured by ligating a publicly known ribozyme to a part of the RNA encoding the receptor of the present invention. The part of the RNA encoding the receptor of the present invention includes a contiguous part (RNA fragment) to the cleavage site on the RNA of the present invention, which can be cleaved by a publicly known ribozyme.

Where the double-stranded RNA or ribozyme described above is used as the agent for the prevention/treatment described above, the RNA or ribozyme can be prepared into pharmaceutical preparations, which are provided for administration, as in the antisense polynucleotide.

[6] Medicament Comprising Antibody of the Present Invention

The antibody of the present invention is useful as a low toxic and safe medicament, for example, as an agent for the treatment/prevention of digestive tract (gastrointestinal) disorders, cancer, immune disorders, diabetes mellitus, etc., preferably as an agent for the prevention/treatment of digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, and so on.

The medicament comprising the antibody of the present invention described above can be administered to human or other warm-blooded animal (e.g., rats, rabbits, sheep, swine, bovine, cats, dogs, monkeys, etc.) orally or parenterally, directly as a liquid preparation, or as a pharmaceutical composition in an appropriate dosage form. The dose may vary depending upon subject to be administered, target disease, conditions, route of administration, etc. When the antibody is used for the purpose of treating a patient with, e.g., colon cancer, it is advantageous to intravenously administer the antibody of the present invention normally at a single dose of about 0.01 to about 20 mg/kg body weight, preferably about 0.1 to about 10 mg/kg body weight, and more preferably about 0.1 to about 5 mg/kg body weight, approximately 1 to 5 times per day, preferably approximately 1 to 3 times per day. In other parenteral administration and oral administration, the antibody can be administered in a dose corresponding to the dose given above. When the condition is especially severe, the dose may be increased according to the condition.

The antibody of the present invention may be administered directly as it stands or as an appropriate pharmaceutical composition. The pharmaceutical composition used for the administration described above contains the aforesaid or salts thereof and pharmacologically acceptable carriers, diluents or excipients. Such a composition is provided in the dosage form suitable for oral or parenteral administration.

That is, examples of the composition for oral administration include solid or liquid dosage form, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration are injectable preparations, suppositories, etc. The injectable preparations may include dosage forms such as intravenous, subcutaneous, intracutaneous and intramuscular injections, drip infusions, etc. These injectable preparations may be prepared by methods publicly known. The injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mols) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule. The suppository used for rectal administration may be prepared by blending the aforesaid antibody or its salt with conventional bases for suppositories.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to 500 mg per dosage forms in a unit dose; especially in the form of injection, it is preferred that the aforesaid antibody is contained in about 5 to 100 mg and in about 10 to 250 mg for the other dosage forms.

Each composition described above may further contain other active components unless formulation causes any adverse interaction with the antibody described above.

[7] DNA Transgenic Animal

The present invention provides a non-human mammal bearing the DNA encoding the receptor of the present invention which is exogenous (hereinafter briefly referred to as the exogenous DNA of the present invention) or its variant DNA (sometimes briefly referred to as the exogenous variant DNA of the present invention).

That is, the present invention provides:

(1) A non-human mammal bearing the exogenous DNA of the present invention or its variant DNA;
(2) The mammal according to (1), wherein the non-human mammal is a rodent;
(3) The mammal according to (2), wherein the rodent is mouse or rat; and,
(4) A recombinant vector containing the exogenous DNA of the present invention or its variant DNA and capable of expressing in a mammal; etc.

The non-human mammal bearing the exogenous DNA of the present invention or its variant DNA (hereinafter briefly referred to as the DNA transgenic animal of the present invention) can be produced by transferring a desired DNA into an unfertilized egg, a fertilized egg, a spermatozoon, a germinal cell containing a primordial germinal cell thereof, etc., preferably in the embryogenic stage in the development of a non-human mammal (more preferably in the single cell or fertilized cell stage and generally before the 8-cell phase), by means, such as the calcium phosphate method, the electric pulse method, the lipofection method, the agglutination method, the microinjection method, the particle gun method, the DEAE-dextran method, etc. Also, it is possible to transfer the exogenous DNA of the present invention into a somatic cell, a living organ, a tissue cell, etc. by the DNA transfer, and utilize the transformant for cell culture, tissue culture, etc. In addition, these cells may be fused with the above-described germinal cell by a publicly known cell fusion method to prepare the DNA transgenic animal of the present invention.

Examples of the non-human mammals that can be used include bovine, swine, sheep, goat, rabbits, dogs, cats, guinea pigs, hamsters, mice, rats, etc. Above all, preferred are rodents, especially mice (e.g., C57B1/6 strain, DBA2 strain, etc. for a pure line and for a cross line, B6C3F$_1$ strain, BDF$_1$ strain B6D2F$_1$ strain, BALB/c strain, ICR strain, etc.), rats (Wistar, SD, etc.) or the like, since they are relatively short in ontogeny and life cycle from a standpoint of producing model animals for human disease.

"Mammal" in a recombinant vector that can be expressed in the mammal includes the aforesaid non-human mammal and human.

The exogenous DNA of the present invention refers to the DNA of the present invention that is once isolated/extracted from a mammal, not the DNA of the present invention inherently possessed by a non-human mammal.

The mutant DNA of the present invention includes mutants resulting from variation (e.g., mutation, etc.) in the base sequence of the original DNA of the present invention, specifically DNAs resulting from base addition, deletion, substitution with other bases, etc. and further includes abnormal DNA.

The abnormal DNA is intended to mean such a DNA that expresses the abnormal receptor of the present invention and exemplified by the DNA that expresses the polypeptide to suppress the function of normal receptor of the present invention.

The exogenous DNA of the present invention may be any one of those derived from a mammal of the same species as or a different species from the target animal. In transferring the DNA of the present invention, it is generally advantageous to use the DNA as a DNA construct in which the DNA is ligated downstream a promoter capable of expressing the DNA in the target animal. For example, in the case of transferring the human DNA of the present invention, a DNA transgenic mammal that expresses the DNA of the present invention to a high level, can be prepared by microinjecting a DNA construct (e.g., vector, etc.) of the human DNA of the present invention ligated downstream of various promoters which are capable of expressing the DNA derived from various mammals (e.g., rabbits, dogs, cats, guinea pigs, hamsters, rats, mice, etc.) bearing the DNA of the present invention highly homologous to the human DNA into a fertilized egg of the target non-human mammal, for example, a fertilized egg of a mouse.

As expression vectors for the receptor of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (i) promoters for DNA derived from viruses (e.g., simian virus, cytomegalovirus, Moloney leukemia virus, JC virus, breast cancer virus, poliovirus, etc.), and (ii) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle α actin, preproencephalin A, vasopressin, etc. Among them, cytomegalovirus promoters, human polypeptide elongation factor 1α (EF-1α) promoters, human and fowl β actin promoters, etc., which are capable of high expression in the whole body are preferred.

Preferably, the vectors described above have a sequence that terminates the transcription of the desired messenger RNA in the DNA transgenic animal (generally termed a terminator); for example, a sequence of each DNA derived from viruses and various mammals, and SV40 terminator of the simian virus, and the like are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal receptor of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using cDNA prepared by a publicly known method from RNA of liver, kidney, thyroid cell or fibroblast origin as a starting material. Also, an exogenous abnormal DNA can produce the translational region through variation of the translational region of the normal polypeptide obtained from the cells or tissues described above by point mutagenesis.

The translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transferred at the fertilized egg cell stage in a manner such that the DNA is certainly present in all the germinal cells and somatic cells of the target mammal. The fact that the exogenous DNA of the present invention is present in the germinal cells of the animal prepared by DNA transfer means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transferred can be passaged as the DNA-bearing animal under ordinary rearing environment, by confirming that the exogenous DNA is stably retained by crossing.

By transfer of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfer means that the DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

It is possible to obtain homozygous animals having the transferred DNA in both homologous chromosomes and breed male and female of the animal so that all the progeny have this DNA in excess.

In a non-human mammal bearing the normal DNA of the present invention, the normal DNA of the present invention has expressed at a high level, and may eventually develop hyperfunction in the function of the receptor of the present invention by promoting the function of endogenous normal DNA. Therefore, the animal can be utilized as a pathologic model animal for the disease. For example, using the normal DNA transgenic animal of the present invention, it is possible to elucidate the mechanism of hyperfunction in the function of the receptor of the present invention and the pathological mechanism of the disease associated with the receptor of the present invention and to investigate how to treat these diseases.

Furthermore, since a transgenic mammal with the exogenous normal DNA of the present invention exhibits a symptom of increasing the free receptor of the present invention, the animal is usable in a test for screening the agent for the prevention/treatment of diseases associated with the receptor of the present invention [e.g., digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], cancer (e.g., digestive cancer (e.g., gastric cancer, colon cancer, gastric MALT lymphoma, etc.), breast cancer, lung cancer, prostate cancer, esophageal cancer, pharyngeal cancer, liver cancer, biliary tract cancer, spleen cancer, renal cancer, bladder cancer, uterine cancer, testicular cancer, thyroid cancer, pancreatic cancer, brain tumor, ovary cancer, blood tumor, etc.), immune disorders [e.g., sepsis, atherosclerosis, AIDS, autoimmune disorders (e.g., chronic obstructive pulmonary disease, chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], type II diabetes mellitus II, obesity, etc.].

On the other hand, a non-human mammal having the exogenous abnormal DNA of the present invention can be passaged under normal breeding conditions as the DNA-bearing animal by confirming stable retention of the exogenous DNA via crossing. Furthermore, the exogenous DNA of interest can be utilized as a starting material after inserting the DNA into the plasmid described above. The DNA construct with a promoter can be prepared by conventional DNA engineering techniques. The transfer of the abnormal DNA of the present invention at the fertilized egg cell stage is preserved to be present in all of the germinal and somatic cells of the target mammal. The fact that the abnormal DNA of the present invention is present in the germinal cells of the animal after DNA transfer means that all of the offspring of the prepared animal have the abnormal DNA of the present invention in all of the germinal and somatic cells. Such an offspring that passaged the exogenous DNA of the present invention will have the abnormal DNA of the present invention in all of the germinal and somatic cells. A homozygous animal having the introduced DNA on both of homologous chromosomes can be acquired, and by crossing these male and female animals, all the offspring can be bred to retain the DNA.

In a non-human mammal bearing the abnormal DNA of the present invention, the abnormal DNA of the present invention has expressed to a high level, and may eventually develop the function inactive type inadaptability to the receptor of the present invention by inhibiting the functions of endogenous normal DNA. Therefore, the animal can be utilized as a pathologic model animal for the disease. For example, using the abnormal DNA transgenic animal of the present invention, it is possible to elucidate the pathological mechanism of the function inactive type inadaptability to the receptor of the present invention and to investigate how to treat the disease.

Specifically, the transgenic animal of the present invention expressing the abnormal DNA at a high level is expected to serve as an experimental model to elucidate the mechanism of the functional inhibition (dominant negative effect) of normal polypeptide or receptor by the abnormal polypeptide of the present invention or the abnormal receptor of the present invention in the function inactive type inadaptability of the receptor of the present invention.

A mammal bearing the abnormal exogenous DNA of the present invention has a symptom increasing the receptor of the present invention and is thus also expected to serve for screening a candidate drug for the treatment of the function inactive type inadaptability of the receptor of the present invention.

Other potential applications of two kinds of the DNA transgenic animals of the present invention described above further include, for example:

(i) use as a cell source for tissue culture;
(ii) elucidation of the relation to the polypeptide or receptor that is specifically expressed or activated by the receptor of the present invention, through direct analysis of DNA or RNA in tissues of the DNA transgenic animal of the present invention or through analysis of tissues of the polypeptide or receptor expressed by the DNA;
(iii) research on the function of cells derived from tissues that are usually cultured only with difficulty, using cells in tissues bearing the DNA cultured by a standard tissue culture technique;
(iv) screening a medicament that enhances the functions of cells using the cells described in (iii) above; and,
(v) isolation and purification of the variant polypeptide or the receptor of the present invention and preparation of an antibody thereto; etc.

Furthermore, clinical conditions of the diseases associated with the receptor of the present invention [e.g., digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], cancer (e.g., digestive cancer (e.g., gastric cancer, colon cancer, gastric MALT lymphoma, etc.), breast cancer, lung cancer, prostate cancer, esophageal cancer, pharyngeal cancer, liver cancer, biliary tract cancer, spleen cancer, renal cancer, bladder cancer, uterine cancer, testicular cancer, thyroid cancer, pancreatic cancer, brain tumor, ovary cancer, blood tumor, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], type II diabetes mellitus, obesity, etc.], including the function inactive type inadaptability to the receptor of the present invention, can be determined by using the DNA transgenic animal of the present invention. Also, pathological findings on each organ in a disease model associated with the receptor of the present invention can be obtained in more detail, leading to the development of a new method for treatment as well as the research and therapy of any secondary diseases associated with the diseases.

It is also possible to obtain a liberated DNA-transferred cell by excising each organ from the DNA transgenic animal of the present invention, mincing the organ and degrading with a proteinase such as trypsin, etc., followed by establishing the line of its culture or cultured cells. Furthermore, the DNA transgenic animal can serve to identify cells capable of producing the receptor of the present invention, and to study the relation to apoptosis, differentiation or proliferation or the mechanism of signal transduction in these properties to inspect any abnormality therein. Thus, the DNA transgenic animal can provide an effective research material for the receptor of the present invention and for investigation of its function and effect.

To develop medicaments for treating the diseases associated with the receptor of the present invention, including the function inactive type inadaptability to the receptor of the present invention, using the DNA transgenic animal of the present invention, an effective and rapid method for screening can be provided by using the method for inspection and the method for quantification, etc. described above. It is also possible to investigate and develop a method for DNA therapy for treating the diseases associated with the receptor of the present invention, using the DNA transgenic animal of the present invention or a vector capable of expressing the exogenous DNA of the present invention.

[8] Knockout Animal

The present invention provides a non-human mammalian embryonic stem cell bearing the DNA of the present invention inactivated and a non-human mammal deficient in expressing the DNA of the present invention.

Thus, the present invention provides:
(1) a non-human mammalian embryonic stem cell in which the DNA of the present invention is inactivated;
(2) the embryonic stem cell according to (1), wherein the DNA is inactivated by introducing a reporter gene (e.g., β-galactosidase gene derived from *Escherichia coli*);
(3) the embryonic stem cell according to (1), which is resistant to neomycin;
(4) the embryonic stem cell according to (1), wherein the non-human mammal is a rodent;
(5) the embryonic stem cell according to (4), wherein the rodent is mouse;
(6) a non-human mammal deficient in expressing the DNA of the present invention, wherein the DNA is inactivated;
(7) the non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;
(8) the non-human mammal according to (6), which is a rodent;
(9) the non-human mammal according to (8), wherein the rodent is mouse; and,
(10) a method of screening a compound or its salt that promotes or inhibits the activity of a promoter for the DNA of the present invention, which comprises administering a test compound to the mammal of (7) and detecting expression of the reporter gene.

The non-human mammalian embryonic stem cell in which the DNA of the present invention is inactivated refers to a non-human mammalian embryonic stem cell (hereinafter abbreviated as ES cell) that suppresses the ability of the non-human mammal to express the DNA by artificially mutating the DNA of the present invention, or the DNA has no substantial ability to express the receptor of the present invention (hereinafter sometimes referred to as the knockout DNA of the present invention) by substantially inactivating the activities of the receptor of the present invention encoded by the DNA.

Examples of the non-human mammal used are the same as those given above.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammalian embryonic stem cell, in which the DNA of the present invention is inactivated (hereinafter merely referred to as the ES cell with the DNA of the present invention inactivated or the knockout ES cell of the present invention), can be obtained by, for example, isolating the DNA of the present invention that the desired non-human mammal possesses, inserting a drug resistant gene such as a neomycin resistant gene or a hygromycin resistant gene, or a reporter gene such as lacZ (β-galactosidase gene) or cat (chloramphenicol acetyltransferase gene), etc. into its exon region thereby to disable the functions of exon, or integrating to a chromosome of the target animal by, e.g., homologous recombination, a DNA sequence that terminates gene transcription (e.g., polyA additional signal, etc.) in the intron between exons, thus inhibiting the synthesis of complete messenger RNA and eventually destroying the gene (hereinafter briefly referred to as a targeting vector). The thus-obtained ES cells to the southern hybridization analysis with a DNA sequence on or near the DNA of the present invention as a probe, or to PCR analysis with a DNA sequence on the targeting vector and another DNA sequence near the DNA of the present invention which is not included in the targeting vector as primers, to select the knockout ES cell of the present invention.

The parent ES cells to inactivate the DNA of the present invention by homologous recombination, etc. may be of a strain already established as described above, or may originally be established in accordance with a modification of the known method by Evans and Kaufman described above. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, for the purpose of obtaining a pure line of ES cells with the clear immunological genetic background instead of the ES cells of the 129 strain and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocysts at 3.5 days after fertilization are commonly used, and embryos are preferably collected at the 8-cell stage, after culturing until the blastocyst stage, the embryos are used to efficiently obtain a large number of early stage embryos.

Although the ES cells used may be of either sex, male ES cells are generally more convenient for generation of a germ cell line chimera. It is also desirable that sexes are identified as soon as possible to save painstaking incubation time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, whereas karyotype analysis requires about $10^6$ cells; therefore, the first selection of ES cells at the early stage of culture can be based on sex identification, and male cells can be selected early, which saves a significant amount of time at the early stage of culture.

Also, second selection can be achieved by, for example, confirmation of the number of chromosomes by the G-banding method. It is usually desirable that the chromosome number of the obtained ES cells be 100% of the normal number. However, when it is difficult to obtain the cells having the normal number of chromosomes due to physical operations, etc. in the cell establishment, it is desirable that the ES cell is again cloned to a normal cell (e.g., in a mouse cell having the number of chromosomes being 2n=40) after knockout of the gene of the ES cells.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably 5% carbon dioxide and 95% air, or 5% oxygen, 5% carbon dioxide and 90% air) in the presence of LIF (1 to 10000 U/ml) on appropriate feeder cells such as STO fibroblasts, treated with a trypsin/EDTA solution (normally 0.001 to 0.5% trypsin/0.1 to about 5 mM EDTA, preferably about 0.1% trypsin/1 mM EDTA) at the time of passage to obtain separate single cells, which are then plated on freshly prepared feeder cells. This passage is normally conducted every 1 to 3 days; it is desirable that cells be observed at the passage and cells found to be morphologically abnormal in culture, if any, be abandoned.

Where ES cells are allowed to reach a high density in mono-layers or to form cell aggregates in suspension under appropriate conditions, it is possible to differentiate the ES cells to various cell types, for example, pariental and visceral muscles, cardiac muscle, or the like [M. J. Evans and M. H. Kaufman, Nature, 292, 154, 1981; G R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtained from the differentiated ES cells of the present invention, are useful for cytological study of the receptor of the present invention in vitro.

The non-human mammal deficient in expression of the DNA of the present invention can be identified from a normal animal by measuring the mRNA level in the subject animal by a publicly known method, and indirectly comparing the degrees of expression.

Examples of the non-human mammal used are the same as those given above.

With respect to the non-human mammal deficient in expression of the DNA of the present invention, the DNA of the present invention can be made knockout by transferring a targeting vector, prepared as described above, to mouse embryonic stem cells or mouse oocytes, and conducting homologous recombination in which a targeting vector DNA sequence, wherein the DNA of the present invention is inactivated by the transfer, is replaced with the DNA of the present invention on a chromosome of a mouse embryonic stem cell or mouse embryo.

The knockout cells with the disrupted DNA of the present invention can be identified by the Southern hybridization analysis using as a probe a DNA fragment on or near the DNA of the present invention, or by the PCR analysis using as primers a DNA sequence on the targeting vector and another DNA sequence at the proximal region of other than the DNA of the present invention derived from mouse used in the targeting vector. When non-human mammal stem cells are used, a cell line wherein the DNA of the present invention is inactivated by homologous recombination is cloned; the resulting clones are injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal constructed with both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the receptor of the present invention. The individuals deficient in homozygous expression of the receptor of the present invention can be obtained from offspring of the intercross between those deficient in heterozygous expression of the receptor of the present invention.

When an oocyte is used, a DNA solution may be injected, e.g., into the prenucleus by microinjection thereby to obtain a transgenic non-human mammal having a targeting vector introduced in its chromosome. From such transgenic non-human mammals, those having a mutation at the locus of the DNA of the present invention can be obtained by selection based on homologous recombination.

As described above, the individuals in which the DNA of the present invention is rendered knockout permit passage rearing under ordinary rearing conditions, after the individuals obtained by their crossing have proven to have been knockout.

Furthermore, the genital system may be obtained and retained by conventional methods. That is, by crossing male and female animals each having the inactivated DNA, homozygous animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammalian embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the receptor of the present invention, such an animal can be a disease model suspected of inactivated biological activities of the receptor of the present invention and thus, offers an effective study to investigate the causes for and therapy for these diseases.

[8a] Method of Screening Compound that Promotes or Inhibits Activities of Promoter for the DNA of the Invention The present invention provides a method of screening a compound or its salt that promotes or inhibits the activity of a promoter for the DNA of the present invention, which comprises administering a test compound to a non-human mammal deficient in expression of the DNA of the present invention and detecting expression of the reporter gene.

In the screening methods described above, an animal in which the DNA of the present invention is inactivated by introducing a reporter gene and the reporter gene is expressed under control of a promoter for the DNA of the present invention is used as the non-human mammal deficient in expression of the DNA of the present invention, which is selected from the aforesaid non-human mammals deficient in expression of the DNA of the present invention.

Examples of the test compound are the same as those described above. The test compound may form salts and these salts for the test compound used are the same as those described above.

Examples of the reporter gene used are the same as those described above, and preferred are β-galactosidase (lacZ), soluble alkaline phosphatase gene, luciferase gene and the like.

Since the reporter gene is present under control of a promoter for the DNA of the present invention in the non-human mammal deficient in expression of the DNA of the present invention wherein the DNA of the present invention is substituted with the reporter gene, the activity of the promoter can be detected by tracing the expression of a substance encoded by the reporter gene.

When a part of the DNA region encoding the receptor of the present invention is substituted with, e.g., β-galactosidase gene (lacZ) derived from *Escherichia coli*, β-galactosidase is expressed in a tissue where the receptor of the present invention should originally be expressed, instead of the receptor of the present invention. Thus, the expression state of the receptor of the present invention can be readily observed with an animal in vivo by staining with a reagent, e.g., 5-bromo-4-chloro-3-indolyl-β-galactopyranoside (X-gal) which is a substrate for β-galactosidase. Specifically, a mouse deficient in the receptor of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. The β-galactosidase reaction is terminated by washing the tissue preparation with 1 mM EDTA/PBS solution, and the color formed is observed. Alternatively, mRNA encoding lacZ may be detected in a conventional manner.

The compound or its salt, which is obtained using the screening methods described above, is a compound selected from the test compounds described above, which promotes or inhibits the activity of a promoter for the DNA of the present invention.

The compound obtained by the screening methods may form salts, and examples of these salts used for the compound are the same as those for the test compounds described above.

The compound or its salt that promotes the activity of a promoter for the DNA of the present invention can promote the expression of the receptor of the present invention to promote the activity or function of the receptor of the present invention. Therefore, the compound or its salt can be used as a low toxic and safe medicament, such as an agent for the prevention/treatment of, for example, digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity, ulcer, etc.], type II diabetes mellitus, and the like.

The compound or its salt that inhibits the activity of a promoter for the DNA of the present invention can inhibit the expression of the receptor of the present invention to inhibit the activity or function of the receptor of the present invention, and can be used as a low toxic and safe medicament such as an agent for the prevention/treatment of, for example, digestive cancer (e.g., gastric cancer, colon cancer, gastric MALT lymphoma, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], obesity, and so on.

In addition, compounds derived from the compounds obtained by the screening described above can be used as well.

The medicament comprising the compound or its salt obtained by the above screening methods can be manufactured as in the medicament comprising the compound or its salt obtained by the screening methods of the present invention described above.

The pharmaceutical preparation thus obtained is safe and low toxic, and can be administered to, for example, human or other mammal (e.g., rat, mouse, guinea pig, rabbit, sheep, swine, bovine, horse, cat, dog, monkey, etc.).

The dose of the compound or its salt that promotes the activity of a promoter for the DNA of the present invention may vary depending on subject to be administered, target disease, conditions, route for administration, etc.; in oral administration of the compound for the treatment of, e.g., malabsorption syndrome, the compound is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the compound may vary depending on subject to be administered, target disease, conditions, route for administration, etc. When the compound is administered in the form of an injectable preparation for the treatment of, e.g., malabsorption syndrome, the compound is advantageously administered intravenously to an adult (as 60 kg body weight) normally at a daily dose of about 0.01 to about 30 mg, preferably about 0.1 to about 20 mg, and more preferably about 0.1 to about 10 mg. For other animal species, the corresponding dose as converted per 60 kg body weight can be administered.

On the other hand, the dose of the compound that inhibits the activity of a promoter for the DNA of the present invention may vary depending on subject to be administered, target disease, conditions, route for administration, etc.; in oral administration of the compound for the treatment of, e.g., colon cancer, the compound is administered to an adult (as 60 kg body weight) normally at a daily dose of about 0.1 mg to about 100 mg, preferably about 1.0 to about 50 mg, and more preferably about 1.0 to about 20 mg. In parenteral administration, the dose of the compound varies depending on subject to be administered, target disease, conditions, route for administration, etc. but when the compound is administered in the form of an injectable preparation for the treatment of, e.g., colon cancer, it is advantageous to intravenously administer the compound to an adult (as 60 kg body weight) at a daily dose of about 0.01 to about 30 mg, preferably about 0.1 to about 20 mg, and more preferably about 0.1 to about 10 mg. For other animal species, the corresponding dose as converted per 60 kg body weight can be administered.

As stated above, the non-human mammal deficient in expression of the DNA of the present invention is extremely useful for screening the compound or its salt that promotes or inhibits the activity of a promoter for the DNA of the present invention and can greatly contribute to elucidation of causes for various diseases derived from deficiency in expression of the DNA of the present invention and for the development of preventive/therapeutic drugs for these diseases.

Also, a so-called transgenic animal (gene transferred animal) can be prepared by using a DNA containing the promoter region of the receptor of the present invention, ligating genes encoding various proteins at the downstream and injecting the same into oocyte of an animal. It is thus possible to synthesize the polypeptide specifically and study its activity in vivo. When an appropriate reporter gene is ligated to the promoter site described above and a cell line that expresses the gene is established, the resulting system can be utilized as the search system for a low molecular compound having the action of specifically promoting or inhibiting (suppressing) in vivo productivity of the receptor of the present invention itself.

In the specification and drawings, where bases, amino acids, etc. are shown by their codes, these codes are denoted in accordance with the IUPAC-IUB Commission on Biochemical Nomenclature or by the common codes in the art, examples of which are given below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
I: inosine
R: adenine (A) or guanine (G)
Y: thymine (T) or cytosine (C)
M: adenine (A) or cytosine (C)
K: guanine (G) or thymine (T)
S: guanine (G) or cytosine (C)
W: adenine (A) or thymine (T)
B: guanine (G), guanine (G) or thymine (T)
D: adenine (A), guanine (G) or thymine (T)
V: adenine (A), guanine (G) or cytosine (C)
N: adenine (A), guanine (G), cytosine (C) or thymine (T), or unknown or other base
RNA: ribonucleic acid
mRNA: messenger ribonucleic acid
dATP: deoxyadenosine triphosphate
dTTP: deoxythymidine triphosphate
dGTP deoxyguanosine triphosphate
dCTP: deoxycytidine triphosphate
ATP: adenosine triphosphate
EDTA: ethylenediaminetetraacetic acid
SDS: sodium dodecyl sulfate
BHA: benzhydrylamine
pMBHA: p-methylbenzhydrylamine
Tos: p-toluenesulfonyl
Bzl: benzyl
Bom: benzyloxymethyl
Boc: t-butyloxycarbonyl
DCM: dichloromethane
HOBt: 1-hydroxybenztriazole
DCC: N,N'-dicyclohexylcarbodiimide
TFA: trifluoroacetic acid
DIEA: diisopropylethylamine
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine His or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid
Tyr (I): 3-iodotyrosine
DMF: N,N-dimethylformamide
Fmoc: N-9-fluorenylmethoxycarbonyl
Trt: trityl
Pbf: 2,2,4,6,7-pentamethyldihydrobenzofuran-5-sulfonyl
Clt: 2-chlorotrityl
$Bu^t$: t-butyl
Met (O): methionine sulfoxide Substituents, protecting groups and reagents frequently used in this specification are presented as the codes below.

[SEQ ID NO: 1]
This shows the amino acid sequence of human GPR35.

[SEQ ID NO: 2]
This shows the base sequence of cDNA encoding human GPR35 having the amino acid sequence represented by SEQ ID NO: 1.

[SEQ ID NO: 3]
This shows the base sequence of the sense strand primer used in REFERENCE EXAMPLE 1.

[SEQ ID NO: 4]
This shows the base sequence of the antisense strand primer used in REFERENCE EXAMPLE 1.

[SEQ ID NO: 5]
This shows the base sequence of Primer 1 used in EXAMPLE 5.

[SEQ ID NO: 6]
This shows the base sequence of Primer 2 used in EXAMPLE 5.

[SEQ ID NO: 7]
This shows the amino acid sequence of mouse GPR35.

[SEQ ID NO: 8]
This shows the base sequence of cDNA encoding mouse GPR35 having the amino acid sequence represented by SEQ ID NO: 7.

[SEQ ID NO: 9]
This shows the base sequence of Primer 1 used in EXAMPLE 6.

[SEQ ID NO: 10]
This shows the base sequence of Primer 2 used in EXAMPLE 6.

[SEQ ID NO: 11]
This shows the base sequence of Probe 1 used in EXAMPLE 6 [FAM (6-carboxy-fluorescein) was labeled at the 5' end as a reporter dye and TAMRA (6-carboxy-tetramethyl-rhodamine) at the 3' end as a quencher].

[SEQ ID NO: 12]
This shows the base sequence of Primer 3 used in EXAMPLE 6.

[SEQ ID NO: 13]
This shows the base sequence of Primer 4 used in EXAMPLE 6.

[SEQ ID NO: 14]
This shows the base sequence of Probe 2 used in EXAMPLE 6 [FAM (6-carboxy-fluorescein) was labeled at the 5' end as a reporter dye and TAMRA (6-carboxy-tetramethyl-rhodamine) at the 3' end as a quencher].

[SEQ ID NO: 15]
This shows the base sequence of Primer 1 used in EXAMPLE 7.

[SEQ ID NO: 16]
This shows the base sequence of Primer 2 used in EXAMPLE 7.

[SEQ ID NO: 17]
This shows the base sequence of Primer 3 used in EXAMPLE 7.

[SEQ ID NO: 18]
This shows the base sequence of Primer 4 used in EXAMPLE 7.

[SEQ ID NO: 19]
This shows the amino acid sequence of human GPR35-L1.

[SEQ ID NO: 20]
This shows the base sequence of cDNA encoding human GPR35-L1 having the amino acid sequence represented by SEQ ID NO: 19.

[SEQ ID NO: 21]
This shows the amino acid sequence of human GPR35-L2.

[SEQ ID NO: 22]
This shows the base sequence of cDNA encoding human GPR35-L2 having the amino acid sequence represented by SEQ ID NO: 21.

[SEQ ID NO: 23]
This shows the amino acid sequence of human GPR35-L3.

[SEQ ID NO: 24]
This shows the base sequence of cDNA encoding human GPR35-L3 having the amino acid sequence represented by SEQ ID NO: 23.

[SEQ ID NO: 25]
This shows the base sequence of Primer 1 used in REFERENCE EXAMPLE 2.

[SEQ ID NO: 26]
This shows the base sequence of Primer 2 used in REFERENCE EXAMPLE 2.

[SEQ ID NO: 27]
This shows the amino acid sequence of rat GPR35.

[SEQ ID NO: 28]
This shows the base sequence of cDNA encoding rat GPR35 having the amino acid sequence represented by SEQ ID NO: 27.

[SEQ ID NO: 29]
This shows the base sequence of the forward primer used in EXAMPLE 10.

[SEQ ID NO: 30]
This shows the base sequence of the reverse primer used in EXAMPLE 10.

[SEQ ID NO: 31]
This shows the base sequence of the probe used in EXAMPLE 10.

[SEQ ID NO: 32]

This shows the base sequence of the forward primer used in EXAMPLE 11.

[SEQ ID NO: 33]

This shows the base sequence of the reverse primer used in EXAMPLE 11.

[SEQ ID NO: 34]

This shows the base sequence of the probe used in EXAMPLE 11.

EXAMPLES

Hereinafter the present invention will be described in more detail by referring to REFERENCE EXAMPLES and EXAMPLES but is not deemed to be limited thereto.

DNQX represents 6,7-dinitroquinoxaline-2,3-dione.

NBQX represents 6-nitro-7-sulfamoylbenzo[f]quinoxaline-2,3-dione.

Reference Example 1

Human GPR35-Expressed CHO Cell Line

The DNA fragment encoding human GPR35 was acquired by PCR. Using 20 pmols each of two primers (SEQ ID NO: 3 and SEQ ID NO: 4), there was prepared 50 µl of a solution mixture containing 5 µl of 10×Advantage (registered trademark) 2 PCR Buffer (CLONTECH), 1 µl of 50×dNTP Mix (CLONTECH), 1 µl of 50×Advantage 2 Polymerase Mix (CLONTECH) and 1 µl of human hepatic cDNA solution (CLONTECH) as a template DNA. The reaction was carried out on a thermal cycler (GeneAmp (registered trademark) PCR system model 9700 (Applied Biosystems)), with a program of reaction at 96° C. for 1 minute, 35 cycles of one set to include 96° C. for 30 seconds, 63° C. for 40 seconds and 72° C. for 120 seconds, and extension at 72° C. for 10 minutes. After completion of the reaction, the reaction solution was electrophoresed on agarose gel to give a single product. The product was cloned using TA Cloning Kit (Invitrogen) to confirm the gene sequence. After a clone free from PCR error was subjected to double digestion with restriction enzymes SalI (Takara Shuzo) and ClaI (Takara Shuzo), the digestion product was electrophoresed on agarose gel to excise the single product. The resulting fragment (ca. 1 kb) was introduced into vector pAKKO-111 [Biochem. Biophys. Acta., 1219, 251 (1994)], which was transfected to CHO cells in a conventional manner to give the human GPR35-expressed CHO cell line.

Reference Example 2

Cloning of Rat GPR35

Using rat (SD) small intestine cDNA (Seegene) as a template, PCR was carried out using Primer 1 (SEQ ID NO: 25) and Primer 2 (SEQ ID NO: 26). Using Pyrobest DNA polymerase (Takara Shuzo), PCR was carried out by (1) reaction at 98° C. for 10 seconds, followed by (2) repeating 35 cycles of one set to include 98° C. for 10 seconds and 68° C. for 60 seconds, and (3) extension at 68° C. for 7 minutes. The amplified product was inserted into pCR-Blunt2-TOPO vector (Invitrogen), which was transfected to *Escherichia coli* JM109 (Takara Shuzo) and cloned. As a result of its base sequencing, the base sequence (SEQ ID NO: 27) of cDNA encoding rat GPR35 having the amino acid sequence represented by SEQ ID NO: 28 was obtained.

Example 1

Screening of Ligand to GPR35

The CHO-K1 cell line (purchased from ATCC) was incubated in HAM F-12 medium (Invitrogen) supplemented with 10% fetal calf serum, unless otherwise indicated. On the day before transfection, the cells were inoculated at $4.5\times10^5/10$ $cm^2$ and incubated at 37° C. for 15 hours or more in a $CO_2$ incubator adjusted to 5% $CO_2$ concentration. Using Lipofectamine reagent (Invitrogen), transfection was performed according to modifications of the procedure attached to the reagent. When a 6-well plate was used as the incubator, the transfection was performed as follows. Two tubes each having a 1.5 ml volume were prepared and 100 µl each of Opti-MEM medium (Invitrogen) was dispensed in each tube. Next, 1 µg of the GPR35 expression vector obtained in REFERENCE EXAMPLE 1 and 0.5 µg of Gα15 expression vector (Guthrie cDNA Resource Center) were incorporated into one tube and in another tube, 6 µl of Lipofectamine reagent was charged, which were then mixed together. The mixture was settled for 20 minutes at room temperature. To the solution, 800 µl of Opti-MEM medium was added and the resulting solution mixture for transfection was added to the CHO-K1 cells, which had been previously washed with Opti-MEM medium. The cells were then incubated in a $CO_2$ incubator for 6 hours. After the incubation, the cells were rinsed with PBS (Invitrogen), then detached by 0.05% trypsin-EDTA solution (Invitrogen) and recovered by centrifugal operation. The cells obtained were counted and diluted to $5\times10^4$ cells per 100 µl of the medium. The dilution was dispensed to a black walled 96-well plate (Costar) at 100 µl per well, followed by incubation overnight in a $CO_2$ incubator. Various test samples were added to the CHO-K1 cells, in which the receptor was transiently expressed, by the transfection procedure described above, whereby changes in intracellular calcium levels were assayed on a FLIPR (Molecular Device).

To assay the changes in intracellular calcium levels on FLIPR, the following pretreatment was made. First, an assay buffer was prepared to add fluorescence dye Fluo-3AM (DOJIN) to the cells, or to wash the cells immediately before the FLIPR assay. A solution was prepared by adding 20 ml of 1M HEPES (pH 7.4) (DOJIN) to 1000 ml of HBSS (Invitrogen) (hereinafter HBSS/HEPES solution). To the solution, there was added 10 ml of a solution obtained by dissolving 710 mg of Probenecid (Sigma) in 5 ml of 1N NaOH and further adding 5 ml of HBSS/HEPES solution thereto and mixing them. The resulting solution was used as an assay buffer. Next, 50 µg of Fluo-3AM was dissolved in 21 µl of DMSO (DOJIN), and an equal volume of 20% pluronic acid (Molecular Probes) was added to the solution. After mixing them, the mixture was added to 10.6 ml of an assay buffer supplemented with 105 µl of fetal calf serum to give a fluorescence dye solution. After the medium for the transfected CHO-K1 cells was removed, the fluorescence dye solution was immediately dispensed at 100 µl each per well and incubation was carried out in a $CO_2$ incubator for an hour to take up the fluorescence dye into the cells. The incubated cells were washed with the assay buffer described above and set on FLIPR. Test samples to be added to the receptor-expressed CHO-K1 cells were prepared using the assay buffer and simultaneously set on FLIPR.

After the pretreatment described above was made, changes in intracellular calcium levels by the addition of various test samples were assayed on FLIPR.

Figure 2:
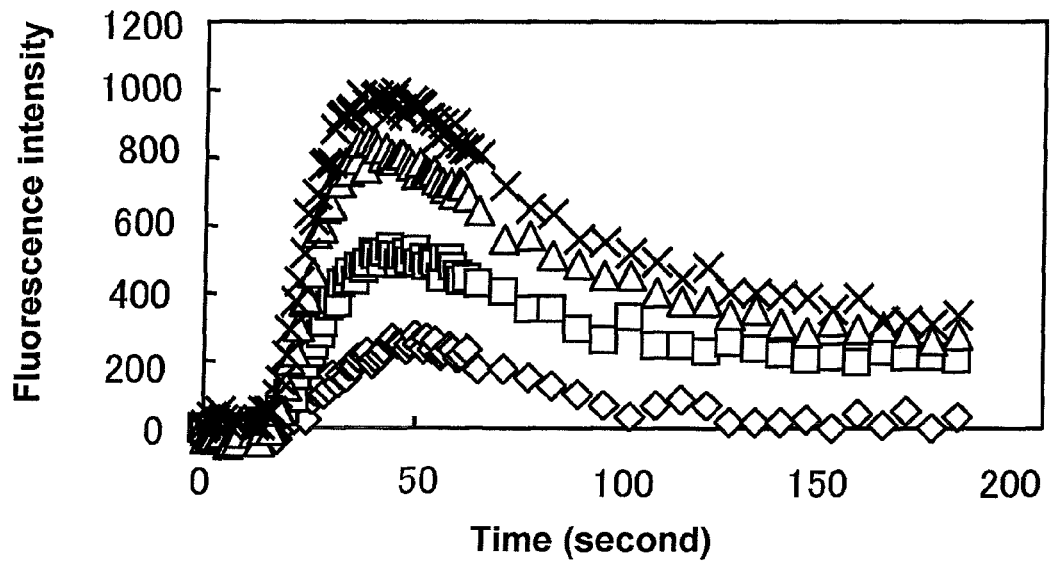
FIG. 2 shows the results of assaying changes in intracellular $Ca^{2+}$ levels when ellagic acid was added to CHO-K1 cells expressing GPR35 and Gα15. In the figure, the ordinate denotes fluorescence intensity showing the intracellular $Ca^{2+}$ level, the abscissa denotes time lapse (second) after the start of measurements and symbols ◇(open diamond), □(open square), △(open triangle) and X denote 0.3 µM ellagic acid, 1.0 µM ellagic acid, 3.0 µM ellagic acid and 10 µM ellagic acid, respectively.

The results reveal that the CHO-K1 cells co-expressing GPR35 and Gα15 dose-dependently responded (increased intracellular calcium levels) when DNQX (FIG. 1), ellagic acid (FIG. 2), 6-cyano-7-nitroquinoxaline-2,3-dione, NBQX and 5,7-dinitroquinoxaline-2,3-dione were added. Such response was not observed with control CHO-K1 cells, in which only expression vector pAKKO-111H (Biochem. Biophys. Acta., 1219, 251, 1994) was introduced.

Example 2

Suppression by DNQX and NBQX of Intracellular cAMP Levels Increased by Forskolin Addition in Human GPR35-Expressed CHO Cell Line The human GPR35-expressed CHO cells obtained in REFERENCE EXAMPLE 1 were washed with an assay buffer (HBSS (Gibco/BRL) supplemented with 0.1% bovine serum albumin and 0.2 mM isobutylmethylxanthine), followed by incubation at 37° C. for 30 minutes under conditions of 5% $CO_2$. DNQX and NBQX were diluted with the assay buffer and the dilutions were added to the cells at respective concentrations. Thereafter forskolin was added to become 2 µM. Incubation was performed at 37° C. for 30 minutes under conditions of 5% $CO_2$. The culture supernatant was discarded and the intracellular cAMP level was assayed on a plate reader (EnVision, Perkin Elmer) in accordance with the protocol of cAMP Screen Kit (Applied Biosystems).

Figure 3:
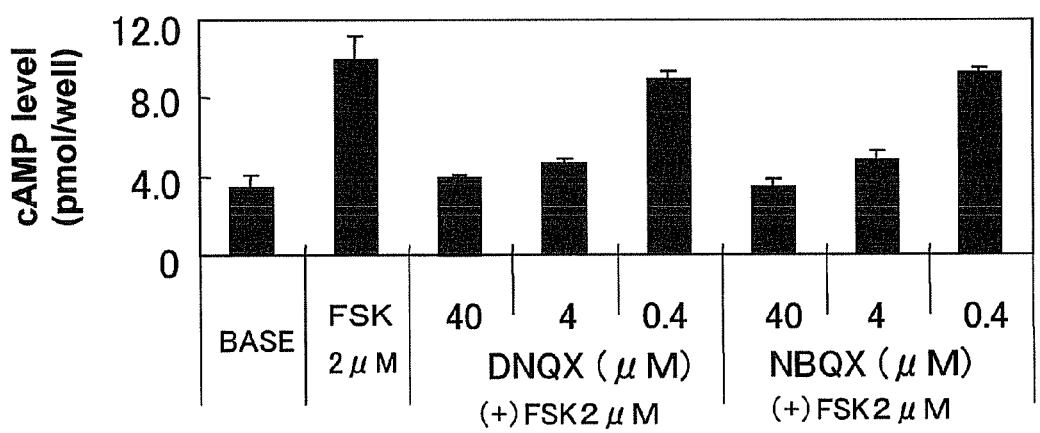
FIG. 3 shows the results of assaying activities of suppressing the intracellular cAMP levels in CHO cells bearing stably expressed GPR35, which levels were increased by forskolin stimulation, by the addition of DNQX and NBQX. In the figure, the ordinate denotes cAMP levels (pmol/well) and the abscissa denotes the respective amounts of forskolin (FSK), DNQX and NBQX added.

As a result, a dose-dependent and specific decrease of the intracellular cAMP levels by DNQX and NBQX, which had been increased by forskolin addition, was detected only in the human GPR35-expressed CHO cell line (FIG. 3).

The results reveal that activation of GPR35 by the agonist results in decreased intracellular cAMP levels. It is known that cAMP serves in cells as one of the major signal transduction substances and brings about various changes in cells. It is thus possible to improve various pathological conditions by regulating the intracellular cAMP levels by an agonist to GPR35 (having the action of decreasing the cAMP levels) or an antagonist to GPR35 (having the action of increasing the cAMP levels).

Example 3

Enhanced MAPK Phosphorylation

The human GPR35-expressed CHO cells prepared in REFERENCE EXAMPLE 1 were incubated for 48 hours in a 12-well plate at $5 \times 10^4$ cells/well. MEMα (containing no nucleic acid) supplemented with 10% dialyzed FBS was used as a medium. After the medium was removed by suction, the cells were washed with 1 ml (×2) of serum-free medium and 500 µl of the serum-free medium was added thereto, followed by incubation at 37° C. for 16 hours. DNQX or NBQX was added to the cells at its optimum concentration, followed by incubation at 37° C. for 5 minutes. Immediately after the medium was removed by suction, 50 µl of Blue Loading Buffer (BioLabs) was added, the cells were lysed and taken up by pipetting. The cell lysate was destructed using a sonicator (Sono Cleaner; KAIJO DENKI) and then heat-treated at 95° C. for 5 minutes. Centrifugation (15,000 rpm, 4° C., 5 minutes) was made and the supernatant was used as a final sample.

After 10 µl of the sample was electrophoresed on 10% SDS-PAGE, the sample was transferred to a PVDF membrane by western blotting. The membrane was immersed in Block Ace (manufactured by Dainippon Pharmaceutical Co., Ltd.) and then shaken for an hour at room temperature. The membrane was immersed in Block Ace (diluted to 1/2000) containing a primary antibody (Phospho-p44/42 Map Kinase antibody; Cell Signaling) and shaken for an hour at room temperature. The membrane was immersed in TBS-Tween 20 (50 mM Tris-HCl (pH 7.6), 150 mM NaCl, 0.05% Tween-20), shaken for 5 minutes (×2) and then washed. The membrane was immersed in a HRP-labeled secondary antibody (Goat Anti-Rabbit IgG, HRP-conjugate; upstate), which was diluted in TBS-Tween 20 (diluted to 1/5000), and shaken for an hour at room temperature. The membrane was immersed in TBS-Tween 20, shaken for 10 minutes (×3) and then washed. The membrane was applied to a fluorescence detector (LAS-1000; FUJI FILM) in accordance with the protocol of ECLplus Western Blotting System (Amersham Biosciences). By stimulation with 1-5 µM DNQX or NBQX, the level of phosphorylated MAP-kinase in the human GPR35 receptor-expressed CHO cells was enhanced. In control cells (human TGR23-expressed CHO cells prepared by a known method), any enhanced level of phosphorylation was not observed.

Example 4

Internalization of GPR35-GFP Fusion Protein Expressed on CHO Cells by Addition of DNQX and NBQX The CHO cell line, in which a protein wherein GFP was fused to the C-terminus of human GPR35 was stably expressed, was established using an expression plasmid for animal cells by publicly known methods. In assaying internalization of the protein, the cells at growth phase were plated at the concentration of 40000 cells/well on a 96-well plate (Packard, View-Plate™-96, Black), and cultured overnight at 37° C. under 5% $CO_2$. First, the cells in the well were washed with assay buffer (HBSS (Gibco/BRL) supplemented with 0.1% bovine serum albumin (BSA)). Then, 100 µl each of the assay buffers containing 3 µM, 10 µM and 30 µM DNQX and NBQX was added to each well, followed by incubation at 37° C. under conditions of 5% $CO_2$. Subsequently, 100 µl/well of a cell fixation solution (4% paraformaldehyde-containing PBS (free of Ca/Mg)) was added to the well, which was allowed to stand at room temperature for 30 minutes. The cell fixation solution was removed. After the cells were washed with Ca/Mg-free PBS, 50 µl/well of a labeling solution (3.13 µg/ml wheat germ aggulutinin (Molecular Probes, W-849), 5 µg/ml Hoechst-containing, Ca/Mg-free PBS) was added thereto, and the mixture was allowed to stand at room temperature for 20 minutes. After the labeling solution was removed, the cells were washed with Ca/Mg-free PBS (200 µl/well), and made a substitution of the same solution (200 µl/well). Then the surface of the plate was sealed, and analysis was immediately performed using Cellomics ArrayScan System (Cellomics). The intracellular localization of GPR35-GFP fusion protein was assessed using MemCyto Above Threshold (cell ratio (unit %) over a specific parameter (MemCyto Intensity Ratio) representing the ratio of membrane/cytoplasmic localization of the protein to all cells in the well), which is one of the parameters of the GPCR Signaling Assay Protocol attached to the above system.

As a result, when DNQX and NBQX were added, the activity of inducing dose-dependent internalization of the GPR35-GFP protein (decreased MemCyto Above Threshold value) was detected within the concentration range described above.

Example 5

Cloning of Mouse GPR35 and Analysis of Species Difference

Total RNA was prepared from the mouse (C57BL/6) colon using Isogen (Nippon Gene), and cDNA was synthesized using SuperScript II Reverse Transcriptase (Invitrogen). Using the cDNA as a template, PCR was carried out using Primer 1 (SEQ ID NO: 5) and Primer 2 (SEQ ID NO: 6). Using Pyrobest DNA polymerase (Takara Shuzo), PCR was performed by (1) reaction at 94° C. for 10 seconds, followed by amplification of (2) 3 cycles of one set to include 94° C. for 10 seconds and 68° C. for 90 seconds, (3) 3 cycles of one set to include 94° C. for 10 seconds, 62° C. for 30 seconds and 68° C. for 60 seconds, (4) 35 cycles of one set to include 94° C. for 10 seconds, 56° C. for 30 seconds and 68° C. for 90 seconds, and (5) extension at 68° C. for 7 minutes. Advantage 2 Polymerase Mix (Clontech) was further added thereto. After reacting at 72° C. for 10 minutes, the amplified product was inserted into pCR2.1-TOPO (Invitrogen), then introduced into *Escherichia coli* JM109 (Takara Shuzo) and cloned. As a result of its base sequencing, the base sequence (SEQ ID NO: 8) of cDNA encoding mouse GPR35 having the amino acid sequence represented by SEQ ID NO: 7 was acquired. After this plasmid was digested with restriction enzymes Sal I and Spe I, the digestion product was inserted into plasmid vector pAKKO-111H [Biochem. Biophys. Acta., 1219, 251 (1994)] to construct the expression vector. This expression vector was transfected to CHO-K1 cells by a modification of the procedure described in EXAMPLE 1. The reactivities with DNQX and ellagic acid were studied using FLIPR. As a result, mouse GPR35 was found to be responsive to these compounds as human GPR35 was.

Example 6

Analysis of Tissue Distribution of GPR35mRNA by RT-PCR

To analyze the gene expression distribution in human, cDNAs were synthesized from polyA+RNA (Clontech, Inc.) derived from various human tissues by the following procedure and used as templates.

Following the manual attached, the reaction was carried out at 42° C. using 1 μg of RNA, a random primer and SuperScriptII reverse transcriptase (Invitrogen). After the reaction was completed, ethanol precipitation was performed and the precipitates were dissolved in 100 μl. RT-PCR was carried out using Sequence Detection System Prism 7700 (Applied Biosystems), where Primer 1 (SEQ ID NO: 9) and Primer 2 (SEQ ID NO: 10) as well as Probe 1 (SEQ ID NO: 11) (Fam-ctccccgtgctaaggcccacaaa-Tamra) were used. For the RT-PCR solution, 0.05 μl each of the 100 μM primer solutions, 0.5 μl of 5 μM Probe 1 and 0.5 μl of the cDNA solution prepared above were added to 12.5 μl of TaqMan Universal PCR Master Mix (PE Biosystems), and distilled water was added thereto to make the total volume of the reaction solution 25 μl. PCR was carried out by reacting at 50° C. for 2 minutes and 95° C. for 10 minutes, followed by repeating 40 cycles of one set to include 95° C. for 15 seconds and 60° C. for 1 minute. The results reveal that human GPR35 was highly expressed in digestive tracts such as stomach, small intestine, large intestine, etc., dorsal root ganglion (DRG), hypophysis, testis, colon cancer cell lines such as Colo201, Colo205, SW1417, SW837, SW1463, WiDr, etc.

To analyze the expression in mouse, cDNAs were synthesized from total RNA derived from various mouse tissues by the following procedure and used as templates.

Following the manual attached, the reaction was carried out at 42° C. using 1 μg of RNA, a random primer and SuperScriptII reverse transcriptase (Invitrogen). After the reaction was completed, ethanol precipitation was performed and the precipitates were dissolved in 100 μl. RT-PCR was carried out using Sequence Detection System Prism 7700 (Applied Biosystems), where Primer 3 (SEQ ID NO: 12) and Primer 4 (SEQ ID NO: 13) as well as Probe 2 (SEQ ID NO: 14) (Fam-ctgcccgagacaccttcagccgt-Tamra) were used. For the RT-PCR solution, 0.05 μl each of the 100 μM primer solutions, 0.5 μl of 5 μM Probe 2 and 0.5 μl of the cDNA solution prepared above were added to 12.5 μl of TaqMan Universal PCR Master Mix (PE Biosystems), and distilled water was added thereto to make the total volume of the reaction solution 25 μl. PCR was carried out by reacting at 50° C. for 2 minutes and 95° C. for 10 minutes, followed by repeating 40 cycles of one set to include 95° C. for 15 seconds and 60° C. for 1 minute.

The results reveal that mouse GPR35 mRNA was highly expressed in digestive tracts such as stomach, small intestine, large intestine, etc., dorsal root ganglion (DRG), trachea, spleen, bone marrow, testis, ovary, 3T3-L1 after the induction of adipocyte differentiation, white adipocytes, colon cancer cell lines such as CE-2, BF, etc.

Example 7

Preparation of Splicing Variant of Human GPR35

Three variants of human GPR35, namely, GPR35-L1, GPR35-L2 and GPR35-L3, were cloned by PCR using two primers specific to the respective base sequences: Primer 1 (SEQ ID NO: 15) and Primer 2 (SEQ ID NO: 16) were used as primers for cloning of GPR35-L1, Primer 3 (SEQ ID NO: 17) and Primer 2 (SEQ ID NO: 16) as primers for cloning of GPR35-L2, and Primer 4 (SEQ ID NO: 18) and Primer 2 (SEQ ID NO: 16) as primers for cloning of GPR35-L3. Using human colon cDNA (Clontech) as a template, PCR was carried out using the respective primers. Using Pyrobest DNA polymerase (Takara Shuzo), PCR was carried out by (1) reaction at 98° C. for 1 minute, followed by amplification of (2) 35 cycles of one set to include 98° C. for 10 seconds, 60° C. for 30 seconds and 72° C. for 90 seconds, and (3) extension at 72° C. for 5 minutes. After completion of the reaction, the amplified product was inserted into pCR-Blunt II-TOPO (Invitrogen), which was then transfected to *Escherichia coli* JM109 (Takara Shuzo) and cloned. As a result of their base sequencing, the base sequence (SEQ ID NO: 20) of cDNA encoding the amino acid sequence (human GPR35-L1) represented by SEQ ID NO: 19, the base sequence (SEQ ID NO: 22) of cDNA encoding the amino acid sequence (human GPR35-L2) represented by SEQ ID NO: 21, and the base sequence (SEQ ID NO: 24) of cDNA encoding the amino acid sequence (human GPR35-L3) represented by SEQ ID NO: 23 were acquired, respectively. After the plasmids were digested with restriction enzymes Sal I and Spe I, the digested products were inserted into plasmid vector pAKKO-111H [Biochem. Biophys. Acta., 1219, 251 (1994)] to construct expression vectors.

In the human GPR35-L1 protein, 31 amino acid residues are added to the N terminus of the human GPR35 protein; 41 amino acid residues are added to the N terminus of human GPR35 protein in the human GPR35-L2 protein; and 85 amino acid residues are added to the N terminus of human GPR35 protein in the human GPR35-L3 protein.

Example 8

Preparation of Cells with Stably Co-Expressed Gα16 and GPR35 and Confirmation of Reactivity The Gα16-stably expressed cell line (Gα16/CHO cell line) as a host cell was prepared by transfecting the Gα16 expression vector (Guthrie cDNA Resource Center) into CHO cells in a conventional manner and incubating at 37° C. under 5% $CO_2$ in αMEM medium (containing nucleic acid; Invitrogen) supplemented with 10% fetal calf serum (Invitrogen), 50 units/ml penicillin/50 ug/ml streptomycin (CAMBREX) and 1 mg/ml geneticin (Invitrogen). The cells that were incubated for 2 days in αMEM medium (containing nucleic acid) supplemented only with 10% fetal calf serum charged in a 75 $cm^2$ flask were used for the transfection. The transfection was carried out using Lipofectamine reagent (Invitrogen) by a modification of the protocol attached to the reagent. First, 2 centrifuge tubes each having a 15 ml volume were prepared and 600 μl each of Opti-MEM medium (Invitrogen) was dispensed in each tube. Next, 4.8 μg of the expression vector was charged in one tube and in another tube 36 μl of Lipofectamine reagent was charged, which were mixed together. The mixture was settled for 20 minutes at room temperature. To the solution, 6 ml of Opti-MEM medium was added and the resulting solution mixture for transfection was added to the Gα16/CHO cells, which had been previously washed with Opti-MEM medium, followed by incubation in a $CO_2$ incubator (5% $CO_2$, 37° C.) for 5 hours. After the incubation, the cells were rinsed with PBS (Invitrogen), then detached using 0.05% trypsin-EDTA solution (Invitrogen) and recovered by centrifugal operation. The cells obtained were counted and diluted with αMEM medium (containing no nucleic acid; Invitrogen) supplemented only with 10% dialyzed fetal calf serum to have 0.3, 1.5 and 7.5 cells per 100 μl of the medium. The dilution was dispensed into a 96-well plate (FALCON) in 100 μl each per well, followed by incubation overnight in a $CO_2$ incubator. On the following day, the culture supernatant was removed. Then, αMEM medium (containing no nucleic acid; Invitrogen, this medium was used for the following incubation) containing 200 μl/well of 10% dialyzed fetal calf serum (Invitrogen), 50 units/ml penicillin/50 ug/ml streptomycin (CAMBREX) and 1 mg/ml geneticine (Invitrogen) was added, followed by further incubation for about 2 weeks. The wells which produced one colony per well were selected under microscope and the culture supernatant was removed. After rinsing with PBS containing 1 g/l EDTA, the detached cells were transferred to a 24-well plate charged with 1 ml/well of the medium. The grown cells were gradually transferred to a 25 $cm^2$ flask and then to a 75 $cm^2$ flask.

The thus obtained CHO cell line in which human GPR35 and Gα16 were co-expressed was diluted to $3 \times 10^4$ cells/100 μl. The dilution was dispensed to a black walled 96-well plate (Costar) at 100 μl per well, followed by incubation overnight in a $CO_2$ incubator. Following the procedure described in EXAMPLE 1, changes in intracellular calcium levels were assayed on FLIPR (Molecular Device). It was confirmed that the intracellular calcium levels were increased by addition of DNQX and ellagic acid.

Example 9

Screening of Agonist to GPR35 Using FLIPR

The cells obtained in EXAMPLE 8 above, in which Gα16 and GPR35 were stably co-expressed, are suspended in a medium (αMEM medium (containing no nucleic acid, Invitrogen) supplemented with 10% dialyzed fetal calf serum (Invitrogen), 50 units/ml penicillin/50 ug/ml streptomycin (CAMBREX) and 1 mg/ml geneticin (Invitrogen)) to have $3 \times 10^5$ cells/ml, respectively. Using an 8-channel pipette, the cells are inoculated at 100 μl each per well on a 96-well plate for FLIPR (Black plate clear bottom, Costar) ($3.0 \times 10^4$ cells/100 μl/well) and incubated overnight at 37° C. in a 5% $CO_2$ incubator, which is used for the following assay (hereinafter referred to as the cell plate). Twenty milliliters of H/HBSS (9.8 g of Nissui HANKS 2 (Nissui Pharmaceutical Co., Ltd.), 0.35 g of sodium hydrogencarbonate and 4.77 g of HEPES; adjusted to pH 7.4 with 6 M sodium hydroxide solution followed by sterilization through a sterilizing filter), 200 μl of 250 mM Probenecid and 200 μl of fetal bovine serum (FBS) are mixed with one another. Also, 2 vials (50 μg) of Fluo 3-AM (Dojin Chemical Laboratory, Ltd.) are dissolved in 40 μl of dimethylsulfoxide and 40 μl of 20% Pluronic acid (Molecular Probes), and the resulting solution is added to the H/HBSS-Probenecid-FBS described above. After mixing, the medium is removed from the cell plate using an 8-channel pipette, and 100 μl each of the mixture is dispensed into each well of the cell plate, followed by incubation at 37° C. for an hour in a 5% $CO_2$ incubator (dye loading).

A solution containing a test compound is added to 220 μl of H/HBSS containing 2.5 mM Probenecid and 0.1% CHAPS or H/HBSS containing 2.5 mM Probenecid, 0.1% CHAPS and 0.2% BSA for dilution. The dilution is then transferred to a 96-well plate (V-Bottom Plate, Coster) for FLIPR (hereinafter referred to as the sample plate). After completion of the dye loading onto the cell plate, the cell plate is washed with a wash buffer of H/HBSS supplemented with 2.5 mM Probenecid, using a plate washer (ELX405, Bio-Tek Instruments). After washing, 100 μl of the wash buffer is left. This cell plate and the sample plate are set on FLIPR (50 μl of sample is transferred from the sample plate to the cell plate by FLIPR) to determine changes in fluorescence intensity with passage of time, thereby to assay the intracellular calcium ion level increasing activity. The same test as described above is conducted using CHO cells, in which no GPR35 is expressed, or CHO cell lines in which control receptors such as histamine H1 receptor, GPR40 receptor, TGR7 receptor, etc. are expressed, to screen compounds capable of specifically increasing the intracellular calcium ion levels in the Gα16 and GPR35-stably co-expressed cells.

Example 10

Selective Gene Expression of GPR35 in Rat Intestinal Mucosa Layer

To clarify whether the site of GPR35 gene expression in the intestinal tract is the mucosa layer or the muscle layer, GPR35 gene expression levels in the rat ileal mucosa layer and muscle layer isolated by the microdissection method were assayed by the TaqMan method, respectively. Male SD (IGS) rat of 11 weeks old was decapitated to bleed under ether anestheisa. The isolated ileum was frozen and embedded in O.C.T. compound under cooling in liquid nitrogen. A fresh frozen section of 10 µm was prepared on an exclusive film-covered slide glass (Leica: 90FOIL-SL25) using a cryostat and the section was then dried in the cryostat (−20° C.). After the section was gradually accustomed to room temperature, it was fixed for 3 minutes in ice-cooled ethanol containing 5% acetic acid. The section was washed with ice-cooled RNase-Free water, then stained with ice-cooled 0.05% toluidine blue for 20 seconds and further washed with ice-cooled RNase-Free water. After cold air drying with a drier, the slide was stored at 4° C. immediately before microdissection. Using Leica Laser Microdissection System (LMD), the muscle layer and the mucosa layer were recovered from 4 tissue sections of about 1 cm$^2$ into tubes previously charged with ISOGEN, respectively. Total RNAs were purified from ISOGEN extracts of the muscle layer and the mucosa layer and 18 µl each of the total RNA solutions were finally obtained. After 10 µl of the RNA solution and 1 µl of 200 ng/µl random primer were kept warm at 70° C. for 10 minutes and then ice-cooled, 1 µl of SuperScriptII reverse transcriptase (Invitrogen), 4 µl of a buffer attached to the reverse transcriptase, 2 µl of 0.1 M dithiothreitol solution, 1 µl of 10 mM deoxynucleotide mixture and 1 µl of ribonuclease inhibitor RNaseOUT (Invitrogen) were added to make the total volume 20 µl. The reverse transcription was carried out under the following conditions. The reaction solution was kept warm successively at 25° C. for 10 minutes, 42° C. for 50 minutes, 70° C. for 15 minutes and 4° C. for 5 minutes to give a reverse-transcribed cDNA solution.

The expressed copy numbers of rat GPR35 gene and rat GAPDH gene as the internal standard were determined by the TaqMan PCR method. The reaction solution for the TaqMan PCR to determine the rat GPR35 gene consisted of 10 µl of reverse transcribed cDNA solution or 1 µl of the standard rat GPR35 DNA having various concentrations, 0.2 µM synthetic DNA forward primer (SEQ ID NO: 29), 0.2 µM synthetic DNA reverse primer (SEQ ID NO: 30), 0.2 µM rat GPR35 TaqMan probe (SEQ ID NO: 31) and TaqMan Universal PCR Master Mix (Applied Biosystems). The total volume of the reaction solution was 25 µl. The reaction solution for the TaqMan PCR to determine the rat GAPDH gene consisted of 10 µl of reverse transcribed cDNA solution or 1 µl of standard rat GAPDH DNA having various concentrations, synthetic DNA forward primer, synthetic DNA reverse primer and rat GAPDH probe attached to Rodent GAPDH Gene Assay Kit (Applied Biosystems) as well as TaqMan Universal PCR Master Mix (Applied Biosystems). The total volume of the reaction solution was 25 µl. The PCR reaction was performed using ABI PRISM 7700 Sequence Detector System (Applied Biosystems) by keeping warm successively at 50° C. for 2 minutes and 95° C. for 10 minutes and then repeating 40 cycles of one set to include 95° C. for 15 seconds and 60° C. for 60 seconds. The copy numbers of rat GPR35 gene and rat GAPDH gene expressed were calculated with ABI PRISM 7700 SDS Software. The cycle number at the moment when the fluorescent intensity of a reporter came to a preset value was taken on the ordinate, and logarithm of the copy number of the standard DNA was taken on the abscissa; the standard curve was thus prepared. From the standard curve, the copy number of the expressed gene contained in the reverse transcribed cDNA was calculated and the value obtained by dividing the copy number of the expressed rat GPR35 gene by the copy number of the expressed GAPDH gene was made the expression level of standardized rat GPR35 gene.

The expression levels of standardized rat GPR35 gene in the mucosa layer and the muscle layer were 0.0042 and 0.0002, respectively. In other words, the expression level of GPR35 gene in the mucosa layer was higher by about 21 times than the level in the muscle layer.

The GPR35 gene was selectively expressed in the mucosa layer, suggesting that the GPR35 gene would take part in the absorption and digestion of nutrients and intestinal immunity. For instance, secretion of digestive juice such as gastric juice, etc. can be suppressed by inhibiting cAMP production using an agonist to GPR35. It is thus possible to prevent/treat digestive ulcer, and so on. Also, leakage of electrolytes from the intestinal tract can be prevented by an agonist to GPR35; it is thus possible to prevent/treat diarrhea, malabsorption syndrome, etc. By promoting a cAMP production with an antagonist to GPR35, secretion of various inflammatory cytokines from large intestinal mucosa or macrophage can be prevented; it is thus possible to prevent/treat immune disorders including autoimmune disease, inflammatory bowel disorders, etc.

Example 11

Enhanced Gene Expression of GPR35 Associated with Adipocyte Differentiation

Mouse 3T3-L1 was differentiated into adipocytes, and the GPR35 gene expression levels were assayed prior to and after the differentiation. Adipocyte differentiation was performed under the following culture conditions. 3T3-L1 cells were cultured in basal growth medium (DMEM, 10% bovine serum, 0.2 mM ascorbic acid). After the cells reached confluent, the cells were cultured for 48 hours in differentiation induction medium (DMEM, 10% fetal calf serum, 2.5 µM dexamethasone, 0.5 mM IBMX, 0.2 mM ascorbic acid and 10 µg/ml insulin). Next, the cells were cultured in differentiation maintenance medium (DMEM, 10% fetal calf serum, 0.2 mM ascorbic acid and 10 µg/ml insulin). Total RNA was purified from the cells prior to differentiation and Days 5, 10 and 15 of the maintained differentiation, using ISOGEN. To 50 µl of the total RNA solution, 1 µl of DNAase I (GenHunter) and 5.7 µl of the buffer attached to the kit were added and the mixture was kept warm at 37° C. for 30 minutes. RNA was extracted from the reaction solution using a phenol/chloroform mixture. Then, 5-fold volume of ethanol and ⅛ volume of 3M sodium acetate solution were added to the RNA solution for ethanol precipitation to recover RNA. A mixture of 2.5 µl of 0.2 µg/µl RNA solution, 4 µl of 10 mM deoxynucleotide mixture, 0.5 µl of 50 pmol/µl random primer and 6 µl of distilled water was kept warm at 65° C. for 5 minutes and then ice-cooled. To the solution, 1 µl of SuperScriptIII reverse transcriptase (Invitrogen), 4 µl of the buffer attached to the reverse transcriptase, 1 µl of 0.1M dithiothreitol solution and 1 µl of RNAase inhibitor RNaseOUT (Invitrogen) were added to make the total volume 20 µl. The reverse transcription was carried out under the following conditions. These reaction solutions were kept warm successively at 25° C. for 5 minutes, 50° C. for 60 minutes, 70° C. for 15 minutes and 4° C. for 5 minutes to give the reverse-transcribed cDNA solution.

The copy number of mouse GPR35 gene expressed was determined by the TaqMan PCR method. The reaction solution for the TaqMan PCR to determine the mouse GPR35 gene consisted of 1 µl of reverse transcribed cDNA solution or standard mouse GPR35 DNA, 0.2 µM synthetic DNA forward primer (SEQ ID NO: 32), 0.2 µM synthetic DNA reverse primer (SEQ ID NO: 33), 0.2 µM rat GPR35 TaqMan probe (SEQ ID NO: 34) and TaqMan Universal PCR Master Mix (Applied Biosystems). The total volume of the reaction solution was 25 μl. The PCR reaction was performed using ABI PRISM 7700 Sequence Detector System (Applied Biosystems) by keeping warm successively at 50° C. for 2 minutes and 95° C. for 10 minutes and then repeating 40 cycles of one set to include 95° C. for 15 seconds and 60° C. for 60 seconds. The copy number of mouse GPR35 gene expressed was calculated with ABI PRISM 7700 SDS Software. The cycle number at the moment when fluorescent intensity of a reporter comes to a preset value was taken as an ordinate, and logarithm of the copy number of the standard DNA was taken as an abscissa; the standard curve was thus prepared. From the standard curve, the copy number of the expressed gene contained in the reverse transcribed cDNA was calculated and the copy number of the expressed mouse GPR35 gene contained in the cDNA reverse transcribed from 25 ng of RNA was obtained.

With adipocyte differentiation, the expression level of the GPR35 gene increased. The copy numbers of the expressed GPR35 gene prior to differentiation and Days 5, 10 and 15 of the maintained differentiation were 2300, 22000, 110000 and 160000, respectively.

The expression level of the GPR35 gene increased with adipocyte differentiation, suggesting that GPR35 would play a part in lipolysis, sugar uptake and regulation of adipocyte differentiation. The agonist to GPR35 has an action of decreasing the intracellular cAMP level and the decrease of intracellular cAMP prevents lipolysis to reduce the blood fatty acid level. Thus, the agonist to GPR35 is useful for the prevention/treatment of type II diabetes mellitus. In addition, the antagonist to GPR35 has an action of increasing the intracellular cAMP level and the increase of intracellular cAMP stimulates lipolysis and prevents lipogenesis. Thus, the antagonist to GPR35 is useful for the prevention/treatment of obesity.

Example 12

Screening of Agonist to GPR35 Using AlphaScreen

The human GPR35-expressed CHO cells obtained in REFERENCE EXAMPLE 1 are seeded into one flask of 150 cm$^2$, followed by incubation at 37° C. overnight in a $CO_2$ incubator. After incubation, the cells are detached by 0.5 mM EDTA/PBS and washed with PBS. Subsequently, the cells are suspended in Buffer 1 (HBSS+0.1% BSA, 25 mM HEPES pH 7.3, 0.5 mM IBMX) at a density of $1 \times 10^7$ cells/ml. This cell suspension, 440 μl, is mixed with 22 μl of anti-cAMP acceptor beads and 638 μl of Buffer 1 of the AlphaScreen cAMP Assay Kit (Parkin Elmer), and 10 μl each of the mixture is dispensed in a white 96-well plate (Costar). Next, a compound is diluted with Buffer 1 containing 2 μM of forskolin (FSK) and 10 μl each of the diluted compound is added to each well. In this case, the cell suspension was not put in one row of the plate but a mixture of 9 μl of anti-cAMP acceptor beads and 441 μl of Buffer 1 was charged and a serial dilution of cAMP is added instead of the compound, which is used as a standard. The plate charged with a mixture of the cell suspension and the compound is shaken at room temperature for 30 minutes. Thereafter, 20 μl of Biotinyl camp and 82 μl of Streptavin donor beads were added to 40 ml of Buffer 2 (HBSS+0.1% BSA, 25 mM HEPES pH 7.3, 1.5% Tween 20) of the AlphaScreen cAMP Assay Kit and 30 μl each of the resulting mixture was dispensed to all wells of the plate. The plate was kept shaking for 3 hours at room temperature, and fluorescence intensities were assayed on Fusion α (Parkin Elmer). The cAMP level in each well was calculated from the reaction curves of cAMP added to the plate.

Example 13

Screening of Agonist to GPR35 Using FLIPR

The cells obtained in EXAMPLE 8 above, in which Gα16 and GPR35 were stably co-expressed, were suspended in a medium [αMEM medium (containing no nucleic acid, Invitrogen) supplemented with 10% dialyzed fetal calf serum (Invitrogen), 50 units/ml penicillin/50 ug/ml streptomycin (CAMBREX) and 1 mg/ml geneticin (Invitrogen)] to have $3 \times 10^5$ cells/ml, respectively. Using an 8-channel pipette, 100 μl each per well was inoculated on a 96-well plate for FLIPR (Black plate clear bottom, Costar) ($3.0 \times 10^4$ cells/100 μl/well) and incubated overnight at 37° C. in a 5% $CO_2$ incubator, which were used for the following assay (hereinafter referred to as the cell plate). Per 2 cell plates, 20 ml of H/HBSS (10 ml of 1M HEPES/pH 7.4 (Dojin Chemical Laboratory, Ltd.) was added to 500 ml of HBSS (Invitrogen, Hanks' balanced salt solution without phenol red)), 200 μl of 250 mM Probenecid and 200 μl of fetal bovine serum (FBS) were mixed. Also, 2 vials (50 μg) of Fluo 3-AM (Dojin Chemical Laboratory, Ltd.) were dissolved in 40 μl of dimethylsulfoxide and 40 μl of 20% Pluronic acid (Molecular Probes), and the resulting solution was added to the H/HBSS-Probenecid-FBS described above. After mixing, the medium was removed using an 8-channel pipette, and 100 μl each of the mixture was dispensed into each well of the cell plate, followed by incubation at 37° C. in a 5% $CO_2$ incubator for an hour (dye loading).

A solution containing a test compound was prepared using H/HBSS containing 2.5 mM Probenecid and 220 μl each of the solution was then transferred to a 96-well plate (V-Bottom Plate, Coster) for FLIPR (hereinafter referred to as the sample plate). After completion of the dye loading to the cell plate, the cell plate was washed with a wash buffer of H/HBSS supplemented with 2.5 mM Probenecid, using a plate washer (ELX405, Bio-Tek Instruments). After washing, 100 μl of the wash buffer was left. This cell plate and the sample plate were set on FLIPR (50 μl of sample was transferred from the sample plate to the cell plate by FLIPR) to determine changes in fluorescence intensity with passage of time, thereby to assay the intracellular calcium ion level increasing activity. The same test as described above is conducted using CHO cells, in which no GPR35 is expressed, or CHO cell lines in which control receptors such as histamine H1 receptor, etc. are expressed, to screen compounds capable of specifically increasing the intracellular calcium ion levels in the Gα16 and GPR35-stably co-expressed cells.

INDUSTRIAL APPLICABILITY

The compound or its salts (e.g., GPR35 agonists, GPR35 antagonists), etc., which are obtainable using the screening methods or screening kits of the present invention, are useful as agents for the prevention/treatment of, for example, digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison syndrome, etc.), gastritis, reflux esophagitis, NUD (non-ulcer dyspepsia), non-steroidal anti-inflammatory drug-induced ulcer, postoperative stress-induced hyperacidity and ulcer, etc.], cancer (e.g., digestive cancer (e.g., gastric cancer, colon cancer, gastric MALT lymphoma, etc.), breast cancer, lung cancer, prostate cancer, esophageal cancer, pharyngeal cancer, liver cancer, biliary tract cancer, spleen cancer, renal cancer, bladder cancer, uterine cancer, testicular cancer, thyroid cancer, pancreatic cancer, brain tumor, ovary cancer, blood tumor, etc.), immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], type II diabetes mellitus, obesity, and so on.

The compound or its salts that promotes activities of the receptor of the present invention, the GPR35 agonist, the receptor of the present invention, the polynucleotide encoding the receptor of the present invention, the ligand of the present invention, etc. are useful as agents for the prevention/treatment of, for example, digestive tract (gastrointestinal) disorders [e.g., diarrhea, malabsorption syndrome, irritable bowel syndrome, Crohn's disease, peptic ulcer (e.g., gastric ulcer, duodenal ulcer, marginal ulcer, Zollinger-Ellison, etc.), gastritis, reflux esophagitis, NUD (non-ulcer dyspepsia), non-steroidal anti-inflammatory drug-induced ulcer, postoperative stress-induced hyperacidity and ulcer, etc.], type II diabetes mellitus, and the like.

The compound or its salt that inhibits activities of the receptor of the present invention, the GPR35 agonist, the antisense polynucleotide to the receptor of the present invention, the antibody to the receptor of the present invention, etc. are useful as agents for the prevention/treatment of, for example, immune disorders [e.g., chronic obstructive pulmonary disease, sepsis, atherosclerosis, AIDS, autoimmune disorders (e.g., chronic articular rheumatism, multiple sclerosis, myasthenia gravis, insulin-dependent diabetes mellitus (type I diabetes mellitus), inflammatory bowel disorders, systemic lupus erythematosus, glomerulonephritis, autoimmune hemolytic anemia, Hashimoto disease, ulcerative colitis, primary biliary cirrhosis, idiopathic thrombocytopenic purpura, Harada disease, pernicious anemia, Sjögren's syndrome, Goodpasture's syndrome, etc.), etc.], digestive cancer (e.g., gastric cancer, colon cancer, etc.), obesity, and the like.

Furthermore, the receptor of the present invention (e.g., GPR35, etc.) and its ligands (e.g., quinoxaline-2,3-dione compounds, ellagic acid, etc.) are useful for screening the compound or its salt having the effects of preventing/treating digestive tract (gastrointestinal) disorders, cancer, immune disorders, type II diabetes mellitus, obesity, etc.

---

The invention claimed is:

1. A method of screening a compound or a salt thereof that alters the binding property of a protein comprising the amino acid sequence of SEQ ID NO: 1, or a salt thereof, to a ligand selected from the group consisting of a quinoxaline-2,3-dione compound and ellagic acid, which comprises:
   (a) contacting said protein, or a salt thereof, with said ligand, and determining the binding amount of said ligand to said protein or a salt thereof;
   (b) contacting said protein or a salt thereof with said ligand and said compound, and determining the binding amount of said ligand to said protein or a salt thereof;
and comparing the binding amounts amount of said ligand to said protein or a salt thereof in step (a) and with the binding amount of said ligand to said protein or a salt thereof in step (b); thereby identifying the compound that alters the binding property of the protein.

2. The screening method according to claim 1, wherein the quinoxaline-2,3-dione compound is 6,7-dinitroquinoxaline-2,3-dione, 6-nitro-7-sulfamoylbenzo[f]quinoxaline-2,3-dione, 6-cyano-7-nitroquinoxaline-2,3-dione or 5,7-dinitroquinoxaline-2,3-dione.

3. The screening method according to claim 1, wherein the ligand is ellagic acid.

4. The screening method according to claim 1, wherein the protein is expressed on a cell membrane or present in a membrane fraction of the cell membrane.

5. The screening method according to claim 4, wherein the protein is expressed on a cell membrane by culturing a transformant bearing a DNA encoding the amino acid sequence of SEQ ID NO: 1.

6. The screening method according to claim 1, wherein the ligand is a labeled ligand.

7. A method of screening a compound or a salt thereof that increases or decreases a cell stimulating activity by contacting a protein comprising the amino acid sequence of SEQ ID NO: 1, or a salt thereof, with a ligand selected from the group consisting of a quinoxaline-2,3-dione compound and ellagic acid, wherein the protein is expressed on a cell membrane or present in a membrane fraction of the cell membrane, the method comprising:
   (a) contacting the ligand with said protein, or a salt thereof, and assaying the cell stimulating activity; and
   (b) contacting said ligand and said compound with said protein or a salt thereof, and assaying the cell stimulating activity; and (c) comparing the cell stimulating activity in step (a) with the cell stimulating activity in step (b), wherein the cell stimulating activity is selected from the group consisting of activities that promote intracellular $Ca^{2+}$ release, intracellular cAMP production suppression, activation of microtubule-associated protein kinase (MAP kinase) and receptor internalization activity; thereby identifying the compound that increases or decreases the cell stimulating activity.

8. The screening method according to claim 7, wherein the protein is expressed on a cell membrane by culturing a transformant bearing a DNA encoding the amino acid sequence of SEQ ID NO: 1.

9. The screening method according to claim 4, wherein the ligand is a labeled ligand.

10. The screening method according to claim 7, wherein the ligand is a labeled ligand.

11. A kit for screening a compound or its salt that alters the binding property of a protein comprising the amino acid sequence of SEQ ID NO: 1, or a salt thereof, to a ligand selected from the group consisting of a quinoxaline-2,3-dione compound and ellagic acid, which comprises said protein or a salt thereof, and said ligand.

* * * * *

SEQUENCE LISTING

```
<160> NUMBER OF SEQ ID NOS: 34

<210> SEQ ID NO 1
<211> LENGTH: 309
<212> TYPE: PRT
<213> ORGANISM: Homo sapiens

<400> SEQUENCE: 1

Met Asn Gly Thr Tyr Asn Thr Cys Gly Ser Ser Asp Leu Thr Trp Pro
                 5                  10                  15

Pro Ala Ile Lys Leu Gly Phe Tyr Ala Tyr Leu Gly Val Leu Leu Val
             20                  25                  30

Leu Gly Leu Leu Leu Asn Ser Leu Ala Leu Trp Val Phe Cys Cys Arg
         35                  40                  45

Met Gln Gln Trp Thr Glu Thr Arg Ile Tyr Met Thr Asn Leu Ala Val
     50                  55                  60

Ala Asp Leu Cys Leu Leu Cys Thr Leu Pro Phe Val Leu His Ser Leu
 65                  70                  75                  80

Arg Asp Thr Ser Asp Thr Pro Leu Cys Gln Leu Ser Gln Gly Ile Tyr
                 85                  90                  95

Leu Thr Asn Arg Tyr Met Ser Ile Ser Leu Val Thr Ala Ile Ala Val
            100                 105                 110

Asp Arg Tyr Val Ala Val Arg His Pro Leu Arg Ala Arg Gly Leu Arg
        115                 120                 125

Ser Pro Arg Gln Ala Ala Ala Val Cys Ala Val Leu Trp Val Leu Val
    130                 135                 140

Ile Gly Ser Leu Val Ala Arg Trp Leu Leu Gly Ile Gln Glu Gly Gly
145                 150                 155                 160

Phe Cys Phe Arg Ser Thr Arg His Asn Phe Asn Ser Met Ala Phe Pro
                165                 170                 175

Leu Leu Gly Phe Tyr Leu Pro Leu Ala Val Val Val Phe Cys Ser Leu
            180                 185                 190
```

-continued

```
Lys Val Val Thr Ala Leu Ala Gln Arg Pro Pro Thr Asp Val Gly Gln
        195                 200                 205

Ala Glu Ala Thr Arg Lys Ala Ala Arg Met Val Trp Ala Asn Leu Leu
    210                 215                 220

Val Phe Val Val Cys Phe Leu Pro Leu His Val Gly Leu Thr Val Arg
225                 230                 235                 240

Leu Ala Val Gly Trp Asn Ala Cys Ala Leu Leu Glu Thr Ile Arg Arg
                245                 250                 255

Ala Leu Tyr Ile Thr Ser Lys Leu Ser Asp Ala Asn Cys Cys Leu Asp
            260                 265                 270

Ala Ile Cys Tyr Tyr Met Ala Lys Glu Phe Gln Glu Ala Ser Ala
        275                 280                 285

Leu Ala Val Ala Pro Arg Ala Lys Ala His Lys Ser Gln Asp Ser Leu
    290                 295                 300

Cys Val Thr Leu Ala
305
```

<210> SEQ ID NO 2
<211> LENGTH: 927
<212> TYPE: DNA
<213> ORGANISM: Homo sapiens

<400> SEQUENCE: 2

```
atgaatggca cctacaacac ctgtggctcc agcgacctca cctggccccc agcgatcaag      60
ctgggcttct acgcctactt gggcgtcctg ctggtgctag cctgctgct caacagcctg     120
gcgctctggg tgttctgctg ccgcatgcag cagtggacgg agacccgcat ctacatgacc     180
aacctggcgg tggccgacct ctgcctgctg tgcaccttgc ccttcgtgct gactccctg     240
cgagacacct cagacacgcc gctgtgccag ctctcccagg catctacct gaccaacagg     300
tacatgagca tcagcctggt cacggccatc gccgtggacc gctatgtggc cgtgcggcac     360
ccgctgcgtg cccgcgggct gcggtccccc aggcaggctg cggccgtgtg cgcggtcctc     420
tgggtgctgg tcatcggctc cctggtggct cgctggctcc tggggattca ggagggcggc     480
ttctgcttca ggagcacccg gcacaatttc aactccatgg cgttcccgct gctgggattc     540
tacctgcccc tggccgtggt ggtcttctgc tccctgaagg tggtgactgc cctgccccag     600
aggccacccca ccgacgtggg gcaggcagag gccacccgca aggctgcccg catggtctgg     660
gccaacctcc tggtgttcgt ggtctgcttc ctgcccctgc acgtggggct gacagtgcgc     720
ctcgcagtgg gctggaacgc ctgtgccctc tggagacga tcgtcgcgc cctgtacata     780
accagcaagc tctcagatgc caactgctgc ctggacgcca tctgctacta ctacatggcc     840
aaggagttcc aggaggcgtc tgcactggcc gtggctcccc gtgctaaggc ccacaaaagc     900
caggactctc tgtgcgtgac cctcgcc                                         927
```

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3

```
ccgtcgacaa ggaccatgaa tggcacctac a                                     31
```

<210> SEQ ID NO 4
<211> LENGTH: 31
<212> TYPE: DNA
<213> ORGANISM: Artificial Sequence
<220> FEATURE:
<223> OTHER INFORMATION: Primer

<400> SEQUENCE: 4
ccatcgatct tcccctggca ggcagcacct c                                31

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
gtcgacatga atagtacaac ctgtaacac                                   29

<210> SEQ ID NO 6
<211> LENGTH: 28
<212> TYPE: DNA
<213> ORGANISM: Artificial Sequence
<220> FEATURE:
<223> OTHER INFORMATION: Primer

<400> SEQUENCE: 6
actagtctag gtgaggctca ggatctgg                                    28

<210> SEQ ID NO 7
<211> LENGTH: 307
<212> TYPE: PRT
<213> ORGANISM: Mus musculus

<400> SEQUENCE: 7

Met Asn Ser Thr Thr Cys Asn Ser Thr Leu Thr Trp Pro Ala Ser Val
              5                  10                  15

Asn Asn Phe Phe Ile Ile Tyr Ser Ala Leu Leu Leu Val Leu Gly Leu
             20                  25                  30

Leu Leu Asn Ser Val Ala Leu Trp Val Phe Cys Tyr Arg Met His Gln
         35                  40                  45

Trp Thr Glu Thr Arg Ile Tyr Met Thr Asn Leu Ala Val Ala Asp Leu
     50                  55                  60

Cys Leu Leu Cys Ser Leu Pro Phe Val Leu Tyr Ser Leu Lys Tyr Ser
 65                  70                  75                  80

Ser Ser Asp Thr Pro Val Cys Gln Leu Ser Gln Gly Ile Tyr Leu Ala
                 85                  90                  95

Asn Arg Tyr Met Ser Ile Ser Leu Val Thr Ala Ile Ala Val Asp Arg
            100                 105                 110

Tyr Val Ala Val Arg His Pro Leu Arg Ala Arg Glu Leu Arg Ser Pro
        115                 120                 125

Arg Gln Ala Ala Ala Val Cys Val Ala Leu Trp Val Ile Val Val Thr
    130                 135                 140

Ser Leu Val Val Arg Trp Arg Leu Gly Met Gln Glu Gly Gly Phe Cys
145                 150                 155                 160

Phe Ser Ser Gln Thr Arg Arg Asn Phe Ser Thr Thr Ala Phe Ser Leu
                165                 170                 175

Leu Gly Phe Tyr Leu Pro Leu Ala Ile Val Val Phe Cys Ser Leu Gln
            180                 185                 190

Val Val Thr Val Leu Ser Arg Arg Pro Ala Ala Asp Val Gly Gln Ala
            195                 200                 205

Glu Ala Thr Gln Lys Ala Thr His Met Val Trp Ala Asn Leu Ala Val
    210                 215                 220

Phe Val Ile Cys Phe Leu Pro Leu His Val Val Leu Thr Val Gln Val
225                 230                 235                 240

Ser Leu Asn Leu Asn Thr Cys Ala Ala Arg Asp Thr Phe Ser Arg Ala
            245                 250                 255

Leu Ser Ile Thr Gly Lys Leu Ser Asp Thr Asn Cys Cys Leu Asp Ala
            260                 265                 270

Ile Cys Tyr Tyr Tyr Met Ala Arg Glu Phe Gln Glu Ala Phe Lys Pro
            275                 280                 285

Ala Thr Ser Ser Asn Thr Pro His Lys Ser Gln Tyr Ser Gln Ile Leu
            290                 295                 300

Ser Leu Thr
305

<210> SEQ ID NO 8
<211> LENGTH: 921
<212> TYPE: DNA
<213> ORGANISM: Mus musculus

<400> SEQUENCE: 8
atgaatagta caacctgtaa cagcaccctc acgtggcctg cttccgtcaa caacttttc      60 atcatctact cagccttgct gctggtgctg ggcctgctgc tcaacagcgt ggcactctgg    120
gtattctgct atcgcatgca ccagtggaca gagacccgca tctatatgac caacctggct    180
gtggccgacc tctgcctgct ctgctccttg ccatttgtgc tgtactccct gaaatatagt    240
tcttcagaca caccgtctg ccagctctca cagggcatct acctggccaa cagatacatg     300
agcataagcc tggtcactgc cattgctgtg accgctatg tggcagtgcg catcccctg      360 cgtgcgcgtg agctgcggtc cccgagacag gctgcagcag tgtgtgtggc cctttgggtg    420
atagtggtca cctcctggt agtgcgctgg cgcctgggga tgcaggaggg tggcttctgc     480
ttcagcagcc aaacccggcg caatttcagc accactgcct tctcactgct gggattctac    540
ctgccgctgg ccatcgtggt cttctgctct ttgcaggtag tgactgtgct atcgagaagg    600
ccagccgctg atgtggggca ggcagaggcc acccaaaagg ccacccacat ggtctgggcc    660
aacttggctg tgtttgtcat ctgcttcctg cccttgcatg tggtcctgac cgtgcaggtc    720
tccctgaacc tcaatacctg tgctgcccga gacaccttca gccgtgccct gtccatcaca    780
ggtaaactct cagacaccaa ctgctgcctg gatgccatct gttactacta catggccaga    840
gagttccagg aagcgttcaa gccagccacg tcttccaaca caccccacaa gagccaatat    900
tcccagatcc tgagcctcac c                                              921

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
ctgctactac tacatggcca agga                                            24

```
<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
cgagggtcac gcacagaga                                                     19

<210> SEQ ID NO 11
<211> LENGTH: 23
<212> TYPE: DNA
<213> ORGANISM: Artificial Sequence
<220> FEATURE:
<223> OTHER INFORMATION: Probe

<400> SEQUENCE: 11
ctccccgtgc taaggcccac aaa                                                23

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
ggtctccctg aacctcaata cct                                                23

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
tgtctgagag tttacctgtg atgga                                              25

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctgcccgaga caccttcagc cgt                                                23

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15
gtcgaccacc atgctgagtg gttcccgggc tgtccccac                               39

<210> SEQ ID NO 16
<211> LENGTH: 33
<212> TYPE: DNA
<213> ORGANISM: Artificial Sequence
<220> FEATURE:
<223> OTHER INFORMATION: Primer
```

<400> SEQUENCE: 16
actagtttag gcgagggtca cgcacagaga gtc                                33

<210> SEQ ID NO 17
<211> LENGTH: 40
<212> TYPE: DNA
<213> ORGANISM: Artificial Sequence
<220> FEATURE:
<223> OTHER INFORMATION: Primer

<400> SEQUENCE: 17
gtcgaccacc atgcaaagga cgcatgagga tccaagcgac                         40

<210> SEQ ID NO 18
<211> LENGTH: 38
<212> TYPE: DNA
<213> ORGANISM: Artificial Sequence
<220> FEATURE:
<223> OTHER INFORMATION: Primer

<400> SEQUENCE: 18
gtcgaccacc atggaagcca actattccat ccctctga                           38

<210> SEQ ID NO 19
<211> LENGTH: 340
<212> TYPE: PRT
<213> ORGANISM: Homo sapiens

<400> SEQUENCE: 19

```
Met Leu Ser Gly Ser Arg Ala Val Pro Thr Pro His Arg Gly Ser Glu
              5                  10                  15

Glu Leu Leu Lys Tyr Met Leu His Ser Pro Cys Val Ser Leu Thr Met
         20                  25                  30

Asn Gly Thr Tyr Asn Thr Cys Gly Ser Ser Asp Leu Thr Trp Pro Pro
     35                  40                  45

Ala Ile Lys Leu Gly Phe Tyr Ala Tyr Leu Gly Val Leu Val Leu
 50                  55                  60

Gly Leu Leu Leu Asn Ser Leu Ala Leu Trp Val Phe Cys Cys Arg Met
 65                  70                  75                  80

Gln Gln Trp Thr Glu Thr Arg Ile Tyr Met Thr Asn Leu Ala Val Ala
             85                  90                  95

Asp Leu Cys Leu Leu Cys Thr Leu Pro Phe Val Leu His Ser Leu Arg
        100                 105                 110

Asp Thr Ser Asp Thr Pro Leu Cys Gln Leu Ser Gln Gly Ile Tyr Leu
    115                 120                 125

Thr Asn Arg Tyr Met Ser Ile Ser Leu Val Thr Ala Ile Ala Val Asp
130                 135                 140

Arg Tyr Val Ala Val Arg His Pro Leu Arg Ala Arg Gly Leu Arg Ser
145                 150                 155                 160

Pro Arg Gln Ala Ala Ala Val Cys Ala Val Leu Trp Val Leu Val Ile
                165                 170                 175

Gly Ser Leu Val Ala Arg Trp Leu Leu Gly Ile Gln Glu Gly Gly Phe
            180                 185                 190

Cys Phe Arg Ser Thr Arg His Asn Phe Asn Ser Met Ala Phe Pro Leu
        195                 200                 205

Leu Gly Phe Tyr Leu Pro Leu Ala Val Val Val Phe Cys Ser Leu Lys
    210                 215                 220
```

```
Val Val Thr Ala Leu Ala Gln Arg Pro Pro Thr Asp Val Gly Gln Ala
225                 230                 235                 240

Glu Ala Thr Arg Lys Ala Ala Arg Met Val Trp Ala Asn Leu Leu Val
            245                 250                 255

Phe Val Val Cys Phe Leu Pro Leu His Val Gly Leu Thr Val Arg Leu
        260                 265                 270

Ala Val Gly Trp Asn Ala Cys Ala Leu Leu Glu Thr Ile Arg Arg Ala
    275                 280                 285

Leu Tyr Ile Thr Ser Lys Leu Ser Asp Ala Asn Cys Cys Leu Asp Ala
290                 295                 300

Ile Cys Tyr Tyr Tyr Met Ala Lys Glu Phe Gln Glu Ala Ser Ala Leu
305                 310                 315                 320

Ala Val Ala Pro Arg Ala Lys Ala His Lys Ser Gln Asp Ser Leu Cys
                325                 330                 335

Val Thr Leu Ala
            340

<210> SEQ ID NO 20
<211> LENGTH: 1020
<212> TYPE: DNA
<213> ORGANISM: Homo sapiens

<400> SEQUENCE: 20
atgctgagtg gttcccgggc tgtccccact ccacaccgtg gcagtgaaga gctgctgaag      60
tacatgcttc atagtccttg cgtctctctg accatgaatg gcacctacaa cacctgtggc     120
tccagcgacc tcacctggcc cccagcgatc aagctgggct tctacgccta cttgggcgtc     180
ctgctggtgc taggcctgct gctcaacagc ctggcgctct gggtgttctg ctgccgcatg     240
cagcagtgga cggagacccg catctacatg accaacctgg cggtggccga cctctgcctg     300
ctgtgcacct tgcccttcgt gctgcactcc ctgcgagaca cctcagacac gccgctgtgc     360
cagctctccc agggcatcta cctgaccaac aggtacatga gcatcagcct ggtcacggcc     420
atcgccgtgg accgctatgt ggccgtgcgc acccgctgcc gtgcccgcgg gctgcggtcc     480
cccaggcagg ctgcggccgt gtgcgcggtc ctctgggtgc tggtcatcgg ctccctggtg     540
gctcgctggc tcctggggat tcaggagggc ggcttctgct tcaggagcac ccggcacaat     600
ttcaactcca tggcgttccc gctgctggga ttctacctgc ccctggccgt ggtggtcttc     660
tgctccctga aggtggtgac tgccctggcc cagaggccac ccaccgacgt ggggcaggca     720
gaggccaccc gcaaggctgc ccgcatggtc tgggccaacc tcctggtgtt cgtggtctgc     780
ttcctgcccc tgcacgtggg gctgacagtg cgcctcgcag tgggctggaa cgcctgtgcc     840
ctcctggaga cgatccgtcg cgccctgtac ataaccagca agctctcaga tgccaactgc     900
tgcctggacg ccatctgcta ctactacatg gccaaggagt tccaggaggc gtctgcactg     960
gccgtggctc ccgtgctaa ggccacaaa agccaggact ctctgtgcgt gaccctcgcc    1020

<210> SEQ ID NO 21
<211> LENGTH: 350
<212> TYPE: PRT
<213> ORGANISM: Homo sapiens

<400> SEQUENCE: 21

Met Gln Arg Thr His Glu Asp Pro Ser Asp Ser Phe Arg Met Ala Ala
                5                  10                  15

Ser Leu Gln Lys Glu Ser Arg Phe Arg Pro Gln Asp Met Leu Arg Gly
            20                  25                  30
```

```
Ser His Ser Gly Arg Lys Trp Arg Thr Met Asn Gly Thr Tyr Asn Thr
         35                  40                  45
Cys Gly Ser Ser Asp Leu Thr Trp Pro Pro Ala Ile Lys Leu Gly Phe
     50                  55                  60
Tyr Ala Tyr Leu Gly Val Leu Val Leu Gly Leu Leu Leu Asn Ser
 65                  70                  75                  80
Leu Ala Leu Trp Val Phe Cys Cys Arg Met Gln Gln Trp Thr Glu Thr
                 85                  90                  95
Arg Ile Tyr Met Thr Asn Leu Ala Val Ala Asp Leu Cys Leu Leu Cys
            100                 105                 110
Thr Leu Pro Phe Val Leu His Ser Leu Arg Asp Thr Ser Asp Thr Pro
        115                 120                 125
Leu Cys Gln Leu Ser Gln Gly Ile Tyr Leu Thr Asn Arg Tyr Met Ser
    130                 135                 140
Ile Ser Leu Val Thr Ala Ile Ala Val Asp Arg Tyr Val Ala Val Arg
145                 150                 155                 160
His Pro Leu Arg Ala Arg Gly Leu Arg Ser Pro Arg Gln Ala Ala Ala
                165                 170                 175
Val Cys Ala Val Leu Trp Val Leu Val Ile Gly Ser Leu Val Ala Arg
            180                 185                 190
Trp Leu Leu Gly Ile Gln Glu Gly Gly Phe Cys Phe Arg Ser Thr Arg
        195                 200                 205
His Asn Phe Asn Ser Met Ala Phe Pro Leu Leu Gly Phe Tyr Leu Pro
    210                 215                 220
Leu Ala Val Val Val Phe Cys Ser Leu Lys Val Val Thr Ala Leu Ala
225                 230                 235                 240
Gln Arg Pro Pro Thr Asp Val Gly Gln Ala Glu Ala Thr Arg Lys Ala
                245                 250                 255
Ala Arg Met Val Trp Ala Asn Leu Leu Val Phe Val Val Cys Phe Leu
            260                 265                 270
Pro Leu His Val Gly Leu Thr Val Arg Leu Ala Val Gly Trp Asn Ala
        275                 280                 285
Cys Ala Leu Leu Glu Thr Ile Arg Arg Ala Leu Tyr Ile Thr Ser Lys
    290                 295                 300
Leu Ser Asp Ala Asn Cys Cys Leu Asp Ala Ile Cys Tyr Tyr Tyr Met
305                 310                 315                 320
Ala Lys Glu Phe Gln Glu Ala Ser Ala Leu Ala Val Ala Pro Ser Ala
                325                 330                 335
Lys Ala His Lys Ser Gln Asp Ser Leu Cys Val Thr Leu Ala
            340                 345                 350
```

<210> SEQ ID NO 22
<211> LENGTH: 1050
<212> TYPE: DNA
<213> ORGANISM: Homo sapiens

<400> SEQUENCE: 22

```
atgcaaagga cgcatgagga tccaagcgac tcatttagga tggcagcttc actgcaaaag   60
gagtctcgat tcagacctca agacatgctt cgtgggtctc actcaggaag gaagtggagg  120
accatgaatg gcacctacaa cacctgtggc tccagcgacc tcacctggcc cccagcgatc  180
aagctgggct tctacgccta cttgggcgtc ctgctggtgc taggcctgct gctcaacagc  240
ctggcgctct gggtgttctg ctgccgcatg cagcagtgga cggagacccg catctacatg  300
accaacctgg cggtggccga cctctgcctg ctgtgcacct tgcccttcgt gctgcactcc  360
```

```
ctgcgagaca cctcagacac gccgctgtgc cagctctccc agggcatcta cctgaccaac    420
aggtacatga gcatcagcct ggtcacggcc atcgccgtgg accgctatgt ggccgtgcgg    480
cacccgctgc gtgcccgcgg gctgcggtcc cccaggcagg ctgcggccgt gtgcgcggtc    540
ctctgggtgc tggtcatcgg ctccctggtg gctcgctggc tcctggggat tcaggagggc    600
ggcttctgct tcaggagcac ccggcacaat ttcaactcca tggcgttccc gctgctggga    660
ttctacctgc cctggccgt ggtggtcttc tgctccctga aggtggtgac tgccctggcc    720
cagaggccac ccaccgacgt ggggcaggca gaggccaccc gcaaggctgc ccgcatggtc    780
tgggccaacc tcctggtgtt cgtggtctgc ttcctgcccc tgcacgtggg gctgacagtg    840
cgcctcgcag tgggctggaa cgcctgtgcc ctcctggaga cgatccgtcg cgccctgtac    900
ataaccagca agctctcaga tgccaactgc tgcctgacg ccatctgcta ctactacatg    960
gccaaggagt tccaggaggc gtctgcactg gccgtggctc ccagtgctaa ggcccacaaa   1020
agccaggact ctctgtgcgt gaccctcgcc                                    1050
```

<210> SEQ ID NO 23
<211> LENGTH: 394
<212> TYPE: PRT
<213> ORGANISM: Homo sapiens

<400> SEQUENCE: 23

Met Thr Ala Gly Arg Ser Gln Glu Arg Arg Ala Gln Glu Met Gly Arg
1               5                   10                  15

Gly Ser Val Gln Gly Leu Asp Leu Lys Gly Asp Leu Glu Phe Phe Thr
            20                  25                  30

Ala Pro Met Leu Ser Leu Arg Ser Phe Val Phe Val Gly Val Gly Ser
        35                  40                  45

Gly Leu Thr Ser Ser His Ile Pro Ala Gln Arg Trp Ala Glu Trp Gly
    50                  55                  60

Gln Cys Leu Ala Pro Pro Ala His Ser Leu Val Thr Ser Gly Ser Leu
65                  70                  75                  80

Cys Cys Pro Arg Thr Met Asn Gly Thr Tyr Asn Thr Cys Gly Ser Ser
                85                  90                  95

Asp Leu Thr Trp Pro Pro Ala Ile Lys Leu Gly Phe Tyr Ala Tyr Leu
            100                 105                 110

Gly Val Leu Leu Val Leu Gly Leu Leu Asn Ser Leu Ala Leu Trp
        115                 120                 125

Val Phe Cys Cys Arg Met Gln Gln Trp Thr Glu Thr Arg Ile Tyr Met
130                 135                 140

Thr Asn Leu Ala Val Ala Asp Leu Cys Leu Leu Cys Thr Leu Pro Phe
145                 150                 155                 160

Val Leu His Ser Leu Arg Asp Thr Ser Asp Thr Pro Leu Cys Gln Leu
                165                 170                 175

Ser Gln Gly Ile Tyr Leu Thr Asn Arg Tyr Met Ser Ile Ser Leu Val
            180                 185                 190

Thr Ala Ile Ala Val Asp Arg Tyr Val Ala Val Arg His Pro Leu Arg
        195                 200                 205

Ala Arg Gly Leu Arg Ser Pro Arg Gln Ala Ala Val Cys Ala Val
    210                 215                 220

Leu Trp Val Leu Val Ile Gly Ser Leu Val Ala Arg Trp Leu Leu Gly
225                 230                 235                 240

```
Ile Gln Glu Gly Gly Phe Cys Phe Arg Ser Thr Arg His Asn Phe Asn
            245                 250                 255

Ser Met Ala Phe Pro Leu Leu Gly Phe Tyr Leu Pro Leu Ala Val Val
            260                 265                 270

Val Phe Cys Ser Leu Lys Val Val Thr Ala Leu Ala Gln Arg Pro Pro
            275                 280                 285

Thr Asp Val Gly Gln Ala Glu Ala Thr Arg Lys Ala Ala Arg Met Val
            290                 295                 300

Trp Ala Asn Leu Leu Val Phe Val Val Cys Phe Leu Pro Leu His Val
305                 310                 315                 320

Gly Leu Thr Val Arg Leu Ala Val Gly Trp Asn Ala Cys Ala Leu Leu
                325                 330                 335

Glu Thr Ile Arg Arg Ala Leu Tyr Ile Thr Ser Lys Leu Ser Asp Ala
                340                 345                 350

Asn Cys Cys Leu Asp Ala Ile Cys Tyr Tyr Tyr Met Ala Lys Glu Phe
                355                 360                 365

Gln Glu Ala Ser Ala Leu Ala Val Ala Pro Ser Ala Lys Ala His Lys
            370                 375                 380

Ser Gln Asp Ser Leu Cys Val Thr Leu Ala
385                 390

<210> SEQ ID NO 24
<211> LENGTH: 1182
<212> TYPE: DNA
<213> ORGANISM: Homo sapiens

<400> SEQUENCE: 24
atgacagcag gcagatccca ggagagaaga gctcaggaga tgggaagagg atctgtccag      60
gggttagacc tcaagggtga cttggagttc tttacggcac ccatgctttc tttgaggagt     120
tttgtgtttg tgggtgtggg gtcggggctc acctcctccc acatccctgc ccagaggtgg     180
gcagagtggg ggcagtgcct tgctccccct gctcactctc tggtgacctc cggctccctg     240
tgctgcccca ggaccatgaa tggcacctac aacacctgtg ctccagcga cctcacctgg     300 cccccagcga tcaagctggg cttctacgcc tacttgggcg tcctgctggt gctaggcctg     360
ctgctcaaca gcctggcgct ctgggtgttc tgctgccgca tgcagcagtg gacggagacc     420
cgcatctaca tgaccaacct ggcggtggcc gacctctgcc tgctgtgcac cttgcccttc     480
gtgctgcact ccctgcgaga cacctcagac acgccgctgt gccagctctc ccagggcatc     540
tacctgacca caggtacat gagcatcagc ctggtcacgg ccatcgccgt ggaccgctat     600
gtggccgtgc ggcacccgct gcgtgcccgc gggctgcggt cccccaggca ggctgcggcc     660
gtgtgcgcgg tcctctgggt gctggtcatc ggctccctgg tggctcgctg gctcctgggg     720
attcaggagg gcggcttctg cttcaggagc acccggcaca atttcaactc catggcgttc     780
ccgctgctgg gattctacct gcccctggcc gtggtggtct ctgctccct gaaggtggtg     840 actgccctgg cccagaggcc acccaccgac gtggggcagg cagaggccac ccgcaaggct     900
gcccgcatgt ctgggccaa cctcctggtg ttcgtggtct gcttcctgcc cctgcacgtg     960
gggctgacag tgcgcctcgc agtgggctgg aacgcctgtg ccctcctgga gacgatccgt    1020
cgcgccctgt acataaccag caagctctca gatgccaact gctgcctgga cgccatctgc    1080
tactactaca tggccaagga gttccaggag gcgtctgcac tggccgtggc tcccagtgct    1140
aaggcccaca aaagccagga ctctctgtgc gtgaccctcg cc                       1182
```

<210> SEQ ID NO 25
<211> LENGTH: 29
<212> TYPE: DNA
<213> ORGANISM: Artificial Sequence
<220> FEATURE:
<223> OTHER INFORMATION: Primer

<400> SEQUENCE: 25
gtcgacatga acaatacaaa ttgtagcat                                    29

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26
actagtctag gtgaggctca ggctctg                                      27

<210> SEQ ID NO 27
<211> LENGTH: 306
<212> TYPE: PRT
<213> ORGANISM: Rattus norvegicus

<400> SEQUENCE: 27

Met Asn Asn Thr Asn Cys Ser Ile Leu Pro Trp Pro Ala Ala Val Asn
              5                  10                  15

His Ile Phe Thr Ile Tyr Leu Val Leu Leu Val Leu Gly Leu Leu
         20                  25                  30

Leu Asn Gly Leu Ala Leu Trp Val Phe Cys Tyr Arg Met His Gln Trp
     35                  40                  45

Thr Glu Thr Arg Val Tyr Met Thr Asn Leu Ala Val Ala Asp Val Cys
 50                  55                  60

Leu Leu Cys Ser Leu Pro Phe Val Leu Tyr Ser Leu Lys Tyr Ser Thr
 65                  70                  75                  80

Ser Asp Thr Pro Ile Cys Gln Leu Ser Gln Gly Ile Tyr Leu Val Asn
                 85                  90                  95

Arg Tyr Met Ser Ile Ser Leu Val Thr Ala Ile Ala Val Asp Arg Tyr
            100                 105                 110

Val Ala Val Arg His Pro Leu Arg Ala Arg Glu Leu Arg Ser Pro Arg
        115                 120                 125

Gln Ala Gly Ala Val Cys Val Ala Leu Trp Val Ile Val Val Thr Ser
    130                 135                 140

Leu Val Leu Arg Trp Arg Leu Gly Ile Gln Glu Gly Gly Phe Cys Phe
145                 150                 155                 160

Ser Ser Gln Asn Arg Tyr Asn Phe Ser Thr Thr Ala Phe Ser Leu Leu
                165                 170                 175

Gly Phe Tyr Leu Pro Leu Ala Ile Val Val Phe Cys Ser Leu Gln Val
            180                 185                 190

Val Thr Ala Leu Ala Arg Arg Pro Ala Thr Asp Val Glu Gln Val Glu
        195                 200                 205

Ala Thr Gln Lys Ala Thr Arg Met Val Trp Ala Asn Leu Ala Val Phe
    210                 215                 220

Ile Ile Cys Phe Leu Pro Leu His Leu Ile Leu Thr Val Gln Val Ser
225                 230                 235                 240

```
Leu Asn Leu His Thr Cys Ala Ala Arg Asn Ile Phe Ser Arg Ala Leu
                245                 250                 255

Thr Ile Thr Ala Lys Leu Ser Asp Ile Asn Cys Cys Leu Asp Ala Ile
        260                 265                 270

Cys Tyr Tyr Tyr Met Ala Lys Glu Phe Gln Asp Ala Ser Leu Arg Ala
    275                 280                 285

Thr Ala Ser Ser Thr Pro His Lys Ser Gln Asp Thr Gln Ser Leu Ser
    290                 295                 300

Leu Thr
305

<210> SEQ ID NO 28
<211> LENGTH: 918
<212> TYPE: DNA
<213> ORGANISM: Rattus norvegicus

<400> SEQUENCE: 28
atgaacaata caaattgtag catcctcccg tggcctgctg cagtcaacca catcttcacc      60
atctacttgg tcttgctgct ggtgctgggc ctgctgctca atggcctggc actctgggta     120
ttctgctatc gcatgcacca gtggacggag acccgagtct atatgaccaa cctggctgtg     180
gctgacgtct gcctgctctg ctccttgcca ttcgtgctgt actccctgaa atacagtact     240
tcggacacac ccatctgcca gctctcacag ggcatctacc tggtcaacag gtacatgagc     300
ataagcttgg tcaccgccat tgctgtggac cgctatgtgg cagtgcggca tccccctgcgt    360 gcccgtgagc tgcggtcccc acggcaggct ggagcagtgt gtgtggccct ctgggtgata     420
gtggtcacct ccctggtact gcgctggcgc ctggggatac aggagggtgg cttctgcttc     480
agcagccaaa atcggtacaa cttcagcacc actgccttct cgctgctggg attctacctg     540
ccgctggcca tagtggtctt ctgctctttg caggttgtga ctgcgttggc ccgaaggcca     600
gccactgacg tggagcaggt ggaggccact cagaaggcca cccgcatggt ctgggccaac     660
ttggccgtgt ttatcatctg cttcctgccc ctgcatttga tcctgacagt gcaggtctcc     720
ctgaacctcc acacctgcgc tgcccgaaac atcttcagcc gtgccctgac aatcacagcc     780
aagctctcag acatcaactg ctgcctggat gccatctgtt actactacat ggccaaagag     840
ttccaggatg cgtccttgcg ggccacagcc tctagcacac cccacaagag ccaagatact     900
cagagcctga gcctcacc                                                   918

<210> SEQ ID NO 29
<211> LENGTH: 18
<212> TYPE: DNA
<213> ORGANISM: Artificial
<220> FEATURE:
<223> OTHER INFORMATION: Primer

<400> SEQUENCE: 29
cactcagaag gccacccg                                                    18

<210> SEQ ID NO 30
<211> LENGTH: 22
<212> TYPE: DNA
<213> ORGANISM: Artificial
<220> FEATURE:
<223> OTHER INFORMATION: Primer

<400> SEQUENCE: 30
gggcaggaag cagatgataa ac                                               22
```

```
<210> SEQ ID NO 31
<211> LENGTH: 22
<212> TYPE: DNA
<213> ORGANISM: Artificial
<220> FEATURE:
<223> OTHER INFORMATION: Probe

<400> SEQUENCE: 31
atggtctggg ccaacttggc cg                                                22

<210> SEQ ID NO 32
<211> LENGTH: 15
<212> TYPE: DNA
<213> ORGANISM: Artificial
<220> FEATURE:
<223> OTHER INFORMATION: Primer

<400> SEQUENCE: 32
gcagccaaac ccggc                                                        15

<210> SEQ ID NO 33
<211> LENGTH: 18
<212> TYPE: DNA
<213> ORGANISM: Artificial
<220> FEATURE:
<223> OTHER INFORMATION: Primer

<400> SEQUENCE: 33
gcggcaggta gaatccca                                                     18

<210> SEQ ID NO 34
<211> LENGTH: 28
<212> TYPE: DNA
<213> ORGANISM: Artificial
<220> FEATURE:
<223> OTHER INFORMATION: Probe

<400> SEQUENCE: 34
caatttcagc accactgcct tctcactg                                          28
```